US007335468B2

(12) United States Patent
Zavitz et al.

(10) Patent No.: US 7,335,468 B2
(45) Date of Patent: Feb. 26, 2008

(54) TSG101-GAG INTERACTION AND USE THEREOF

(75) Inventors: Kenton Zavitz, Salt Lake City, UT (US); Scott Morham, Salt Lake City, UT (US); Daniel Albert Wettstein, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 583 days.

(21) Appl. No.: 10/663,407

(22) Filed: Sep. 15, 2003

(65) Prior Publication Data

US 2004/0109861 A1 Jun. 10, 2004

Related U.S. Application Data

(63) Continuation-in-part of application No. 10/224,999, filed on Aug. 20, 2002, now abandoned, and a continuation-in-part of application No. 10/223,172, filed on Aug. 19, 2002, now abandoned, and a continuation-in-part of application No. PCT/US02/08146, filed on Mar. 14, 2002.

(60) Provisional application No. 60/313,695, filed on Aug. 20, 2001, provisional application No. 60/313,239, filed on Aug. 18, 2001, provisional application No. 60/276,259, filed on Mar. 14, 2001.

(51) Int. Cl.
*C12Q 1/70* (2006.01)
*A61K 39/21* (2006.01)

(52) U.S. Cl. .......................... 435/5; 424/208.1
(58) Field of Classification Search ............... 435/5
See application file for complete search history.

(56) References Cited

U.S. PATENT DOCUMENTS

| 5,807,995 | A | 9/1998 | Cohen et al. |
| 5,891,668 | A | 4/1999 | Li et al. |
| 5,892,016 | A | 4/1999 | Brie et al. |
| 6,248,523 | B1 | 6/2001 | Cohen et al. |
| 6,274,312 | B1 | 8/2001 | Gish et al. |
| 2002/0048786 | A1* | 4/2002 | Rosen et al. ............... 435/69.1 |
| 2002/0173622 | A1 | 11/2002 | Wettstein et al. |
| 2002/0177207 | A1 | 11/2002 | Sugiyama et al. |
| 2003/0049607 | A1 | 3/2003 | Greener et al. |

FOREIGN PATENT DOCUMENTS

WO  WO 02/094314  11/2002

OTHER PUBLICATIONS

Pornillos, O., et al., 2002, Structure of the Tsg101 UEV domain in complex with the PTAP motif of the HIV-1 p6 protein, Nature Struct. Biol. 9(11):812-817.*

Mhahilkar, A. M., et al., 1995, Inhibition of HIV-1 Tat-mediated LTR transactivation and HIV-1 infection by anti-Tat single chain intrabodies, EMBO J. 14(7):1542-1551.*

U.S. Appl. No. 09/971,549, filed Oct. 4, 2001, Zavitz et al.

Accola et al., "Efficient Particle Production by Minimal Gag Constructs Which Retain the Carboxy-Terminal Domain of Human Immunodeficiency Virus Type 1 Capsid-p2 and a Late Assembly Domain", *Journal of Virology*, Jun. 2000, 74(12):5395-5402.

Alexander et al., "Unusual Polymorphisms in Human Immunodeficiency Virus Type 1 Associated with Nonprogressive Infection", *Journal of Virology*, May 2000, 74(9):4361-4376.

Babst et al., "Mammalian Tumor Susceptibility Gene 101 (TSG101) and the Yeast Homologue, Vps23p, Both Function in Late Endosomal Trafficking", *Traffic*, 2000, 1:248-258.

Bishop et al., "TSG101/Mammalian VPS23 and Mammalian VPS28 Interact Directly and Are Recruited to VPS4-induced Endosomes", *The Journal of Biological Chemistry*, Apr. 13, 2001, 276(15):11735-11742.

Butkiewicz et al., "Virus-Specific Cofactor Requirement and Chimeric Hepatitis C Virus/GB Virus B Nonstructural Protein 3" *Journal of Virology*, May 2000, 74(9):4291-4301.

Carter, "Tsg101: HIV-1's ticket to ride", *Trends in Microbiology*, May 2002, 10(5):203-205.

Craven et al., "Late Domain Function Identified in the Vesicular Stomatitis Virus M Protein by Use of Rhabdovirus-Retrovirus Chimeras", *Journal of Virology*, Apr. 1999, 73(4):3359-3365.

Crump et al., "Inhibition of the Interaction between Tyrosine-based Motifs and the Medium Chain Subunit of the AP-2 Adapter Complex by Specific Tyrphostins", *The Journal of Biological Chemistry*, Oct. 23, 1998, 273(43):28073-28077.

Demirov et al., "Overexpression of the N-Terminal domain of TSG101 inhibits HIV-1 budding by blocking late domain function", *PNAS*, Jan. 22, 2002, 99(2):955-960.

Desai et al., "Molecular cloning and primary nucleotide sequence analysis of a distinct human immunodeficiency virus isolate reveal significant divergence in its genomic sequences", *PNAS*, Nov. 1986, 83(21):8380-8384.

Deschambeault et al., "Polarized Human Immunodeficiency Virus Budding in Lymphocytes Involves a Tyrosine-Based Signal and Favors Cell-to-Cell Viral Transmission", *Journal of Virology*, Jun. 1999, 73(6):5010-5017.

Farrar et al., "Characterisation of a Series of Human Immunodeficiency Virus Isolates Derived Sequentially From a Single Patient", *Journal of Medical Virology*, 1991, 34:104-113.

Garnier et al., "Identification of Retroviral Late Domains as Determinants of a Particle Size", *Journal of Virology*, Mar. 1999, 73(3):2309-2320.

Garrus, et al., "Tsg101 and the Vacuolar Protein Sorting Pathway Are Essential for HIV-1 Budding", *Cell*, Oct. 5, 2001, 107:55-65.

(Continued)

*Primary Examiner*—Jeffrey S. Parkin
(74) *Attorney, Agent, or Firm*—Herbert L. Ley, III; Jay Z. Zhang; Myriad IP Department

(57) ABSTRACT

Isolated protein complexes are provided comprising Tsg101 and HIV GAG or GAGp6. The protein complexes are useful in screening assays for selecting compounds effective in modulating the Tsg101-HIV GAG or GAGp6 interaction within the protein complexes.

8 Claims, 8 Drawing Sheets

OTHER PUBLICATIONS

Harty et al., "A PPxY motif within the VP40 protein of Ebola virus interacts physically and functionally with a ubiquitin ligase: Implications for filovirus budding", *PNAS*, Dec. 5, 2000, 97(25):13871-13876.

Harty et al., "A Proline-Rich Motif within the Matrix Protein of Vesicular Stomatitis Virus and Rabies Virus Interacts with WW Domains of Cellular Proteins: Implications for Viral Budding", *Journal of Virology*, Apr. 1999, 73(4):2921-2929.

Harvey et al., "Nedd4-like proteins: an emerging family of ubiquitin-protein ligases implicated in diverse cellular functions", *Trends in Cell Biology*, May 1999, 9:166-169.

Heinrichs et al., "In vivo analysis of the functional domains of the Drosophila splicing regulator RBP1", 1997, *PNAS*, 94:115-120.

Huang et al., "$p6^{Gag}$ Is Required for Particle Production from Full-Length Human Immunodeficiency Virus Type 1 Molecular Clones Expressing Protease", *Journal of Virology*, Nov. 1995, 69(11):6810-6818.

Jayakar et al., "Mutations in the PPPY Motif of Vesicular Stomatitis Virus Matrix Protein Reduce Virus Budding by Inhibiting a Late Step in Viron Release", *Journal of Virology*, Nov. 2000, 74(21):9818-9827.

Levin et al., "Inhibition of Early and Late Events of the HIV-1 Replication Cycle by Cytoplasmic Fab Intrabodies against the Matrix Protein, p17", *Molecular Medicine*, Feb. 1997, 3(2):96-110.

Luban, "HIV-1 and Ebola virus: The getaway driver nabbed", *Nature Medicine*, Dec. 2001, 7(12):1278:1280.

Martin-Serrano et al., "HIV-1 and Ebola virus encode small peptide motifs that recruit Tsg101 to sites of particle assembly to facilitate egress", *Nature Medicine*, Dec. 2001, 7(12):1313-1319.

Mhashilkar et al., "Inhibition of HIV-1 Tat-mediated LTR transactivation and HIV-1infection by anti-Tat single chain intrabodies", *The EMBO Journal*, 1995, 14(7):1542-1551.

Myers et al., "Tsg101, an Inactive Homologue of Ubiquitin Ligase E2, Interacts Specifically with Human Immunodeficiency Virus Type 2 Gag Polyprotein and Results in Increased Levels of Unbiquitinated Gag", *Journal of Virology*, Nov. 2002, 76(22):11226-11235.

NCBI Entrez Protein Database Accession No. AAB38034, Dec. 5, 1996.

NCBI Entrez Protein Database Accession No. AAB83138, Nov. 6, 1997.

NCBI Entrez Protein Database Accession No. AAB83216, Nov. 6, 1997.

NCBI Entrez Protein Database Accession No. AAB83821, Nov. 6, 1997.

NCBI Entrez Protein Database Accession No. AAD03232, Jan. 6, 1999.

NCBI Entrez Protein Database Accession No. AAD03240, Jan. 6, 1999.

NCBI Entrez Protein Database Accession No. AAD17020, Jun. 1, 2001.

NCBI Entrez Protein Database Accession No. AAF35354, Feb. 23, 2000.

NCBI Entrez Protein Database Accession No. CAB92786, Sep. 20, 2000.

NCBI Entrez Protein Database Accession No. P35962, Jul. 15, 1998.

Ott et al., "Ubiquitin Is Covalently Attached to the $p6^{Gag}$ Proteins of Human Immunodeficiency Virus Type 1 and Simian Immunodeficiency Virus and to the $p12^{Gag}$ Protein of Moloney Murine Leukemia Virus", *Journal of Virology*, Apr. 1998, 72(4):2962-2968.

Parent et al., "Positionally Independent and Exchangeable Late Budding Functions of the Rous Sarcoma Virus and Human Immunodeficiency Virus Gag Proteins", *Journal of Virology*, Sep. 1995, 69(9):5455-5460.

Patnaik et al., "Ubiquitin is part of the retrovirus budding machinery", *PNAS*, Nov. 21, 2000, 97(24):13069-13074.

Pornillos et al., Structure and functional interactions of the Tsg101 UEV domain, *The EMBO Journal*, 2002, 21(10):2397-2406.

Pornillos et al., "Structure of the Tsg101 UEV domain in complex with the PTAP motif of the HIV-1 p6 protein", *Nature Structural Biology*, Nov. 2002, 9(11):812-817.

Puffer et al., "Equine Infectious Anemia Virus Gag Polyprotein Late Domain Specifically Recruits Cellular AP-2 Adapter Protein Complexes during Virion Assembly", *Journal of Virology*, Dec. 1998, 72(12):10218-10221.

Puffer et al., "Equine Infectious Anemia Virus Utilizes a YXXL Motif within the Late Assembly Domain of the Gag p9 Protein", *Journal of Virology*, Sep. 1997, 71(9):6541-6546.

Rossi, "Therapeutic applications of catalytic antisense RNAs (ribozymes)", *CIBA Foundation Symposium*, 1997, 209:195-206.

Savarino et al., "The Biochemistry of Gene Therapy for AIDS", *Clin. Chem. Lab. Med.*, 1998, 36(4):205-210.

Schubert et al., "Proteasome inhibition interferes with Gag polyprotein processing, release, and maturation of HIV-1 and HIV-2", *PNAS*, Nov. 21, 2000, 97(24):13057-13062.

Sorkina et al., "Clathrin, adaptors and eps15 in endosomes containing activated epidermal growth factor receptors", *Journal of Cell Science*, 1999, 112:317-327.

Strack et al., "A role for ubiquitin ligase recruitment in retrovirus release", *PNAS*, Nov. 21, 2000, 97(24):13063-13068.

Verkhivker, "Towards understanding the mechanisms of molecular recognition by computer simulations of ligand-protein interactions", *Journal of Molecular Recognition*, 1999, 12:371-389.

Verplank et al., "Tsg101, a homologue of ubiquitin-conjugating (E2) enzymes, binds the L domain in HIV type 1 Pr55Gag", *PNAS*, Jul. 3, 2001, 98(14):7724-7729.

Vogt., "Ubiquitin in retrovirus assembly: Actor or bystander?", *PNAS*, Nov. 21, 2000, 97(24):12945-12947.

Whittle et al., "Protein Structure-Based Drug Design", *Annu. Rev. Biophys. Biomol. Struct.*, 1994, 23:349-375.

Yasuda et al., "A Proline-Rich Motif (PPPY) in the Gag Polyprotein of Mason-Pfizer Monkey Virus Plays a Maturation-Independent in Viron Release", *Journal of Virology*, May 1998, 72(5):4095-4103.

Yuan et al., "Infectivity of Moloney Murine Leukemia Virus Defective in Late Assembly Events Is Restored by Late Assembly Domains of Other Retroviruses", *Journal of Virology*, Aug. 2000, 74(16):7250-7260.

Yuan et al., "Mutations altering the Moloney murine leukemia virus p12 Gag protein affect virion production and early events of the virus life cycle", *The EMBO Journal*, 1999, 18(17):4700-4710.

Zhang et al., "Drug Resistance during Indinavir Therapy Is Caused by Mutations in the Protease Gene and in Its Gag Substrate Cleavage Sites", Journal of Virology, Sep. 1997, 71(9):6662-6670.

Bishop et al., "Mammalian class E vps proteins recognize ubiquitin and act in the removal of endosomal protein-ubiquitin conjugates", *J Cell Bio.*, Apr. 1, 2002, 157(1):91-101.

Liu et al., "Overexpression of tumor susceptibility gene TSG101 in human papillary thyroid carcinomas", *Oncogene*, Jul. 18, 2002, 21(31):4830-4837.

Sun et al., "Tumor Susceptibility gene 101 protein represses androgen receptor transactivation and interacts with p300", *Cancer*, Aug. 15, 1999, 86(4):689-696.

Xie et al., "Cell cycle-dependent subcellular localization of the TSG101 protein and mitotic and nuclear abnormalities associated with TSG101 deficiency", *PNAS*, Feb. 17, 1998, 95(4):1595-600.

Zhong et al., "Perturbation of TSG101 protein affects cell cycle progression", *Cancer Research*, Jul. 1, 1998, 58(13):2699-26702.

\* cited by examiner

```
siRNA#1:   5'-    CAGAGACCUAACUGUACGUdTdT-3'   (SEQ ID NO:43)
                  |||||||||||||||||||
           3'-dTdTGUCUCUGGAUUGACAUGCA      -5'  (SEQ ID NO:44)

siRNA#2:   5'-    ACUGUCAAUGUUAUUACUCdTdT-3'   (SEQ ID NO:45)
                  |||||||||||||||||||
           3'-dTdTUGACAGUUACAAUAAUGAG      -5'  (SEQ ID NO:46)

siRNA#3:   5'-    CUAAUGAACCUCACUGGAAdTdT-3'   (SEQ ID NO:47)
                  |||||||||||||||||||
           3'-dTdTGAUUACUUGGAGUGACCUU      -5'  (SEQ ID NO:48)

siRNA#4:   5'-    AUGAACCUCACUGGAACAAdTdT-3'   (SEQ ID NO:49)
                  |||||||||||||||||||
           3'-dTdTUACUUGGAGUGACCUUGUU      -5'  (SEQ ID NO:50)

siRNA#5:   5'-    UGGCUACUGGACACAUACCdTdT-3'   (SEQ ID NO:51)
                  |||||||||||||||||||
           3'-dTdTACCGAUGACCUGUGUAUGG      -5'  (SEQ ID NO:52)

siRNA#6:   5'-    UAUCUUCCUUAUCUACAUGdTdT-3'   (SEQ ID NO:53)
                  |||||||||||||||||||
           3'-dTdTAUAGAAGGAAUAGAUGUAC      -5'  (SEQ ID NO:54)
```

Figure 5a siRNA#7:
5'-     CAAUCAGCGAGGACACCAUdTdT-3'     (SEQ ID NO:55)
        ||||||||||||||||||||
3'-dTdTGUUAGUCGCUCCUGUGGUA    -5'      (SEQ ID NO:56)

siRNA#8:
5'-     ACUGGAAGAGAUGGUUACCdTdT-3'     (SEQ ID NO:57)
        ||||||||||||||||||||
3'-dTdTUGACCUUCUCUACCAAUGG    -5'      (SEQ ID NO:58)

siRNA#9:
5'-     AACGCUAUUGAAGACACUAdTdT-3'     (SEQ ID NO:59)
        ||||||||||||||||||||
3'-dTdTUUGCGAUAACUUCUGUGAU    -5'      (SEQ ID NO:60)

siRNA#10:
5'-     ACGCUAUUGAAGACACUAUdTdT-3'     (SEQ ID NO:61)
        ||||||||||||||||||||
3'-dTdTUGCGAUAACUUCUGUGAUA    -5'      (SEQ ID NO:62)

siRNA#11:
5'-     CGCUAUUGAAGACACUAUCdTdT-3'     (SEQ ID NO:63)
        ||||||||||||||||||||
3'-dTdTGCGAUAACUUCUGUGAUAG    -5'      (SEQ ID NO:64)

Figure 5b

```
                                                                    UUC
shRNA1: (SEQ ID NO:65)        5'-CAGAGACCUAACUGUACGU      A
                                 |||||||||||||||||||      A
                              3'-[UUU]UUGUCUCUGGAUUGACAUGCA   G
                                                            AGA

UUC
shRNA2: (SEQ ID NO:66)        5'-ACUGUCAATGUUAUUACUC      A
                                 |||||||||||||||||||      A
                              3'-[UUU]UUUGACAGUUACAAUAAUGAG  G
                                                            AGA

UUC
shRNA3: (SEQ ID NO:67)        5'-CUAAUGAACCUCACUGGAA      A
                                 |||||||||||||||||||      A
                              3'-[UUU]UUGAUUACUUGGAGUGACCUU  G
                                                            AGA

UUC
shRNA4: (SEQ ID NO:68)        5'-AUGAACCUCACUGGAACAA      A
                                 |||||||||||||||||||      A
                              3'-[UUU]UUUACUUGGAGUGACCUUGUU  G
                                                            AGA

UUC
shRNA5: (SEQ ID NO:69)        5'-UGGCUACUGGACACAUACC      A
                                 |||||||||||||||||||      A
                              3'-[UUU]UUACCGAUGACCUGUGUAUGG  G
                                                            AGA

UUC
shRNA6: (SEQ ID NO:70)        5'-UAUCUUCCUUAUCUACAUG      A
                                 |||||||||||||||||||      A
                              3'-[UUU]UUAUAGAAGGAAUAGAUGUAC  G
                                                            AGA
```

Figure 6a

```
                                                  UUC
shRNA7: (SEQ ID NO:71)    5'-CAAUCAGCGAGGACACCAU    A
                             ||||||||||||||||||     A
                       3'-[UUU]UUGUUAGUCGCUCCUGUGGUA G
                                                  AGA

UUC
shRNA8: (SEQ ID NO:72)    5'-ACUGGAAGAGAUGGUUACC    A
                             |||||||||||||||||||    A
                       3'-[UUU]UUUGACCUUCUCUACCAAUGG G
                                                  AGA

UUC
shRNA9: (SEQ ID NO:73)    5'-AACGCUAUUGAAGACACUA    A
                             ||||||||||||||||||     A
                       3'-[UUU]UUUUGCGAUAACUUCUGUGAU G
                                                  AGA

UUC
shRNA10: (SEQ ID NO:74)   5'-ACGCUAUUGAAGACACUAU    A
                             |||||||||||||||||||    A
                       3'-[UUU]UUUGCGAUAACUUCUGUGAUA G
                                                  AGA

UUC
shRNA11: (SEQ ID NO:75)   5'-CGCUAUUGAAGACACUAUC    A
                             |||||||||||||||||||    A
                       3'-[UUU]UUGCGAUAACUUCUGUGAUAG G
                                                  AGA
```

Figure 6b

TSG101-GAG INTERACTION AND USE THEREOF

CROSS-REFERENCE TO RELATED APPLICATIONS

This application is a continuation-in part, and claims priority, of PCT Application No. PCT/US02/08146 filed on Mar. 14, 2002, U.S. patent application Ser. No. 10/223,172 filed on Aug. 19, 2002 now abandoned, and U.S. patent application Ser. No. 10/224,999 filed on Aug. 20, 2002 now abandoned, the contents of which are incorporated herein by reference in their entirety. PCT Application No. PCT/US02/08146 claims the benefit of U.S. Provisional Application No. 60/276,259 filed on Mar. 14, 2001, U.S. patent application Ser. No. 09/972,035 filed on Oct. 4, 2001, and U.S. patent application Ser. No. 09/971,549 filed on Oct. 4, 2001. U.S. patent application Ser. No. 10/223,172 claims the benefit of U.S. Provisional Application No. 60/313,239 filed on Aug. 18, 2001. U.S. patent application Ser. No. 10/224,999 claims the benefit of U.S. Provisional Application No. 60/313,695 filed on Aug. 20, 2001.

TECHNICAL FIELD

The present invention generally relates to methods of drug screening and methods of treating diseases, particularly to methods of selecting anti-viral drug candidates and methods of treating viral infection.

SEQUENCE LISTING

A Sequence Listing containing all relevant nucleotide and/or amino acid sequences has been submitted on 3 compact discs (CDs), each CD containing one file entitled "1907.04-1 2006-11-03 NEW-SEQ-LIST (TXT) BGJ-RJB.ST25.txt." This file was created Nov. 3, 2006, and written onto CD Nov. 17, 2006, and is 13 kilobytes in size. The information contained in this Sequence Listing is hereby incorporated by reference in its entirety.

BACKGROUND OF THE INVENTION

Human immunodeficiency virus (HIV) infection causes the acquired immunodeficiency syndrome (commonly known as AIDS). HIV is a retrovirus that primarily infects T cells expressing the CD4 glycoprotein, i.e., $CD4^+$ T-cells, which are also known as helper T-cells. HIV virus multiplies in helper T-cells and quickly destroys the host helper T-cells, resulting in cellular immunity depression and leaving the infected patient susceptible to opportunistic infections, malignancies and various other pathological conditions. Ultimately, HIV infection can cause depletion of helper T-cells and collapse of a patient's immune defenses. Not surprisingly, HIV-infected individuals and AIDS patients typically develop AIDS-related conditions such as AIDS-related complex (ARC), progressive generalized lymphadenopathy (PGL), dementia, tropical paraparesis, Kaposi's sarcoma, thrombocytopenia purpurea, herpes infection, cytomegalovirus infection, Epstein-Barr virus related lymphomas among others. In any case, the HIV viruses in an infected individual are infectious and can be transmitted to other people through blood transfusion or sexual contacts.

There has been a great deal of effort in the past fifteen years or so in developing methods and pharmaceutical compounds for treating HIV infection and AIDS. The therapeutic approaches have been mostly focused on a limited number of drug targets, namely HIV reverse transcriptase, HIV protease, and HIV integrase. A number of reverse transcriptase inhibitors and protease inhibitors have been developed or marketed. Examples of nucleoside reverse transcriptase inhibitors include Zidovudine, Stavudine, Lamivudine, and ddI. Examples of non-nucleoside reverse transcriptase inhibitors include Efavirenz, Delavirdine, and Abacavir. In addition, a number of HIV protease inhibitors are commercially available including Ritonavir, Nelfinavir, Indinavir and Saquinavir.

However, HIV typically undergoes active mutations as it multiplies. In addition, there are extensive genetic variations in HIV partly due to high mutation rate. Therefore, mutations in HIV reverse transcriptase and protease arise frequently in infected individuals and render the virus resistant to the inhibitor administered to patients. Combination therapy, generally referred to as HAART (highly active anti-retroviral therapy), has been developed in which a combination of different anti-HIV inhibitors is administered to a patient. However, viral resistance to combination therapies still frequently develops.

In addition, many of the anti-HIV compounds known in the art have other serious drawbacks. For example, the reverse transcriptase inhibitors such as AZT and ddI are fairly toxic and cause serious side effects in patients treated with such compounds.

Therefore, although limited success for controlling HIV infection and AIDS has been achieved with previously developed anti-HIV compounds, there is a need for alternative therapeutic approaches that overcome the shortcomings of currently available drugs.

SUMMARY OF THE INVENTION

It has been discovered that human tumor susceptibility gene 101 ("Tsg101") interacts with HIV GAGp6. Particularly, the interaction between Tsg101 and HIV GAG is essential for HIV maturation and release from host cells. Thus, the protein complexes formed by Tsg101 and HIV GAG or GAGp6, as well as Tsg101 alone, can be used in screening assays to select compounds capable of modulating the functions and activities of Tsg101 or the interaction between Tsg101 and HIV GAG or GAGp6. The identified compounds can be useful in inhibiting lentivirus propagation, particularly HIV propagation, and in treating HIV infection and AIDS.

Accordingly, in accordance with a first aspect of the present invention, an isolated protein complex is provided having a first protein, which is Tsg101 or a Tsg101 fragment, or a homologue or derivative thereof interacting with a second protein, which is HIV GAG polypeptide or fragment, or a homologue or derivative thereof. In a preferred embodiment, the first protein is a fusion protein containing (a) Tsg101 or (b) a Tsg101 homologue or (c) a Tsg101 fragment or a homologue thereof. In another preferred embodiment, the second protein can be a fusion protein containing (a) HIV GAG polypeptide or (b) an HIV GAG homologue or (c) an HIV GAG fragment or a homologue thereof.

In another aspect of the invention, an isolated protein complex is provided having a first protein, which is Tsg101 or a Tsg101 fragment, or a homologue or derivative thereof interacting with a second protein, which is HIV GAGp6 or fragment, or a homologue or derivative thereof. In a preferred embodiment, the first protein is a fusion protein containing (a) Tsg101 or (b) a Tsg101 homologue or (c) a Tsg101 fragment or a homologue thereof. In another preferred embodiment, the second protein is a fusion protein containing (a) HIV GAGp6 polypeptide or (b) an HIV GAGp6 homologue or (c) an HIV GAGp6 fragment or a homologue thereof.

The present invention also provides an isolated protein complex comprising: (a) a first protein which is selected from group consisting of (i) Tsg101 protein, (ii) a Tsg101 protein homologue having an amino acid sequence at least 90% identical to that of Tsg101 and capable of interacting with HIV GAGp6, (iii) a Tsg101 protein fragment containing the Tsg101 UEV domain, or a homologue of thereof having an amino acid sequence at least 90% identical to that of the fragment, and (iv) a fusion protein containing said Tsg101 protein, said Tsg101 protein homologue, or said Tsg101 protein fragment or said homologue of the fragment; and (b) a second protein selected from the group consisting of (1) HIV GAG polypeptide, (2) an HIV GAG polypeptide homologue having an amino acid sequence at least 50%, 60%, 70%, 80%, or 90% identical to that of HIV GAG polypeptide and capable of interacting with Tsg101, (3) HIV GAGp6, (4) an HIV GAGp6 homologue having an amino acid sequence at least 50%, 60%, 70%, 80%, or 90% identical to that of HIV GAGp6 polypeptide and capable of interacting with Tsg101, (5) an HIV GAGp6 fragment capable of interacting with Tsg101, or an HIV GAGp6 homologue capable of interacting with Tsg101, and (6) a fusion protein containing said HIV GAG polypeptide, said HIV GAG polypeptide homologue, said HIV GAGp6 protein, said HIV GAGp6 homologue or said HIV GAGp6 fragment or homologue thereof. In specific embodiments, the HIV GAGp6 fragment has a contiguous span of at least 10 amino acid residues of a naturally occurring HIV GAGp6, said contiguous span containing a P(T/S)AP (SEQ ID NO:1 or SEQ ID NO:3) late domain motif. Preferably, the HIV GAGp6 fragment contains an amino acid sequence selected from the group of SEQ ID NOs:25-32.

The present invention further provides an isolated protein complex comprising a first protein which is Tsg101 or a Tsg101 fragment, or a homologue or derivative thereof interacting with a second protein which is a retrovirus GAG polypeptide containing a P(T/S)AP (SEQ ID NO:1 or SEQ ID NO:3) late domain motif or a homologue or derivative or fragment of said retrovirus GAG polypeptide. Preferably, the retrovirus is a lentivirus. More preferably, the retrovirus is a primate lentivirus such as a virus selected from the group consisting of HIV-1, HIV-2, HIV-3, and simian immunodeficiency viruses. The lentivirus can also be a non-primate lentivirus selected from the group consisting of bovine lentiviruses, feline lentiviruses, and ovine/caprine lentiviruses.

Thus, an isolated protein complex can include:
(a) a first protein which is selected from group consisting of
(i) Tsg101 protein,
(ii) a Tsg101 protein homologue having an amino acid sequence at least 50%, 60%, 70%, 80%, or 90% identical to that of Tsg101 and capable of interacting with HIV GAGp6,
(iii) a Tsg101 protein fragment containing the Tsg101 UEV domain, or a homologue thereof having at least 50%, 60%, 70%, 80%, or 90% amino acid sequence identity with said Tsg101 fragment, and
(iv) a fusion protein containing said Tsg101 protein, said Tsg101 protein homologue or said Tsg101 protein fragment or homologue thereof; and
(b) a second protein selected from the group consisting of
(1) a retrovirus GAG polypeptide having the P(T/S)AP (SEQ ID NO:1 or SEQ ID NO:3) late domain motif,
(2) a homologue of said retrovirus GAG polypeptide, said homologue having an amino acid sequence at least 50%, 60%, 70%, 80%, or 90% identical to that of said retrovirus GAG polypeptide and capable of interacting with Tsg101,
(3) a fragment of said retrovirus GAG polypeptide, said fragment being capable of interacting with Tsg101, and
(4) a fusion protein containing said retrovirus GAG polypeptide, said retrovirus GAG polypeptide homologue or said retrovirus GAG polypeptide fragment.

In another specific embodiment, an isolated protein complex can include:
(a) a first protein which is selected from group consisting of
(i) Tsg101 protein,
(ii) a Tsg101 protein homologue having an amino acid sequence at least 50%, 60%, 70%, 80%, or 90% identical to that of Tsg101 and capable of interacting with HIV GAGp6,
(iii) a Tsg101 protein fragment containing the Tsg101 UEV domain, or a homologue thereof having at least 50%, 60%, 70%, 80%, or 90% amino acid sequence identity with said Tsg101 fragment, and
(iv) a fusion protein containing said Tsg101 protein, said Tsg101 protein homologue or said Tsg101 protein fragment or homologue thereof; and
(b) a second protein selected from the group consisting of
(1) a primate lentivirus GAG polypeptide,
(2) a primate lentivirus GAG polypeptide homologue having an amino acid sequence at least 90% identical to that of said primate lentivirus GAG polypeptide and capable of interacting with Tsg101,
(3) a primate lentivirus GAGp6 protein,
(4) a primate lentivirus GAGp6 homologue having an amino acid sequence at least 90% identical to that of HIV GAGp6 polypeptide and capable of interacting with Tsg101,
(5) a primate lentivirus GAGp6 fragment capable of interacting with Tsg101, and
(6) a fusion protein containing said primate lentivirus GAG polypeptide, said primate lentivirus GAG polypeptide homologue, said primate lentivirus GAGp6 protein, said primate lentivirus GAGp6 homologue or said primate lentivirus GAGp6 fragment.

In yet another aspect, the present invention also provides a method for making the protein complexes of the present invention. The method includes the steps of providing the first protein and the second protein in the protein complexes of the present invention and contacting said first protein with said second protein. In addition, the protein complexes can be prepared by isolation or purification from tissues and cells or produced by recombinant expression of their protein members.

The present invention further relates to a fusion protein having a first polypeptide covalently linked to a second polypeptide, wherein said first polypeptide is Tsg101 or Tsg101 fragment, or a homologue thereof, and wherein said second polypeptide is HIV GAG or a GAG fragment, or a homologue thereof. Isolated nucleic acids encoding the fusion protein are also provided.

In yet another aspect of the present invention, antibodies immunoreactive with the protein complexes of the present invention are provided. In one embodiment, an antibody is selectively immunoreactive with a protein complex of the present invention. In another embodiment, a bifunctional antibody is provided which has two different antigen binding sites, each being specific to a different interacting protein member in a protein complex of the present invention. The antibodies of the present invention can take various forms including polyclonal antibodies, monoclonal antibodies, chimeric antibodies, antibody fragments such as Fv fragments, single-chain Fv fragments (scFv), Fab' fragments, and F(ab')$_2$ fragments. Preferably, the antibodies are partially or fully humanized antibodies. The antibodies of the present invention can be readily prepared using procedures generally known in the art. For example, recombinant libraries such as phage display libraries and ribosome display libraries may be used to screen for antibodies with desirable specificities. In addition, various mutagenesis techniques such as site-directed mutagenesis and PCR diversification may be used in combination with the screening assays.

The present invention further relates to protein microchips comprising one or more of the protein complexes of the present invention and/or one or more antibodies according to the present invention. Such protein microchips can be useful in large-scale high throughput screening assays involving the protein complexes.

In yet another aspect of the present invention, screening methods are provided for selecting modulators of a protein complex formed between Tsg101 or Tsg101 fragment, or a homologue or derivative thereof and HIV GAG or GAG fragment, or a homologue or derivative thereof. Screening methods are also provided for selecting modulators of Tsg101. The compounds identified in the screening methods of the present invention can be used in studying the interaction between Tsg101 and HIV GAG and understanding the mechanism of HIV viral propagation. The selected compounds may also be useful in preventing or ameliorating diseases or disorders such as viral infection, particularly HIV infection and AIDS.

Thus, test compounds may be screened in an in vitro binding assay to select compounds capable of binding a protein complex of the present invention or Tsg110. In addition, in vitro dissociation assays may also be employed to select compounds capable of dissociating the protein complexes identified in accordance with the present invention. An in vitro screening assay may also be used to select compounds that trigger or initiate the formation of, or stabilize, a protein complex of the present invention. In preferred embodiments, in vivo assays such as yeast two-hybrid assays and various derivatives thereof, preferably reverse two-hybrid assays, are utilized in selecting compounds that interfere with or disrupt protein-protein interactions between Tsg101 or Tsg101 fragment, or a homologue or derivative thereof and HIV GAGp6 or GAGp6 fragment, or a homologue or derivative thereof. In addition, systems such as yeast two-hybrid assays are also useful in selecting compounds capable of triggering or initiating, enhancing or stabilizing protein-protein interactions between Tsg101 or Tsg101 fragment, or a homologue or derivative thereof and HIV GAGp6 or GAGp6 fragment, or a homologue or derivative thereof.

Thus, in one embodiment, the screening method includes the steps of contacting the first and second proteins of the protein complexes of the present invention in the presence of one or more test compounds, and detecting the interaction between said first protein and said second protein. Preferably, the first and second proteins are fusion proteins having a detectable tag. The methods can be conducted in a substantially cell free environment or in a host cell, preferably in yeast cells.

In a preferred embodiment, the screening method includes: (a) providing in a host cell a first fusion protein having Tsg101 or Tsg101 fragment, or a homologue or derivative thereof, and a second fusion protein having a retroviral GAG (e.g. HIV GAG) or a GAG fragment, or a homologue or derivative thereof, wherein a DNA binding domain is fused to one of the first and second proteins while a transcription-activating domain is fused to the other of said first and second proteins; (b) providing in said host cell a reporter gene, wherein the transcription of the reporter gene is determined by the interaction between the first protein and the second protein; (c) allowing said first and second fusion proteins to interact with each other within said host cell in the presence of a test compound; and (d) determining the presence or absence of expression of said reporter gene.

In accordance with another aspect of the present invention, host cells are provided. In one embodiment, isolated non-human host cells or human host cells are provided expressing Tsg101 or a fragment thereof and HIV GAG or a fragment thereof. Preferably, the host cells comprise:

(a) a first expression cassette having a promoter operably linked to a nucleic acid encoding a first protein, said first protein being selected from group consisting of
  (i) Tsg101 protein,
  (ii) a Tsg101 protein homologue having an amino acid sequence at least 50%, 60%, 70%, 80%, or 90% identical to that of Tsg101 and capable of interacting with HIV GAGp6,
  (iii) a Tsg101 protein fragment containing the Tsg101 UEV domain or a homologue thereof having at least 50%, 60%, 70%, 80%, or 90% identical to the Tsg101 fragment, said fragment and homologue being capable of interacting with HIV GAGp6, and
  (iv) a fusion protein containing said Tsg101 protein, said Tsg101 protein homologue or said Tsg101 protein fragment; and (b) a second expression cassette having a promoter operably linked to a nucleic acid encoding a second protein selected from the group consisting of
  (1) a retrovirus GAG polypeptide having the P(T/S)AP (SEQ ID NO:1 or SEQ ID NO:3) late domain motif,
  (2) a homologue of said retrovirus GAG polypeptide, said homologue having an amino acid sequence at least 50%, 60%, 70%, 80%, or 90% identical to that of said retrovirus GAG polypeptide and capable of interacting with Tsg101,
  (3) a fragment of said retrovirus GAG polypeptide, or a homologue having an amino acid sequence at least 50%, 60%, 70%, 80%, or 90% identical to that of said fragment, said fragment and homologue thereof being capable of interacting with Tsg101 through UEV domain, and
  (4) a fusion protein containing said retrovirus GAG polypeptide, said retrovirus GAG polypeptide homologue or said retrovirus GAG polypeptide fragment or homologue thereof.

In preferred embodiments, the promoters in the expression cassettes are chimeric.

In a preferred embodiment, the second protein is selected from the group consisting of
  (1) HIV GAG polypeptide,
  (2) a HIV GAG polypeptide homologue having an amino acid sequence at least 50%, 60%, 70%, 80%, or 90% identical to that of HIV GAG polypeptide and capable of interacting with Tsg101,
  (3) HIV GAGp6 protein,
  (4) a HIV GAGp6 homologue having an amino acid sequence at least 50%, 60%, 70%, 80%, or 90% identical to that of HIV GAGp6 polypeptide and capable of interacting with Tsg101, (5) a HIV GAGp6 fragment or a homologue thereof having an amino acid sequence at least 50%, 60%, 70%, 80%, or 90% identical to that of said fragment, said fragment and homologue are capable of interacting with Tsg101, and
(6) a fusion protein containing said HIV GAG polypeptide, said HIV GAG polypeptide homologue, said HIV GAGp6 protein, said HIV GAGp6 homologue or said HIV GAGp6 fragment or homologue thereof.

In another preferred embodiment of the host cell of the present invention, one of said first and second nucleic acids is linked to a nucleic acid encoding a DNA binding domain, and the other of said first and second nucleic acids is linked to a nucleic acid encoding a transcription-activation domain, whereby two fusion proteins can be produced in said host cell. Preferably, the host cell further comprises a reporter gene, wherein the expression of the reporter gene is determined by the interaction between the first protein and the second protein.

The present invention further relates to a method for providing a compound capable of interfering with an interaction between the first and second proteins in the protein complexes of the present invention, which comprises the steps of providing atomic coordinates defining a three-dimensional structure of a protein complex, and designing or selecting compounds capable of interfering with the interaction between said first protein and said second protein based on said atomic coordinates.

In addition, the present invention also provides a method for selecting a compound capable of inhibiting Tsg101 or capable of inhibiting a protein-protein interaction between Tsg101 and HIV GAGp6, which comprises:
contacting a test compound with a protein selected from group consisting of
(i) Tsg101 protein,
(ii) a Tsg101 protein homologue having an amino acid sequence at least 50%, 60%, 70%, 80%, or 90% identical to that of Tsg101 and capable of interacting with HIV GAGp6,
(iii) a Tsg101 protein fragment containing the Tsg101 UEV domain or a homologue thereof having at least 50%, 60%, 70%, 80%, or 90% identical to the Tsg101 fragment, said fragment and homologue being capable of interacting with HIV GAGp6, and
(iv) a fusion protein containing said Tsg101 protein, said Tsg101 protein homologue or said Tsg101 protein fragment or homologue thereof; and
determining whether said test compound is capable of binding said protein. In a preferred embodiment, the method further includes testing a selected test compound capable of binding said protein for its ability to interfere with a protein-protein interaction between Tsg101 and HIV GAGp6, and optionally further testing a selected test compound capable of binding said protein for its ability to suppress viral maturation or release or inhibit HIV viral budding from an HIV-infected host cell.

The present invention further provides a method for selecting a compound capable of inhibiting a protein-protein interaction between Tsg101 and a retroviral GAG containing a P(T/S)AP (SEQ ID NO:1 or SEQ ID NO:3) motif. The method comprises (a) providing atomic coordinates defining a three-dimensional structure of a protein selected from group consisting of (i) Tsg101 protein, (ii) a Tsg101 protein homologue having an amino acid sequence at least 90% identical to that of Tsg101 and capable of interacting with HIV GAGp6, (iii) a Tsg101 protein fragment containing the Tsg101 UEV domain, and (iv) a fusion protein containing said Tsg101 protein, said Tsg101 protein homologue or said Tsg101 protein fragment; and (b) designing or selecting compounds capable of interacting with said protein based on said atomic coordinates. In a preferred embodiment, the method further includes a step of testing a selected compound capable of interacting with said protein for its ability to interfere with a protein-protein interaction between Tsg101 and the retroviral GAG, particularly HIV GAGp6, and optionally a step of testing a selected test compound capable of interacting with said protein for its ability to inhibit viral budding, particularly HIV viral budding from an HIV-infected host cell.

The present invention also provides methods for modulating, in mammalian cells, a protein complex comprising Tsg101 and a retroviral GAG containing a P(T/S)AP (SEQ ID NO:1 or SEQ ID NO:3) late domain motif. In a specific embodiment, the retroviral GAG is HIV GAG. The methods can be used to inhibit viral budding, particularly HIV viral budding from infected host cells. Inhibition of viral budding prevents the viruses from being released from the infected host cells thereby suppressing further viral propagation. Accordingly, the present invention also encompasses methods of treating viral infection, particularly HIV infection, and methods of treating and preventing AIDS in patients.

In one embodiment, the concentration of a protein complex having Tsg101 interacting with the retroviral GAG is reduced in cells. Various methods can be employed to reduce the concentration of the protein complex. The protein complex concentration can be reduced by interfering with the interaction between Tsg101 and the retroviral GAG (e.g., HIV GAG). For example, compounds capable of interfering with interactions between Tsg101 and HIV GAG can be administered to cells in vitro or in vivo in a patient. Such compounds can be small organic molecules capable of binding Tsg101 protein, particularly the UEV domain of Tsg101 protein, or HIV GAGp6. They can also be antibodies immunoreactive with the Tsg101 protein or HIV GAGp6. Preferably, antibodies that bind to the UEV domain of the Tsg101 protein are used. Also, the compounds can be small peptides derived from the HIV GAGp6 protein or mimetics thereof capable of binding Tsg101, or small peptides derived from the Tsg101 protein or mimetics thereof capable of binding HIV GAGp6.

In another embodiment, the methods include inhibiting the expression of the Tsg101 protein and/or HIV GAG protein. The inhibition can be at the transcriptional, translational, or post-translational level. For example, antisense compounds and ribozyme compounds can be administered to human cells in vitro or in human bodies.

In yet another embodiment, an antibody selectively immunoreactive with a protein complex having Tsg101 interacting with the retroviral GAG (e.g., HIV GAG) is administered to cells in vitro or in human bodies to inhibit the protein complex activities and/or reduce the concentration of the protein complex in the cells or patient.

The present invention provides a method for treating HIV infection and AIDS that is distinct from the therapeutic approaches heretofore known the in the art. The method is targeted at a cellular protein of the host cells as well as its interaction with a viral protein. The interaction is required for HIV budding from the infected host cells. Accordingly, it is less likely that HIV will develop viral resistance to the treatment according to the present invention.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

BRIEF DESCRIPTION OF THE DRAWINGS

FIG. 5 illustrates several examples of siRNA duplexes targeting Tsg101 transcript; and FIG. 6 shows examples of shRNA targeting Tsg101 transcript.

DETAILED DESCRIPTION OF THE INVENTION

1. Definitions

Figure 1:
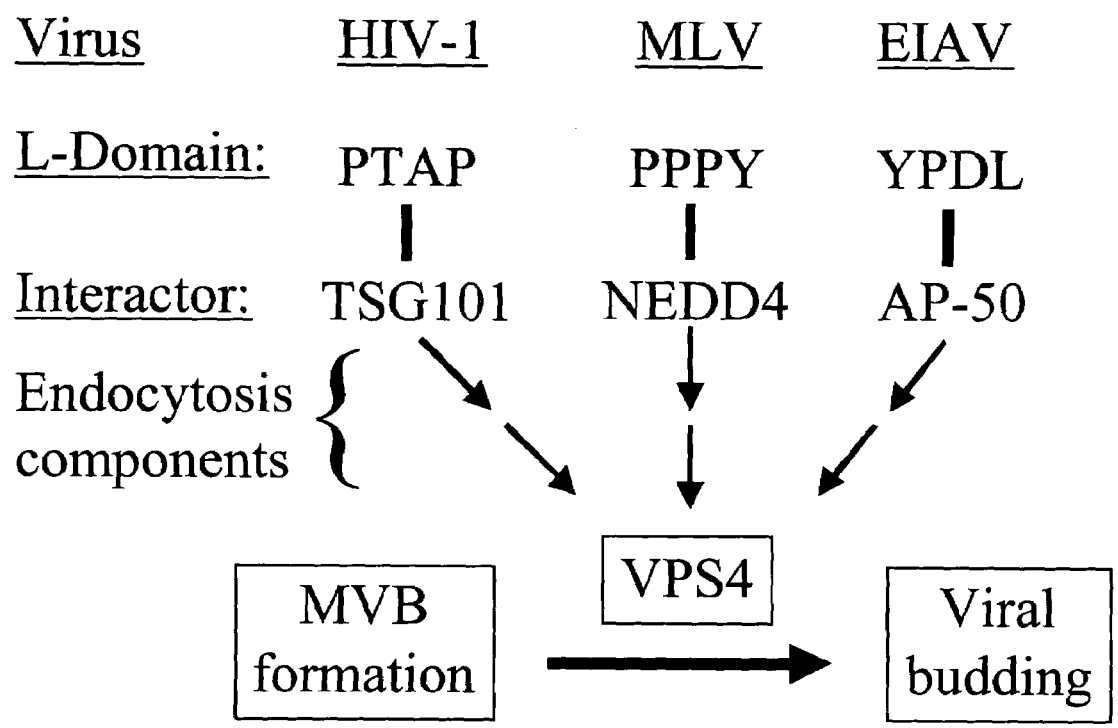
FIG. 1 is a diagram summarizing the proposed pathways for the budding by viruses using different late domain motifs.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

The term "protein fragment" as used herein means a polypeptide that represents a portion of a protein. When a protein fragment exhibits interactions with another protein or protein fragment, the two entities are said to interact through interaction domains that are contained within the entities.

As used herein, the term "interacting" or "interaction" means that two protein domains, fragments or complete proteins exhibit sufficient physical affinity to each other so as to bring the two "interacting" protein domains or proteins physically close to each other. An extreme case of interaction is the formation of a chemical bond that results in continual and stable proximity of the two domains. Interactions that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, van der Waals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include specific interactions between antigen and antibody, ligand and receptor, enzyme and substrate, and the like.

Two protein domains, fragments or complete proteins are said to "interact" with each other when an interaction is detected by either a standard yeast two-hybrid assay or a co-immunoprecipitation assay. The binding constant for two interacting proteins, which reflects the strength or quality of the interaction, can also be determined using methods known in the art. See Phizicky and Fields, *Microbiol. Rev.*, 59:94-123 (1995).

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

As used herein, the term "protein complex" means a composite unit that is a combination of two or more proteins formed by interaction between the proteins. Typically but not necessarily, a "protein complex" is formed by the binding of two or more proteins together through specific non-covalent binding affinities. However, covalent bonds may also be present between the interacting partners. For instance, the two interacting partners can be covalently crosslinked so that the protein complex becomes more stable.

The term "isolated protein complex" means a protein complex present in a composition or environment that is different from that found in nature in its native or original cellular or body environment. In preferred embodiments, an "isolated protein complex" is separated from at least 50%, more preferably at least 75%, most preferably at least 90% of other naturally co-existing cellular or tissue components. Thus, an "isolated protein complex" may also be a naturally existing protein complex in an artificial preparation or a non-native host cell. An "isolated protein complex" may also be a "purified protein complex", that is, a substantially purified form in a substantially homogenous preparation substantially free of other cellular components, other polypeptides, viral materials, or culture medium, or when the protein components in the protein complex are chemically synthesized, chemical precursors or by-products associated with the chemical synthesis. In preferred embodiments, a "purified protein complex" is a preparation containing a particular protein complex in an amount that is preferably at least 10%, more preferably at least 20%, and most preferably at least 50% of the total protein content. A "purified protein complex" may be obtained from natural or recombinant host cells or other body samples by standard purification techniques, or by chemical synthesis.

The terms "hybrid protein," "hybrid polypeptide," "hybrid peptide," "fusion protein," "fusion polypeptide," and "fusion peptide" are used herein interchangeably to mean a non-naturally occurring protein having a specified polypeptide molecule covalently linked to one or more polypeptide molecules which do not naturally link to the specified polypeptide. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

As used herein, the term "homologue," when used in connection with a first native protein or fragment thereof that is discovered, according to the present invention, to interact with a second native protein or fragment thereof, means a polypeptide that exhibits a sufficient amino acid sequence homology (typically at least 50%) to the first native interacting protein, or to one of the interacting domains of the first native protein and is capable of interacting with the second native protein. Typically, a protein homologue of a native protein may have an amino acid sequence that is at least 60%, 65%, or 70%, preferably at least 75%, more preferably at least 80%, 85%, 86%, 87%, 88% or 89%, even more preferably at least 90%, 91%, 92%, 93% or 94%, and most preferably 95%, 96%, 97%, 98% or 99% identical to the native protein. Examples of homologues may be the ortholog proteins found in other species including animals, plants, yeast, bacteria, and the like. Homologues may also be selected by, e.g., mutagenesis in a native protein. For example, homologues may be identified by site-specific mutagenesis in combination with assays for detecting protein-protein interactions, e.g., the yeast two-hybrid system described below, as will be apparent to skilled artisans apprised of the present invention.

For purposes of comparing two different nucleic acid or polypeptide sequences, one sequence (test sequence) may be described to be a specific "percent identical to" another sequence (reference sequence) in the present disclosure. In this respect, when the length of the test sequence is less than 90% of the length of the reference sequence, the percentage identity is determined by the algorithm of Myers and Miller, *Bull. Math. Biol.*, 51:5-37 (1989) and Myers and Miller, *Comput. Appl. Biosci.*, 4(1):11-7 (1988). Specifically, the identity is determined by the ALIGN program, which is available at http://www2.igh.cnrs.fr maintained by IGH, Montpellier, FRANCE. Typically the default parameters should be used. A modified form of the ALIGN program may also be used.

Where the length of the test sequence is at least 90% of the length of the reference sequence, the percentage identity is determined by the algorithm of Karlin and Altschul, *Proc. Natl. Acad. Sci. USA*, 90:5873-77 (1993), which is incorporated into the various BLAST programs. Specifically, the percentage identity is determined by the "BLAST 2 Sequences" tool, which is available at http://www.ncbi.nlm.nih.gov/gorf/b12.html. See Tatusova and Madden, *FEMS Microbiol. Lett.*, 174(2):247-50 (1999). For pairwise DNA-DNA comparison, the BLASTN 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter).

The term "antibody" as used herein encompasses both monoclonal and polyclonal antibodies that fall within any antibody classes, e.g., IgG, IgM, IgA, or derivatives thereof. The term "antibody" also includes antibody fragments including, but not limited to, Fab, F(ab')$_2$, and conjugates of such fragments, and single-chain antibodies comprising an antigen recognition epitope. In addition, the term "antibody" also means humanized antibodies, including partially or fully humanized antibodies. An antibody may be obtained from an animal, or from a hybridoma cell line producing a monoclonal antibody, or obtained from cells or libraries recombinantly expressing a gene encoding a particular antibody.

The term "selectively immunoreactive" as used herein means that an antibody is reactive thus binds to a specific protein or protein complex, but not other similar proteins or fragments or components thereof.

The term "compound" as used herein encompasses all types of organic or inorganic molecules, including but not limited proteins, peptides, polysaccharides, lipids, nucleic acids, small organic molecules, inorganic compounds, and derivatives thereof.

Unless otherwise specified, the term "Tsg101" as used herein means human Tsg101 protein. Unless otherwise specified, the term "HIV GAG" as used herein means HIV GAG protein. Unless otherwise specified, the term "HIV GAGp6" as used herein means HIV GAGp6 protein.

As used herein, the term "HIV infection" generally encompasses infection of a host animal, particularly a human host, by the human immunodeficiency virus (HIV) family of retroviruses including, but not limited to, HIV I, HIV II, HIV III, and the like. Thus, treating HIV infection will encompass the treatment of a person who is a carrier of any of the HIV family of retroviruses or a person who is diagnosed of active AIDS, as well as the treatment or prophylaxis of the AIDS-related conditions in such persons. A carrier of HIV may be identified by any methods known in the art. For example, a person can be identified as a HIV carrier on the basis that the person is anti-HIV antibody positive, or is HIV-positive, or has symptoms of AIDS. That is, "treating HIV infection" should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating $CD^{4+}$ T cells), and AIDS (which is defined by more serious AIDS-defining illnesses and/or a decline in the circulating CD4 cell count to below a level that is compatible with effective immune function). In addition, "treating or preventing HIV infection" will also encompass treating suspected infection by HIV after suspected past exposure to HIV by e.g., blood transfusion, exchange of body fluids, bites, accidental needle stick, or exposure to patient blood during surgery.

The term "treating AIDS" means treating a patient who exhibits more serious AIDS-defining illnesses and/or a decline in the circulating CD4 cell count to below a level that is compatible with effective immune function. The term "treating AIDS" also encompasses treating AIDS-related conditions, which means disorders and diseases incidental to or associated with AIDS or HIV infection such as AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia purpurea and associated opportunistic infections such as *Pneumocystis carinii* pneumonia, Mycobacterial tuberculosis, esophageal candidiasis, toxoplasmosis of the brain, CMV retinitis, HIV-related encephalopathy, HIV-related wasting syndrome, etc.

Thus, the term "preventing AIDS" as used herein means preventing in a patient who has HIV infection or is suspected to have HIV infection or is at risk of HIV infection from developing AIDS (which is characterized by more serious AIDS-defining illnesses and/or a decline in the circulating CD4 cell count to below a level that is compatible with effective immune function) and/or AIDS-related conditions.

2. Protein Complexes

Novel protein-protein interactions have been discovered and confirmed using yeast two-hybrid systems. In particular, it has been discovered that Tsg101 interacts with HIV GAG in the p6 domain through the late domain motif therein. Binding regions of Tsg101 and HIV GAGp6 discovered in yeast two-hybrid systems are summarized in Table 1. The GenBank accession numbers for the gene sequences and amino acid sequences of Tsg101 and HIV GAGp6 are noted in Table 1 below.

TABLE 1

Binding Regions of HIV Gag and Tsg101

| Bait | | | Prey | | |
|---|---|---|---|---|---|
| | AA Coordinates | | | AA Coordinates | |
| Bait Protein | Start | End | Prey Protein | Start | End |
| HIV Gag (GenBank Accession No. AF324493) | 449 | 500 | Tumor Susceptibility Gene 101 (Tsg101) (GenBank Accession No. U82130) | 7 | 390 |

2.1. Tsg101 is Involved in HIV Viral Budding

Tumor susceptibility gene 101 (Tsg101) was originally identified as a 381 amino acid polypeptide involved in tumorigenesis. Tsg101 can be localized in the nucleus and in the cytoplasm depending on the stage of cell cycle. Tsg101 interacts with stathmin, a cytosolic phosphoprotein implicated in tumorigenesis, and overexpression of a Tsg101 anti-sense transcript in NIH-3T3 cells results in transformation of the cells. See Li and Cohen, *Cell*, 85(3):319-29 (1996). Furthermore, it has been suggested that defects in Tsg101 may occur during breast cancer tumorigenesis and/or progression. Li et al., *Cell*, 88(1):143-54 (1997). Tsg101 contains a ubiquitin-conjugating enzyme E2 catalytic domain. Recently, interest has focused on Tsg101 as a possible component of the ubiquitin/proteasome degradation pathway. By database search and comparison, it has been found that that N-terminal Tsg101 contains a domain related to E2 ubiquitin-conjugating (Ubc) enzymes although lacking the active site cysteine. See Koonin and Abagyan, *Nat. Genet.*, 16(4):330-1 (1997). Thus, Tsg101 may belong to a group of apparently inactive homologs of Ubc enzymes. See id. The domain related to E2 ubiquitin-conjugating (Ubc) enzymes is referred to ubiquitin E2 variant (UEV) domain. The Tsg101 UEV domain includes, approximately, amino acid residues 2 to 145.

In accordance with the present invention, a yeast two-hybrid search of a human spleen cDNA library with GAG polyprotein (aa 449-500, p6 domain, or "GAGp6") of HIV-1 isolated the tumor susceptibility TSG 101 protein (Tsg101; aa 7-390) as an interactor. The GAGp6 bait used here contains a late domain motif (—PTAP—) (SEQ ID NO:1). The GAG polyprotein of retroviruses gives rise to a set of mature proteins (matrix, capsid, and nucleocapsid) that produce the inner virion core. In addition, GAG also contains a C-terminal portion called p6. In the case of HIV-1, GAGp6 contains a sequence called the late domain, so-called because it is required for a late stage of HIV viral budding from the host cell surface. The late domain has a functional relationship with ubiquitin, in that the late domain is required in viral budding, and depletion of the intracellular pool of free ubiquitin produces a similar late phenotype. Patnaik et al., *Proc. Natl. Acad. Sci. USA*, 97(24):13069-74 (2000); Schubert et al., *Proc. Natl. Acad. Sci. USA*, 97(24):13057-62 (2000); Strack et al., *Proc. Natl. Acad. Sci. USA*, 97(24):13063-8 (2000). The late domain is thought to represent a docking site for the ubiquitination machinery.

As is known in the art, the P(T/S)AP (SEQ ID NO:1 or SEQ ID NO:3) motif is conserved among the GAGp6 domains of all known primate lentiviruses. In nonprimate lentiviruses, which lack a GAGp6 domain, the P(T/S)AP (SEQ ID NO:1 or SEQ ID NO:3) motif is at the immediate C terminus of the GAG polyprotein. It has been shown that the P(T/S)AP (SEQ ID NO:1 or SEQ ID NO:3) motif is required for a late stage of viral budding from the host cell surface. It is critical for lentivirus' and particularly HIV's particle production. See Huang et al., *J. Virol.*, 69:6810-6818 (1995). Specifically, deletion of the PTAP (SEQ ID NO:1) motif results in drastic reduction of viral particle production. In addition, the PTAP (SEQ ID NO:1)-deficient viruses proceeded through the typical stages of morphogenesis but failed to complete the process. Rather, they remain tethered to the plasma membrane and are thus rendered non-infectious. That is, the viral budding process is stalled. See Huang et al., *J. Virol.*, 69:6810-6818 (1995).

In accordance with the present invention, different GAGp6 point mutants (E6G, P7L, A9R, or P10L) were generated and tested for their ability to bind Tsg101 protein. See Example 3 below. While the wild-type GAGp6 peptide and the E6G GAGp6 mutant were capable of binding Tsg101 protein, each of the P7L, A9R, and P10L point mutations abolishes the GAGp6 binding affinity to Tsg101. The P7L, A9R, and P10L point mutations alter the PTAP (SEQ ID NO:1) motif in GAGp6 peptide. The same mutations in the PTAP (SEQ ID NO:1) motif of the HIV GAGp6 gag protein prevent HIV particles from budding from the host cells. See Huang et al., *J. Virol.*, 69:6810-6818 (1995). Further, as shown in Example 4 below, the inventors of the present invention discovered that the first 14 amino acid residues of HIV GAGp6 (which includes the PTAP (SEQ ID NO:1) late domain motif) are sufficient in binding to the N-terminal portion of Tsg101 (amino acid residues 1-207, which includes the Tsg101 UEV domain).

Tsg101 is intimately involved in endocytosis, intracellular vesicle trafficking, and vacuolar protein sorting (VPS). The VPS pathway sorts membrane-bound proteins for eventual degradation in the lysosome (vacuole in yeast). See Lemmon and Traub, *Curr. Opin. Cell. Biol.*, 12:457-66 (2000). Two alternative entrees into the VPS pathway are via vesicular trafficking from the Golgi (e.g., in degrading misfolded membrane proteins) or via endocytosis from the plasma membrane (e.g., in downregulating surface proteins like epidermal growth factor receptor (EGFR)). Vesicles carrying proteins from either source can enter the VPS pathway by fusing with endosomes. As these endosomes mature, their cargos are sorted for lysosomal degradation via the formation of structures called multivesicular bodies (MVB). MVB are created when surface patches on late endosomes bud into the compartment, forming small (~50-100 nm) vesicles. A maturing MVB can contain tens or even hundreds of these vesicles. The MVB then fuses with the lysosome, releasing the vesicles for degradation in this hydrolytic organelle.

The Tsg101 prey fragment isolated in yeast two-hybrid assay contains the ubiquitin E2 variant (UEV) domain indicating that the UEV domain is involved in the binding to the P(T/S)AP (SEQ ID NO:1 or SEQ ID NO:3) domain. The involvement of the Tsg101 UEV domain is consistent with the fact that ubiquitin is required for retrovirus budding and that proteasome inhibition reduces the level of free ubiquitin in HIV-1-infected cells and interferes with the release and maturation of HIV-1 and HIV-2. See Patnaik et al., *Proc. Natl. Acad. Sci. USA*, 97(24):13069-74 (2000); Schubert et al., *Proc. Natl. Acad. Sci. USA*, 97(24):13057-62 (2000); Strack et al., *Proc. Natl. Acad. Sci. USA*, 97(24):13063-8 (2000).

It is known that short chains of Ub (1-3 molecules) can "mark" surface receptors for endocytosis and degradation in the lysosome. Hicke, *Trends Cell Biol.*, 9:107-112 (1999); Rotin et al., *J. Membr. Biol.*, 176:1-17 (2000). Several classes of proteins that carry the P(T/S)AP (SEQ ID NO:1 or SEQ ID NO:3) motif are surface receptors known to be degraded via the VPS pathway or function in the VPS pathway. See Farr et al., *Biochem. J.*, 345(3):503-509 (2000); Staub and Rotin., *Structure*, 4:495-499 (1996). Although it is not known whether Tsg101 lacks ubiquitin ligase activity, it is believed, based on the large number of Tsg101 interactors discovered in accordance with the present invention, that a plausible role for Tsg101 in the VPS pathway is to recognize ubiquitinated proteins that carry P(T/S)AP (SEQ ID NO:1 or SEQ ID NO:3) motifs and help coordinate their incorporation into vesicles that bud into the MVB.

This is especially intriguing because the formation of MVB is the only known cellular process in which cell buds a vesicle out of the cytoplasm into another compartment. This budding is topologically equivalent to viral budding in which viruses bud out of the cytoplasm at the plasma membrane into excellular space. Accordingly, while not wishing to be bound by any theory, it is believed that the binding of the P(T/S)AP (SEQ ID NO:1 or SEQ ID NO:3) motif in lentivirus GAG polyproteins to the cellular protein Tsg101 enables lentiviruses having the P(T/S)AP (SEQ ID NO:1 or SEQ ID NO:3) motif to usurp cellular machinery normally used for MVB formation to allow viral budding from the plasma membrane. It is also believed that depletion of Tsg101 or interfering with the interaction between Tsg101 and the P(T/S)AP (SEQ ID NO:1 or SEQ ID NO:3) motif in lentivirus-infected cells will prevent lentiviral budding from the cells.

In addition, the recruitment of cellular machinery to facilitate virus budding appears to be a general phenomenon, and distinct late domains have been identified in the structural proteins of several other enveloped viruses. See Vogt, *Proc. Natl. Acad. Sci. USA*, 97:12945-12947 (2000). Two well-characterized late domains are the "PY" motif (consensus sequence: PPXY; X=any amino acid) found in membrane-associated proteins from certain enveloped viruses. See Craven et al., *J. Virol.*, 73:3359-3365 (1999); Harty et al., *Proc. Natl. Acad. Sci. USA*, 97:13871-13876 (2000); Harty et al., *J. Virol.*, 73:2921-2929 (1999); and Jayakar et al., *J. Virol.*, 74:9818-9827 (2000). The cellular target for the PY motif is Nedd4, which also contains a Hect ubiquitin E3 ligase domain. The "YL" motif (YXXL) was found in the GAG protein of equine infectious anemia virus (EIAV). Puffer et al., *J. Virol.*, 71:6541-6546 (1997); Puffer et al., *J. Virol.*, 72:10218-10221 (1998). The cellular receptor for the "YL" motif appears to be the AP-50 subunit of AP-2. Puffer et al., *J. Virol.*, 72:10218-10221 (1998). Interestingly, the late domains such as the P(T/S)AP (SEQ ID NO:1 or SEQ ID NO:3) motif, PY motif and the YL motif can still function when moved to different positions within retroviral GAG proteins, which suggests that they are docking sites for cellular factors rather than structural elements. Parent et al., *J. Virol.*, 69:5455-5460 (1995); Yuan et al., *EMBO J.*, 18:4700-4710 (2000). Moreover, the late domains such as the P(T/S)AP (SEQ ID NO:1 or SEQ ID NO:3) motif, PY motif and the YL motif can function interchangeably. That is one late domain motif can be used in place of another late domain motif without affecting viral budding. Parent et al., *J. Virol.*, 69:5455-5460 (1995); Yuan et al., *EMBO J.*, 18:4700-4710 (2000); Strack et al., *Proc. Natl. Acad. Sci. USA*, 97:13063-13068 (2000).

Accordingly, while not wishing to be bound by any theory, it is believed that as shown in FIG. 1, although the three late domain motifs bind to different cellular targets, they utilize common cellular pathways to effect viral budding. In particular, it is believed that the different cellular receptors for viral late domain motifs feed into common downstream steps of the vacuolar protein sorting (VPS) and MVB pathway. As discussed above, Tsg101 functions in the VPS pathway. Another protein, Vps4 functions in Tsg101 cycling and endosomal trafficking. Particularly, Vps4 mutants prevent normal Tsg101 trafficking and induce formation of aberrant, highly vacuolated endosomes that are defective in the sorting and recycling of endocytosed substrates. See Babst et al, *Traffic*, 1:248-258 (2000).

Interestingly, a yeast two-hybrid search of a spleen library with the tumor susceptibility protein Tsg101 also identified an interaction with the growth arrest-specific protein GAS7b. In addition, as disclosed in the commonly assigned U.S. Provisional Application Ser. No. 60/311,528, GAS7b is an interactor of the capsid region of the HIV GAG polyprotein. GAS7b is expressed preferentially in cells that are entering the quiescent state. Inhibition of GAS7b expression in terminally differentiating cultures of embryonic murine cerebellum impedes neurite outgrowth, while overexpression in undifferentiated neuroblastoma cell cultures dramatically promotes neurite-like outgrowth. Ju et al., *Proc Natl Acad Sci* 95(19):11423-8 (1998); Lazakovitch et al., *Genomics* 61(3):298-306 (1999). These findings suggest a role for GAS7b in controlling terminal cellular differentiation, and the domain structure of GAS7b suggests it may do this by regulating the cytoskeleton. In addition, GAS7b also interacts with two different regulators of small GTPases that control the actin cytoskeleton. The interactions of GAS7b with the HIV capsid and with Tsg101 (which in turn interacts with the HIV GAGp6 protein) strongly suggest these proteins form a multimolecular complex involved in the late stages of viral assembly and budding.

2.2. Protein Complexes

As discussed above, the UEV domain of the Tsg101 protein and the PTAP (SEQ ID NO:1) motif of the HIV GAGp6 are responsible for the interactions. In addition, an examination of HIV-1 amino acid sequence variants in GenBank by the inventors using BLAST (Basic Local Alignment Search Tool) identified a number of HIV strains with the standard PTAP (SEQ ID NO:1) motif being replaced with variations of the motif, indicating that such variations can also enable viral budding and that peptides with such variations may also bind Tsg101. Such identified variations include the PSAP (SEQ ID NO:3) motif, the PIAP (SEQ ID NO:5) motif (see Zhang et al., *J. Virol.*, 71:6662-6670 (1997); Farrar et al., *J. Med. Virol.*, 34:104-113

(1991)), and the PTTP motif (SEQ ID NO:2) (see Zhang et al., *J. Virol.*, 71:6662-6670 (1997).

Accordingly, the present invention provides protein complexes formed by interactions between Tsg101 or a homologue thereof and HIV GAG polypeptide or a homologue thereof. The present invention also provides a protein complex having a fragment of Tsg101 or a homologue thereof interacting with HIV GAG polypeptide or a homologue thereof. In addition, the present invention further encompasses a protein complex having Tsg101 or a homologue thereof interacting with a fragment of HIV GAG polypeptide or a homologue thereof. In other words, one or more of the interacting protein members of a protein complex of the present invention may be a native protein or a homologue or derivative of a native protein or a fragment thereof. As defined in Section 1 above, the homologues and derivatives of Tsg101 or fragment thereof should be capable of interacting with HIV GAG (through the GAGp6 region). The HIV GAG or GAG fragment, or homologues and derivatives are those capable of interacting with Tsg101, through the UEV domain. Preferably, the amino acid sequence of a homologue is at least 50%, 60%, 65%, 70%, 75%, 80%, 85%, 90%, or 95% identical to that of its corresponding native protein or protein fragment.

Thus, for example, one interacting partner in the protein complexes can be a complete native Tsg101, a Tsg101 homologue capable of interacting with the HIV GAGp6, a Tsg101 derivative, a derivative of the Tsg101 homologue, a Tsg101 fragment capable of interacting with HIV GAGp6 (e.g., a fragment containing the UEV domain of the Tsg101 protein, specifically the amino acid residues 1-207, the amino acid residues 1-147, etc.), a homologue of the Tsg101 fragment, a derivative of the Tsg101 fragment, or a fusion protein containing (1) complete native Tsg101, (2) a Tsg101 homologue capable of interacting with the HIV GAGp6 or (3) a Tsg101 fragment capable of interacting with HIV GAGp6, or (4) a homologue of a Tsg101 fragment capable of interacting with HIV GAGp6.

The other partner can be (1) an HIV GAG polypeptide, (2) an HIV GAG polypeptide homologue capable of interacting with Tsg101, (3) HIV GAGp6 protein, (4) an HIV GAGp6 homologue capable of interacting with Tsg101, (5) an HIV GAGp6 fragment capable of interacting with Tsg101, (6) a homologue of an HIV GAGp6 fragment capable of interacting with Tsg101, or (7) a fusion protein containing an HIV GAG polypeptide, an HIV GAG polypeptide homologue, HIV GAGp6, an HIV GAGp6 homologue, or an HIV GAGp6 fragment or a homologue thereof.

GAG polypeptides and fragments thereof from other retroviruses containing the P(T/S/I)(A/T)P (SEQ ID NOs: 1-6) late domain motif can also interact with Tsg101 in the same manner as the HIV GAG polypeptide. Thus, they can be used in forming protein complexes with Tsg101 or Tsg101 fragment, or a homologue or derivative thereof. Preferably, GAG polypeptides or fragments thereof of lentiviruses containing the P(T/S)AP (SEQ ID NO:1 or SEQ ID NO:3) late domain are used to form protein complexes. Such GAG polypeptides or fragments thereof may be from a non-primate lentiviruses including bovine lentiviruses (e.g. bovine immunodeficiency virus (BIV), Jembrana disease virus), feline lentiviruses (e.g. feline immunodeficiency virus (FIV) which causes immunodeficiency, wasting, and encephalitis in cats), and ovine/caprine lentivirus (e.g. caprine arthritis-encephalitis virus (CAEV) which causes anemia and wasting in goats, ovine lentivirus, Visna virus which causes pneumonia, wasting, encephalitis and arthritis). Preferably, the GAG polypeptides or fragments thereof are from primate lentiviruses including, but not limited to, human immunodeficiency virus type 1 (HIV-1), human immunodeficiency virus type 2 (HIV-2), human immunodeficiency virus type 3 (HIV-3) (all of which cause AIDS), and various simian immunodeficiency viruses that infect hosts such as chimpanzee, mangabey, African Green monkey, mandrill, L'Hoest, Sykes' monkey, or Guereza Colobus monkey.

Besides the native retroviral GAG polypeptides, useful interacting partners for Tsg101 or a Tsg101 fragment, or a homologue or derivative thereof also include homologues of the native retroviral GAG polypeptides capable of interacting with Tsg101, derivatives of the native or homologue GAG polypeptides capable of interacting with Tsg101, fragments of the GAG polypeptides capable of interacting with Tsg101 (e.g., a fragment containing the P(T/S)AP (SEQ ID NO:1 or SEQ ID NO:3) motif), derivatives of the GAG polypeptide fragments, or fusion proteins containing (1) a complete GAG polypeptide, (2) a GAG polypeptide homologue capable of interacting with Tsg101 or (3) a GAG polypeptide fragment capable of interacting with Tsg101.

Tsg101 fragments capable of interacting with HIV GAGp6 can be the combination of molecular engineering of a Tsg101-encoding nucleic acid and a method for testing protein-protein interaction. For example, the coordinates in Table 1 can be used as starting points and various Tsg101 fragments falling within the coordinates can be generated by deletions from either or both ends of the coordinates. The resulting fragments can be tested for their ability to interact with HIV GAGp6 using any methods known in the art for detecting protein-protein interactions (e.g., yeast two-hybrid method). Likewise, HIV GAG fragments, HIV GAGp6 fragments and other retroviral GAG polypeptide fragments capable of interacting with Tsg101 can also be identified in a similar manner.

In specific embodiments, the protein complex of the present invention contains a polypeptide that contains a contiguous span of at least 7, 8, 9, 10, 11, 12, 13, 14, 15, 20, 25, 30, 35, 40, 50 or more amino acid residues of a naturally occurring HIV GAG sequence. Preferably, the polypeptide contains a contiguous span of between 7 and 20, or 30 or 50 amino acid residues of a naturally occurring HIV GAG sequence. The contiguous span should span the HIV late domain motif which can be the P(T/S)AP (SEQ ID NO:1 or SEQ ID NO:3) motif or a variation thereof (e.g., the PIAP (SEQ ID NO:5) motif and the PTTP (SEQ ID NO:2) motif). Preferably, the late domain motif in the contiguous span is the P(T/S)AP (SEQ ID NO:1 or SEQ ID NO:3) motif. In other specific embodiments, the protein complex contains a polypeptide that contains a contiguous span of at least 8, 9, 10, 11, 12, 13, 14, 15, 20, 25, 30, 35, 40, 50 or more amino acid residues, preferably from 7, 8, or 9 to about 20, 30 or 50 amino acid residues, of a naturally occurring GAG polypeptide sequence from other retroviruses containing a P(T/S)AP (SEQ ID NO:1 or SEQ ID NO:3) late domain motif. The contiguous span should span the retrovirus late domain motif. In preferred embodiments, such other retroviruses are primate lentiviruses or non-primate lentiviruses (except for EIAV). In specific embodiments, the protein complex of the present invention includes a polypeptide having an amino acid sequence selected from the group of EPTAP (SEQ ID NO:7), EPSAP (SEQ ID NO:8), PTAPP (SEQ ID NO:9), PSAPP (SEQ ID NO:10), EPTAPP (SEQ ID NO:11), EPSAPP (SEQ ID NO:12), PEPTAP (SEQ ID NO:13), PEPSAP (SEQ ID NO:14), RPEPTAP (SEQ ID NO:15), RPEPSAP (SEQ ID NO:16), PEPTAPP (SEQ ID NO:17), PEPSAPP (SEQ ID NO:18), EPTAPPEE (SEQ ID NO:19), EPSAPPEE (SEQ ID NO:20), EPTAPPAE (SEQ ID NO:21), PEPTAPPEE (SEQ ID NO:22), PEPTAPPAE (SEQ ID NO:23), PEPSAPPEE (SEQ ID NO:24), RPEPTAPPEE (SEQ ID NO:25), RPEPSAPPEE (SEQ ID NO:26), RPEPTAPPAE (SEQ ID NO:27), RPEPSAPPAE (SEQ ID NO:28), LQSRPEPTAPPEE (SEQ ID NO:29), LQSRPEPSAPPEE (SEQ ID NO:30), LQSRPEPTAPPEES (SEQ ID NO:31), and LQSRPEPSAPPEES (SEQ ID NO:32).

Furthermore, it is believed that the P(T/S)AP (SEQ ID NO:1 or SEQ ID NO:3) or PIAP (SEQ ID NO:5) or PTTP (SEQ ID NO:2) motif itself may be sufficient for Tsg101 binding. Accordingly, a protein complex is also provided containing Tsg101 protein or a homologue or derivative or fragment thereof interacting with a polypeptide consisting essentially the P(T/S)AP (SEQ ID NO:1 or SEQ ID NO:3) or PIAP (SEQ ID NO:5) or PTTP (SEQ ID NO:2) motif, i.e., a polypeptide having the P(T/S)AP (SEQ ID NO:1 or SEQ ID NO:3) or PIAP (SEQ ID NO:5) or PTTP (SEQ ID NO:2) motif and a few flanking amino acids.

In a specific embodiment of the protein complex of the present invention, two or more interacting partners (Tsg101 and HIV GAGp6, or homologues, derivatives or fragments thereof) are directly fused together, or covalently linked together through a peptide linker, forming a hybrid protein having a single unbranched polypeptide chain. Thus, the protein complex may be formed by "intramolecular" interactions between two portions of the hybrid protein. Again, one or both of the fused or linked interacting partners in this protein complex may be a native protein or a homologue, derivative or fragment of a native protein.

The protein complexes of the present invention can also be in a modified form. For example, an antibody selectively immunoreactive with the protein complex can be bound to the protein complex. In another example, a non-antibody modulator capable of enhancing the interaction between the interacting partners in the protein complex may be included. Alternatively, the protein members in the protein complex may be cross-linked for purposes of stabilization. Various crosslinking methods may be used. For example, a bifunctional reagent in the form of R—S—S—R' may be used in which the R and R' groups can react with certain amino acid side chains in the protein complex forming covalent linkages. See e.g., Traut et al., in Creighton ed., *Protein Function: A Practical Approach*, IRL Press, Oxford, 1989; Baird et al., *J. Biol. Chem.*, 251:6953-6962 (1976). Other useful crosslinking agents include, e.g., Denny-Jaffee reagent, a heterbiofunctional photoactivable moiety cleavable through an azo linkage (See Denny et al., *Proc. Natl. Acad. Sci. USA*, 81:5286-5290 (1984)), and $^{125}$I-{S-[N-(3-iodo-4-azidosalicyl)cysteaminyl]-2-thiopyridine}, a cysteine-specific photocrosslinking reagent (see Chen et al., *Science*, 265:90-92 (1994)).

The above-described protein complexes may further include any additional components e.g., other proteins, nucleic acids, lipid molecules, monosaccharides or polysaccharides, ions or other molecules.

2.3. Methods of Preparing Protein Complexes

The protein complex of the present invention can be prepared by a variety of methods. Specifically, a protein complex can be isolated directly from an animal tissue sample, preferably a human tissue sample containing the protein complex. Alternatively, a protein complex can be purified from host cells that recombinantly express the members of the protein complex. As will be apparent to a skilled artisan, a protein complex can be prepared from a tissue sample or recombinant host cell by coimmunoprecipitation using an antibody immunoreactive with an interacting protein partner, or preferably an antibody selectively immunoreactive with the protein complex as will be discussed in detail below. The antibodies can be monoclonal or polyclonal. Coimmunoprecipitation is a commonly used method in the art for isolating or detecting bound proteins. In this procedure, generally a serum sample or tissue or cell lysate is admixed with a suitable antibody. The protein complex bound to the antibody is precipitated and washed. The bound protein complexes are then eluted.

Alternatively, immunoaffinity chromatography and immunoblotting techniques may also be used in isolating the protein complexes from native tissue samples or recombinant host cells using an antibody immunoreactive with an interacting protein partner, or preferably an antibody selectively immunoreactive with the protein complex. For example, in protein immunoaffinity chromatography, the antibody may be covalently or non-covalently coupled to a matrix such as Sepharose in, e.g., a column. The tissue sample or cell lysate from the recombinant cells can then be contacted with the antibody on the matrix. The column is then washed with a low-salt solution to wash off the unbound components. The protein complexes that are retained in the column can be then eluted from the column using a high-salt solution, a competitive antigen of the antibody, a chaotropic solvent, or sodium dodecyl sulfate (SDS), or the like. In immunoblotting, crude proteins samples from a tissue sample or recombinant host cell lysate can be fractionated on a polyacrylamide gel electrophoresis (PAGE) and then transferred to, e.g., a nitrocellulose membrane. The location of the protein complex on the membrane may be identified using a specific antibody, and the protein complex is subsequently isolated.

In another embodiment, individual interacting protein partners may be isolated or purified independently from tissue samples or recombinant host cells using similar methods as described above. The individual interacting protein partners are then contacted with each other under conditions conducive to the interaction therebetween thus forming a protein complex of the present invention. It is noted that different protein-protein interactions may require different conditions. As a starting point, for example, a buffer having 20 mM Tris-HCl, pH 7.0 and 500 mM NaCl may be used. Several different parameters may be varied, including temperature, pH, salt concentration, reducing agent, and the like. Some minor degree of experimentation may be required to determine the optimum incubation condition, this being well within the capability of one skilled in the art once apprised of the present disclosure.

In yet another embodiment, the protein complex of the present invention may be prepared from tissue samples or recombinant host cells or other suitable sources by protein affinity chromatography or affinity blotting. That is, one of the interacting protein partners is used to isolate the other interacting protein partner(s) by binding affinity thus forming protein complexes. Thus, an interacting protein partner prepared by purification from tissue samples or by recombinant expression or chemical synthesis may be bound covalently or non-covalently to a matrix such as Sepharose in, e.g., a chromatography column. The tissue sample or cell lysate from the recombinant cells can then be contacted with the bound protein on the matrix. A low-salt solution is used to wash off the unbound components, and a high-salt solution is then employed to elute the bound protein complexes in the column. In affinity blotting, crude protein samples from a tissue sample or recombinant host cell lysate can be fractionated on a polyacrylamide gel electrophoresis (PAGE) and then transferred to, e.g., a nitrocellulose membrane. The purified interacting protein member is then bound to its interacting protein partner(s) on the membrane forming protein complexes, which are then isolated from the membrane.

It will be apparent to skilled artisans that any recombinant expression methods may be used in the present invention for purposes of recombinantly expressing the protein complexes or individual interacting proteins. Generally, a nucleic acid encoding an interacting protein member can be introduced into a suitable host cell. For purposes of recombinantly forming a protein complex within a host cell, nucleic acids encoding two or more interacting protein members should be introduced into the host cell.

Typically, the nucleic acids, preferably in the form of DNA, are incorporated into a vector to form expression vectors capable of expressing the interacting protein member(s) once introduced into a host cell. Many types of vectors can be used for the present invention. Methods for the construction of an expression vector for purposes of this invention should be apparent to skilled artisans apprised of the present disclosure. See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516-544 (1987); *The Molecular Biology of the Yeast Saccharomyces*, Eds. Strathern et al., Cold Spring Harbor Press, Vols. I and II, 1982; and Sambrook et al., *Molecular Cloning: A Laboratory Manual*, Cold Spring Harbor Press, 1989.

Generally, the expression vectors include an expression cassette having a promoter operably linked to a DNA encoding an interacting protein member. The promoter can be a native promoter, i.e., the promoter found in naturally occurring cells to be responsible for the expression of the interacting protein member in the cells. Alternatively, the expression cassette can be a chimeric one, i.e., having a heterologous promoter that is not the native promoter responsible for the expression of the interacting protein member in naturally occurring cells. The expression vector may further include an origin of DNA replication for the replication of the vectors in host cells. Preferably, the expression vectors also include a replication origin for the amplification of the vectors in, e.g., *E. coli*, and selection marker(s) for selecting and maintaining only those host cells harboring the expression vectors. Additionally, the expression cassettes preferably also contain inducible elements, which function to control the transcription from the DNA encoding an interacting protein member. Other regulatory sequences such as transcriptional enhancer sequences and translation regulation sequences (e.g., Shine-Dalgarno sequence) can also be operably included in the expression cassettes. Termination sequences such as the polyadenylation signals from bovine growth hormone, SV40, lacZ and AcMNPV polyhedral protein genes may also be operably linked to the DNA encoding an interacting protein member in the expression cassettes. An epitope tag coding sequence for detection and/or purification of the expressed protein can also be operably linked to the DNA encoding an interacting protein member such that a fusion protein is expressed. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies immunoreactive with many epitope tags are generally commercially available. The expression vectors may also contain components that direct the expressed protein extracellularly or to a particular intracellular compartment. Signal peptides, nuclear localization sequences, endoplasmic reticulum retention signals, mitochondrial localization sequences, myristoylation signals, palmitoylation signals, and transmembrane sequences are example of optional vector components that can determine the destination of expressed proteins. When it is desirable to express two or more interacting protein members in a single host cell, the DNA fragments encoding the interacting protein members may be incorporated into a single vector or different vectors.

The thus constructed expression vectors can be introduced into the host cells by any techniques known in the art, e.g., by direct DNA transformation, microinjection, electroporation, viral infection, lipofection, gene gun, and the like. The expression of the interacting protein members may be transient or stable. The expression vectors can be maintained in host cells in an extrachromosomal state, i.e., as self-replicating plasmids or viruses. Alternatively, the expression vectors can be integrated into chromosomes of the host cells by conventional techniques such as selection of stable cell lines or site-specific recombination. In stable cell lines, at least the expression cassette portion of the expression vector is integrated into a chromosome of the host cells.

The vector construct can be designed to be suitable for expression in various host cells, including but not limited to bacteria, yeast cells, plant cells, insect cells, and mammalian and human cells. Methods for preparing expression vectors for expression in different host cells should be apparent to a skilled artisan.

Homologues and fragments of the native interacting protein members can also be easily expressed using the recombinant methods described above. For example, to express a protein fragment, the DNA fragment incorporated into the expression vector can be selected such that it only encodes the protein fragment. Likewise, a specific hybrid protein can be expressed using a recombinant DNA encoding the hybrid protein. Similarly, a homologue protein may be expressed from a DNA sequence encoding the homologue protein or protein fragment. A homologue-encoding DNA sequence may be obtained by manipulating the native protein-encoding sequence using recombinant DNA techniques. For this purpose, random or site-directed mutagenesis can be conducted using techniques generally known in the art. To make protein derivatives, for example, the amino acid sequence of a native interacting protein member may be changed in predetermined manners by site-directed DNA mutagenesis to create or remove consensus sequences for, e.g., phosphorylation by protein kinases, glycosylation, ribosylation, myristolation, palmytoylation, and the like. Alternatively, non-natural amino acids can be incorporated into an interacting protein member during the synthesis of the protein in recombinant host cells. For example, photoreactive lysine derivatives can be incorporated into an interacting protein member during translation by using a modified lysyl-tRNA. See, e.g., Wiedmann et al., *Nature*, 328:830-833 (1989); Musch et al., *Cell*, 69:343-352 (1992). Other photoreactive amino acid derivatives can also be incorporated in a similar manner. See, e.g., High et al., *J. Biol. Chem.*, 368:28745-28751 (1993). Indeed, the photoreactive amino acid derivatives thus incorporated into an interacting protein member can function to cross-link the protein to its interacting protein partner in a protein complex under predetermined conditions.

In addition, derivatives of the native interacting protein members of the present invention can also be prepared by chemically linking certain moieties to amino acid side chains of the native proteins.

If desired, the homologues and derivatives thus generated can be tested to determine whether they are capable of interacting with their intended interacting partners to form protein complexes. Testing can be conducted by e.g., the yeast two-hybrid system or other methods known in the art for detecting protein-protein interaction.

A hybrid protein as described above having Tsg101 or a homologue, derivative, or fragment thereof covalently linked by a peptide bond or a peptide linker to HIV GAG or HIV GAGp6, or a homologue, derivative, or fragment thereof, can be expressed recombinantly from a chimeric nucleic acid, e.g., a DNA or mRNA fragment encoding the fusion protein. Accordingly, the present invention also provides a nucleic acid encoding the hybrid protein of the present invention. In addition, an expression vector having incorporated therein a nucleic acid encoding the hybrid protein of the present invention is also provided. The methods for making such chimeric nucleic acids and expression vectors containing them should be apparent to skilled artisans apprised of the present disclosure.

2.4. Protein Microchip

In accordance with another embodiment of the present invention, a protein microchip or microarray is provided having one or more of the protein complexes and/or antibodies selectively immunoreactive with the protein complexes of the present invention. Protein microarrays are becoming increasingly important in both proteomics research and protein-based detection and diagnosis of diseases. The protein microarrays in accordance with this embodiment of the present invention will be useful in a variety of applications including, e.g., large-scale or high-throughput screening for compounds capable of binding to the protein complexes or modulating the interactions between the interacting protein members in the protein complexes.

The protein microarray of the present invention can be prepared in a number of methods known in the art. An example of a suitable method is that disclosed in MacBeath and Schreiber, *Science*, 289:1760-1763 (2000). Essentially, glass microscope slides are treated with an aldehyde-containing silane reagent (SuperAldehyde Substrates purchased from TeleChem International, Cupertino, Calif.). Nanoliter volumes of protein samples in a phophate-buffered saline with 40% glycerol are then spotted onto the treated slides using a high-precision contact-printing robot. After incubation, the slides are immersed in a bovine serum albumin (BSA)-containing buffer to quench the unreacted aldehydes and to form a BSA layer which functions to prevent non-specific protein binding in subsequent applications of the microchip. Alternatively, as disclosed in MacBeath and Schreiber, proteins or protein complexes of the present invention can be attached to a BSA-NHS slide by covalent linkages. BSA-NHS slides are fabricated by first attaching a molecular layer of BSA to the surface of glass slides and then activating the BSA with N,N'-disuccinimidyl carbonate. As a result, the amino groups of the lysine, aspartate, and glutamate residues on the BSA are activated and can form covalent urea or amide linkages with protein samples spotted on the slides. See MacBeath and Schreiber, *Science*, 289:1760-1763 (2000).

Another example of useful method for preparing the protein microchip of the present invention is that disclosed in PCT Publication Nos. WO 00/4389A2 and WO 00/04382, both of which are assigned to Zyomyx and are incorporated herein by reference. First, a substrate or chip base is covered with one or more layers of thin organic film to eliminate any surface defects, insulate proteins from the base materials, and to ensure uniform protein array. Next, a plurality of protein-capturing agents (e.g., antibodies, peptides, etc.) are arrayed and attached to the base that is covered with the thin film. Proteins or protein complexes can then be bound to the capturing agents forming a protein microarray. The protein microchips are kept in flow chambers with an aqueous solution.

The protein microarray of the present invention can also be made by the method disclosed in PCT Publication No. WO 99/36576 assigned to Packard Bioscience Company, which is incorporated herein by reference. For example, a three-dimensional hydrophilic polymer matrix, i.e., a gel, is first disposed on a solid substrate such as a glass slide. The polymer matrix gel is capable of expanding or contracting and contains a coupling reagent that reacts with amine groups. Thus, proteins and protein complexes can be contacted with the matrix gel in an expanded aqueous and porous state to allow reactions between the amine groups on the protein or protein complexes with the coupling reagents thus immobilizing the proteins and protein complexes on the substrate. Thereafter, the gel is contracted to embed the attached proteins and protein complexes in the matrix gel.

Alternatively, the proteins and protein complexes of the present invention can be incorporated into a commercially available protein microchip, e.g., the ProteinChip System from Ciphergen Biosystems Inc., Palo Alto, Calif. The ProteinChip System comprises metal chips having a treated surface, which interact with proteins. Basically, a metal chip surface is coated with a silicon dioxide film. The molecules of interest such as proteins and protein complexes can then be attached covalently to the chip surface via a silane coupling agent.

The protein microchips of the present invention can also be prepared with other methods known in the art, e.g., those disclosed in U.S. Pat. Nos. 6,087,102, 6,139,831, 6,087,103; PCT Publication Nos. WO 99/60156, WO 99/39210, WO 00/54046, WO 00/53625, WO 99/51773, WO 99/35289, WO 97/42507, WO 01/01142, WO 00/63694, WO 00/61806, WO 99/61148, WO 99/40434, all of which are incorporated herein by reference.

3. Antibodies

In accordance with another aspect of the present invention, an antibody immunoreactive against a protein complex of the present invention is provided. In one embodiment, the antibody is selectively immunoreactive with a protein complex of the present invention. Specifically, the phrase "selectively immunoreactive with a protein complex" as used herein means that the immunoreactivity of the antibody of the present invention with the protein complex is substantially higher than that with the individual interacting members of the protein complex so that the binding of the antibody to the protein complex is readily distinguishable from the binding of the antibody to the individual interacting member proteins based on the strength of the binding affinities. Preferably, the binding constant differs by a magnitude of at least 2 fold, more preferably at least 5 fold, even more preferably at least 10 fold, and most preferably at least 100 fold. In a specific embodiment, the antibody is not substantially immunoreactive with the interacting protein members of the protein complex.

The antibody of the present invention can be readily prepared using procedures generally known in the art. See, e.g., Harlow and Lane, *Antibodies: A Laboratory Manual*, Cold Spring Harbor Press, 1988. Typically, the protein complex against which the antibody to be generated will be immunoreactive is used as the antigen for the purpose of producing immune response in a host animal. In one embodiment, the protein complex used consists the native proteins. Preferably, the protein complex includes only the binding domains of Tsg101 and HIV GAGp6, respectively. As a result, a greater portion of the total antibodies may be selectively immunoreactive with the protein complexes. The binding domains can be selected from, e.g., those summarized in Table 1. In addition, various techniques known in the art for predicting epitopes may also be employed to design antigenic peptides based on the interacting protein members in a protein complex of the present invention to increase the possibility of producing an antibody selectively immunoreactive with the protein complex. Suitable epitope-prediction computer programs include, e.g., MacVector from International Biotechnologies, Inc. and Protean from DNAStar.

In a specific embodiment, a hybrid protein as described above in Section 2 is used as an antigen which has Tsg101 or a homologues, derivative, or fragment thereof covalently linked by a peptide bond or a peptide linker to HIV GAG or HIV GAGp6 or a homologue, derivative, or fragment thereof. In a preferred embodiment, the hybrid protein consists of two interacting binding domains selected from Table 1, or homologues or derivatives thereof, covalently linked together by a peptide bond or a linker molecule.

The antibody of the present invention can be a polyclonal antibody to a protein complex of the present invention. To produce the polyclonal antibody, various animal hosts can be employed, including, e.g., mice, rats, rabbits, goats, guinea pigs, hamsters, etc. A suitable antigen which is a protein complex of the present invention or a derivative thereof as described above can be administered directly to a host animal to illicit immune reactions. Alternatively, it can be administered together with a carrier such as keyhole limpet hemocyanin (KLH), bovine serum albumin (BSA), ovalbumin, and Tetanus toxoid. Optionally, the antigen is conjugated to a carrier by a coupling agent such as carbodiimide, glutaraldehyde, and MBS. Any conventional adjuvants may be used to boost the immune response of the host animal to the protein complex antigen. Suitable adjuvants known in the art include but are not limited to Complete Freund's Adjuvant (which contains killed mycobacterial cells and mineral oil), incomplete Freund's Adjuvant (which lacks the cellular components), aluminum salts, MF59 from Biocine, monophospholipid, synthetic trehalose dicorynomycolate (TDM) and cell wall skeleton (CWS) both from RIBI ImmunoChem Research Inc., Hamilton, Mont., non-ionic surfactant vesicles (NISV) from Proteus International PLC, Cheshire, U.K., and saponins. The antigen preparation can be administered to a host animal by subcutaneous, intramuscular, intravenous, intradermal, or intraperitoneal injection, or by injection into a lymphoid organ.

The antibodies of the present invention may also be monoclonal. Such monoclonal antibodies may be developed using any conventional techniques known in the art. For example, the popular hybridoma method disclosed in Kohler and Milstein, *Nature*, 256:495-497 (1975) is now a well-developed technique that can be used in the present invention. See U.S. Pat. No. 4,376,110, which is incorporated herein by reference. Essentially, B-lymphocytes producing a polyclonal antibody against a protein complex of the present invention can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See generally, Harlow and Lane, *Antibodies: A Laboratory Manual*, Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In addition, antibodies selectively immunoreactive with a protein complex of the present invention may also be recombinantly produced. For example, cDNAs prepared by PCR amplification from activated B-lymphocytes or hybridomas may be cloned into an expression vector to form a cDNA library, which is then introduced into a host cell for recombinant expression. The cDNA encoding a specific desired protein may then be isolated from the library. The isolated cDNA can be introduced into a suitable host cell for the expression of the protein. Thus, recombinant techniques can be used to recombinantly produce specific native antibodies, hybrid antibodies capable of simultaneous reaction with more than one antigen, chimeric antibodies (e.g., the constant and variable regions are derived from different sources), univalent antibodies which comprise one heavy and light chain pair coupled with the Fc region of a third (heavy) chain, Fab proteins, and the like. See U.S. Pat. No. 4,816,567; European Patent Publication No. 0088994; Munro, *Nature*, 312:597 (1984); Morrison, *Science*, 229: 1202 (1985); Oi et al., *BioTechniques*, 4:214 (1986); and Wood et al., *Nature*, 314:446-449 (1985), all of which are incorporated herein by reference. Antibody fragments such as Fv fragments, single-chain Fv fragments (scFv), Fab' fragments, and F(ab')$_2$ fragments can also be recombinantly produced by methods disclosed in, e.g., U.S. Pat. No. 4,946,778; Skerra & Plückthun, *Science*, 240:1038-1041 (1988); Better et al., *Science*, 240:1041-1043 (1988); and Bird, et al., *Science*, 242:423-426 (1988), all of which are incorporated herein by reference.

In a preferred embodiment, the antibodies provided in accordance with the present invention are partially or fully humanized antibodies. For this purpose, any methods known in the art may be used. For example, partially humanized chimeric antibodies having V regions derived from the tumor-specific mouse monoclonal antibody, but human C regions are disclosed in Morrison and Oi, *Adv. Immunol.*, 44:65-92 (1989). In addition, fully humanized antibodies can be made using transgenic non-human animals. For example, transgenic non-human animals such as transgenic mice can be produced in which endogenous immunoglobulin genes are suppressed or deleted, while heterologous antibodies are encoded entirely by exogenous immunoglobulin genes, preferably human immunoglobulin genes, recombinantly introduced into the genome. See e.g., U.S. Pat. Nos. 5,530,101; 5,545,806; 6,075,181; PCT Publication No. WO 94/02602; Green et. al., *Nat. Genetics*, 7: 13-21 (1994); and Lonberg et al., *Nature* 368: 856-859 (1994), all of which are incorporated herein by reference. The transgenic non-human host animal may be immunized with suitable antigens such as a protein complex of the present invention or one or more of the interacting protein members thereof to illicit specific immune response thus producing humanized antibodies. In addition, cell lines producing specific humanized antibodies can also be derived from the immunized transgenic non-human animals. For example, mature B-lymphocytes obtained from a transgenic animal producing humanized antibodies can be fused to myeloma cells and the resulting hybridoma clones may be selected for specific humanized antibodies with desired binding specificities. Alternatively, cDNAs may be extracted from mature B-lymphocytes and used in establishing a library that is subsequently screened for clones encoding humanized antibodies with desired binding specificities.

In yet another embodiment, a bifunctional antibody is provided which has two different antigen binding sites, each being specific to a different interacting protein member in a protein complex of the present invention. The bifunctional antibody may be produced using a variety of methods known in the art. For example, two different monoclonal antibody-producing hybridomas can be fused together. One of the two hybridomas may produce a monoclonal antibody specific against an interacting protein member of a protein complex of the present invention, while the other hybridoma generates a monoclonal antibody immunoreactive with another interacting protein member of the protein complex. The thus formed new hybridoma produces different antibodies including a desired bifunctional antibody, i.e., an antibody immunoreactive with both of the interacting protein members. The bifunctional antibody can be readily purified. See Milstein and Cuello, *Nature,* 305:537-540 (1983).

Alternatively, a bifunctional antibody may also be produced using heterobifunctional crosslinkers to chemically link two different monoclonal antibodies, each being immunoreactive with a different interacting protein member of a protein complex. Therefore, the aggregate will bind to two interacting protein members of the protein complex. See Staerz et al, *Nature,* 314:628-631 (1985); Perez et al, *Nature,* 316:354-356 (1985).

In addition, bifunctional antibodies can also be produced by recombinantly expressing light and heavy chain genes in a hybridoma that itself produces a monoclonal antibody. As a result, a mixture of antibodies including a bifunctional antibody is produced. See DeMonte et al, *Proc. Natl. Acad. Sci., USA,* 87:2941-2945 (1990); Lenz and Weidle, *Gene,* 87:213-218 (1990).

Preferably, a bifunctional antibody in accordance with the present invention is produced by the method disclosed in U.S. Pat. No. 5,582,996, which is incorporated herein by reference. For example, two different Fabs can be provided and mixed together. The first Fab can bind to an interacting protein member of a protein complex, and has a heavy chain constant region having a first complementary domain not naturally present in the Fab but capable of binding a second complementary domain. The second Fab is capable of binding another interacting protein member of the protein complex, and has a heavy chain constant region comprising a second complementary domain not naturally present in the Fab but capable of binding to the first complementary domain. Each of the two complementary domains is capable of stably binding to the other but not to itself. For example, the leucine zipper regions of c-fos and c-jun oncogenes may be used as the first and second complementary domains. As a result, the first and second complementary domains interact with each other to form a leucine zipper thus associating the two different Fabs into a single antibody construct capable of binding to two antigenic sites.

Other suitable methods known in the art for producing bifunctional antibodies may also be used, which include those disclosed in Holliger et al., *Proc. Nat'l Acad. Sci. USA,* 90:6444-6448 (1993); de Kruif et al., *J. Biol. Chem.,* 271: 7630-7634 (1996); Coloma and Morrison, *Nat. Biotechnol.,* 15:159-163 (1997); Muller et al., *FEBS Lett.,* 422:259-264 (1998); and Muller et al., *FEBS Lett.,* 432:45-49 (1998), all of which are incorporated herein by reference.

4. Screening Assays

The protein complexes of the present invention, Tsg101 and HIV GAG or HIV GAGp6 can be used in screening assays to select modulators of Tsg101, HIV GAGp6, and protein complexes of the present invention. In addition, homologues, derivatives and fragments of Tsg101, HIV GAG, HIV GAGp6, and protein complexes containing such homologues, derivatives and fragments may also be used in the screening assays. As used herein, the term "modulator" encompasses any compounds that can cause any forms of alteration of the properties, biological activities or functions of the proteins or protein complexes, including, e.g., enhancing or reducing their biological activities, increasing or decreasing their stability, altering their affinity or specificity to certain other biological molecules, etc. In addition, the term "modulator" as used herein also includes any compounds that simply bind Tsg101, HIV GAGp6, and/or the proteins complexes of the present invention. For example, a modulator can be an interaction antagonist capable of interfering with, or disrupting or dissociating protein-protein interaction between Tsg101 or a homologue or derivative thereof and HIV GAGp6 or a homologue or derivative thereof.

Likewise, other retroviral GAG polypeptides containing the P(T/S)AP (SEQ ID NO:1 or SEQ ID NO:3) late domain motif, or homologues, derivatives or fragments thereof may also be used in the screening assays in lieu of HIV GAG or HIV GAGp6. In other words, any interacting members of the protein complexes provided according to the present invention (e.g., as described in Section 2) can be used in the screening assays.

The term "interaction antagonist" as used herein means a compound that interferes with, blocks, disrupts or destabilizes a protein-protein interaction; blocks or interferes with the formation of a protein complex; or destabilizes, disrupts or dissociates an existing protein complex.

The term "interaction agonist" as used herein means a compound that triggers, initiates, propagates, nucleates, or otherwise enhances the formation of a protein-protein interaction; triggers, initiates, propagates, nucleates, or otherwise enhances the formation of a protein complex; or stabilizes an existing protein complex.

Accordingly, the present invention provides screening methods for selecting modulators of Tsg101 or HIV GAGp6 or a mutant form thereof, or a protein complex formed between Tsg101 or a Tsg101 fragment, or a homologue or derivative thereof and HIV GAG or HIV GAGp6 or fragment, or a homologue or derivative thereof. The targets suitable in the screening methods of the present invention may include any embodiments of the protein complexes of the present invention as described in Section 2. Preferably, protein fragments are used in forming the protein complexes. For example, a preferred target protein complex can include a Tsg101 protein fragment encompassing the UEV domain. Also for example, the HIV GAGp6 or a fragment thereof may be used in forming a target protein complex. In a specific embodiment, a polypeptide including the first 14 amino acids of the HIV GAGp6 is used in forming a target protein complex. In another embodiment, fusion proteins are used in which a detectable epitope tag is fused to a Tsg101 protein or a homologue or derivative or fragment thereof and/or to a HIV GAGp6 polypeptide or a homologue or derivative or fragment thereof. Suitable examples of such epitope tags include sequences derived from, e.g., influenza virus hemagglutinin (HA), Simian Virus 5 (V5), polyhistidine (6×His), c-myc, lacZ, GST, and the like.

When Tsg101 protein or a homologue or derivative or fragment thereof is used as a target protein in the screening methods of the present invention, preferably the Tsg101 UEV domain is included in the Tsg101 protein or a homologue or derivative or fragment thereof. And preferably the Tsg101 protein or a homologue or derivative or fragment thereof is fused to a detectable tag such as sequences derived from, e.g., influenza virus hemagglutinin (HA), Simian Virus 5 (V5), polyhistidine (6×His), c-myc, lacZ, GST, and the like. In this respect, compounds selected by the methods capable of binding to Tsg101 protein, preferably the UEV domain of Tsg101 protein can be tested for their ability to inhibit or interfere with the interactions between Tsg101 and HIV GAGp6. They can also be tested for their ability to inhibit HIV viral budding or HIV propagation. Suitable methods for such testing should be apparent to skilled artisan apprised of the present disclosure.

The modulators selected in accordance with the screening methods of the present invention can be effective in modulating the functions or activities of Tsg101, HIV GAG, HIV GAGp6, other retroviral GAG polypeptides containing the P(T/S)AP (SEQ ID NO:1 or SEQ ID NO:3) motif, or the protein complexes of the present invention. For example, compounds capable of binding the protein complexes may be capable of modulating the functions of the protein complexes. Additionally, compounds that interfere with, weaken, dissociate or disrupt, or alternatively, initiate, facilitate or stabilize the protein-protein interaction between the interacting protein members of the protein complexes can also be effective in modulating the functions or activities of the protein complexes. Thus, the compounds identified in the screening methods of the present invention can be made into therapeutically or prophylactically effective drugs for preventing or ameliorating diseases, disorders or symptoms caused by or associated with the protein complexes or Tsg101 or HIV GAG or HIV GAGp6 or other retroviral GAG polypeptides. Alternatively, they may be used as leads to aid the design and identification of therapeutically or prophylactically effective compounds for diseases, disorders or symptoms caused by or associated with the protein complexes of the present invention or interacting members thereof. The protein complexes and/or interacting protein members thereof in accordance with the present invention can be used in any of a variety of drug screening techniques. Drug screening can be performed as described herein or using well-known techniques, such as those described in U.S. Pat. Nos. 5,800,998 and 5,891,628, both of which are incorporated herein by reference.

4.1. Test Compounds

Any test compounds may be screened in the screening assays of the present invention to select modulators of a Tsg101-containing protein complex of the present invention or interacting members thereof. By the term "selecting" or "select" modulators it is intended to encompass both (a) choosing compounds from a group previously unknown to be modulators of a Tsg101-containing protein complex of the present invention and/or an interacting member thereof, and (b) testing compounds that are known to be capable of binding, or modulating the functions and activities of, a Tsg101-containing protein complex of the present invention and/or an interacting member thereof. Both types of compounds are generally referred to herein as "test compounds." The test compounds may include, by way of example, proteins (e.g., antibodies, small peptides, artificial or natural proteins), nucleic acids, and derivatives, mimetics and analogs thereof, and small organic molecules having a molecular weight of no greater than 10,000 daltons, more preferably less than 5,000 daltons. Preferably, the test compounds are provided in library formats known in the art, e.g., in chemically synthesized libraries, recombinant expression libraries (e.g., phage display libraries), and in vitro translation-based libraries (e.g., ribosome display libraries).

For example, the screening assays of the present invention can be used in the antibody production processes described in Section 3 to select antibodies with desirable specificities. Various forms antibodies or derivatives thereof may be screened, including but not limited to, polyclonal antibodies, monoclonal antibodies, bifunctional antibodies, chimeric antibodies, single chain antibodies, antibody fragments such as Fv fragments, single-chain Fv fragments (scFv), Fab' fragments, and F(ab')$_2$ fragments, and various modified forms of antibodies such as catalytic antibodies, and antibodies conjugated to toxins or drugs, and the like. The antibodies can be of any types such as IgG, IgE, IgA, or IgM. Humanized antibodies are particularly preferred. Preferably, the various antibodies and antibody fragments may be provided in libraries to allow large-scale high throughput screening. For example, expression libraries expressing antibodies or antibody fragments may be constructed by a method disclosed, e.g., in Huse et al., *Science*, 246:1275-1281 (1989), which is incorporated herein by reference. Single-chain Fv (scFv) antibodies are of particular interest in diagnostic and therapeutic applications. Methods for providing antibody libraries are also provided in U.S. Pat. Nos. 6,096,551; 5,844,093; 5,837,460; 5,789,208; and 5,667,988, all of which are incorporated herein by reference.

Peptidic test compounds may be peptides having L-amino acids and/or D-amino acids, phosphopeptides, and other types of peptides. The screened peptides can be of any size, but preferably have less than about 50 amino acids. Smaller peptides are easier to deliver into a patient's body. Various forms of modified peptides may also be screened. Like antibodies, peptides can also be provided in, e.g., combinatorial libraries. See generally, Gallop et al., *J. Med. Chem.*, 37:1233-1251 (1994). Methods for making random peptide libraries are disclosed in, e.g., Devlin et al., *Science*, 249: 404-406 (1990). Other suitable methods for constructing peptide libraries and screening peptides therefrom are disclosed in, e.g., Scott and Smith, *Science*, 249:386-390 (1990); Moran et al., *J. Am. Chem. Soc.*, 117:10787-10788 (1995) (a library of electronically tagged synthetic peptides); Stachelhaus et al., *Science*, 269:69-72 (1995); U.S. Pat. Nos. 6,156,511; 6,107,059; 6,015,561; 5,750,344; 5,834,318; 5,750,344, all of which are incorporated herein by reference. For example, random-sequence peptide phage display libraries may be generated by cloning synthetic oligonucleotides into the gene III or gene VIII of an *E. coli.* filamentous phage. The thus generated phage can propagate in *E. coli.* and express peptides encoded by the oligonucleotides as fusion proteins on the surface of the phage. Scott and Smith, *Science*, 249:368-390 (1990). Alternatively, the "peptides on plasmids" method may also be used to form peptide libraries. In this method, random peptides may be fused to the C-terminus of the *E. coli.* Lac repressor by recombinant technologies and expressed from a plasmid that also contains Lac repressor-binding sites. As a result, the peptide fusions bind to the same plasmid that encodes them.

Small organic or inorganic non-peptide non-nucleotide compounds having a molecular weight of less than 5,000 daltons are preferred test compounds for the screening assays of the present invention. They too can be provided in a library format. See generally, Gordan et al. *J. Med. Chem.*, 37:1385-1401 (1994). For example, benzodiazepine libraries are provided in Bunin and Ellman, *J. Am. Chem. Soc.*, 114:10997-10998 (1992), which is incorporated herein by reference. A method for constructing and screening peptoid libraries are disclosed in Simon et al., *Proc. Natl. Acad. Sci. USA*, 89:9367-9371 (1992). Methods for the biosynthesis of novel polyketides in a library format are described in McDaniel et al, *Science*, 262:1546-1550 (1993) and Kao et al., *Science*, 265:509-512 (1994). Various libraries of small organic molecules and methods of construction thereof are disclosed in U.S. Pat. Nos. 6,162,926 (multiply-substituted fullerene derivatives); 6,093,798 (hydroxamic acid derivatives); 5,962,337 (combinatorial 1,4-benzodiazepin-2,5-dione library); 5,877,278 (Synthesis of N-substituted oligomers); 5,866,341 (compositions and methods for screening drug libraries); 5,792,821 (polymerizable cyclodextrin derivatives); 5,766,963 (hydroxypropylamine library); and 5,698,685 (morpholino-subunit combinatorial library), all of which are incorporated herein by reference.

Other compounds such as oligonucleotides and peptide nucleic acids (PNA), and analogs and derivatives thereof may also be screened to select clinically useful compounds. Combinatorial libraries of oligos are also known in the art. See Gold et al., *J. Biol. Chem.*, 270:13581-13584 (1995).

4.2. In Vitro Screening Assays

The test compounds may be screened in an in vitro assay to select compounds capable of binding the protein complexes or interacting protein members thereof in accordance with the present invention. For this purpose, a test compound is contacted with a protein complex or an interacting protein member thereof under conditions and for a time sufficient to allow specific interaction between the test compound and the target components to occur and thus binding of the compound to the target forming a complex. Subsequently, the binding event is detected.

Various screening techniques known in the art may be used in the present invention. The protein complexes and the interacting protein members thereof may be prepared by any suitable methods, e.g., by recombinant expression and purification. The protein complexes and/or interacting protein members thereof (both are referred to as "target" hereinafter in this section) may be free in solution or in cell extracts. A test compound may be mixed with a target forming a liquid mixture. The compound may be labeled with a detectable marker. Upon mixing under suitable conditions, the binding complex having the compound and the target may be co-immunoprecipitated and washed.

The compound in the precipitated complex may be detected based on the marker on the compound.

In a preferred embodiment, the target is immobilized on a solid support or on a cell surface. Preferably, the target can be arrayed into a protein microchip in a method described in Section 2. For example, a target may be immobilized directly onto a microchip substrate such as glass slides or onto a multi-well plates using non-neutralizing antibodies, i.e., antibodies capable of binding to the target but do not substantially affect its biological activities. To effect the screening, test compounds can be contacted with the immobilized target to allow binding to occur to form complexes under standard binding assay conditions. Either the targets or test compounds are labeled with a detectable marker using well-known labeling techniques. For example, U.S. Pat. No. 5,741,713 discloses combinatorial libraries of biochemical compounds labeled with NMR active isotopes. To select binding compounds, one may measure the formation of the target-test compound complexes or kinetics for the formation thereof. When combinatorial libraries of organic non-peptide non-nucleic acid compound are screened, it is preferred that labeled or encoded (or "tagged") combinatorial libraries are used to allow rapid decoding of lead structures. This is especially important because, unlike biological libraries, individual compounds found in chemical libraries cannot be amplified by self-amplification. Tagged combinatorial libraries are provided in, e.g., Borchardt and Still, *J. Am. Chem. Soc.*, 116:373-374 (1994) and Moran et al., *J. Am. Chem. Soc.*, 117:10787-10788 (1995), both of which are incorporated herein by reference.

Alternatively, the test compounds can be immobilized on a solid support, e.g., forming a microarray of test compounds. The target protein or protein complex is then contacted with the test compounds. The target may be labeled with any suitable detection marker. For example, the target may be labeled with radioactive isotopes or fluorescence marker before binding reaction occurs. Alternatively, after the binding reactions, antibodies that are immunoreactive with the target and are labeled with radioactive materials, fluorescence markers, enzymes, or labeled secondary anti-Ig antibodies may be used to detect any bound target thus selecting the binding compound. One example of this embodiment is the protein probing method. That is, the target provided in accordance with the present invention is used as a probe to screen expression libraries of proteins or random peptides. The expression libraries can be phage display libraries, in vitro translation-based libraries, or ordinary expression cDNA libraries. The libraries may be immobilized on a solid support such as nitrocellulose filters. See e.g., Sikela and Hahn, *Proc. Natl. Acad. Sci. USA*, 84:3038-3042 (1987). The probe may be labeled by a radioactive isotope or a fluorescence marker. Alternatively, the probe can be biotinylated and detected with a streptavidin-alkaline phosphatase conjugate. More conveniently, the bound probe may be detected with an antibody.

In yet another embodiment, a known ligand capable of binding to the target can be used in competitive binding assays. Complexes between the known ligand and the target can be formed in the presence of test compounds. The ability of a test compound to interfere with the interaction between the target and the known ligand is measured. The result can be compared with that in the absence of test compounds. Alternatively, the target-ligand complex can be formed and the complex is contacted with test compounds. One exemplary ligand is an antibody capable of specifically binding the target. Particularly, such an antibody is especially useful for identifying peptides that share one or more antigenic determinants of the target protein complex or interacting protein members thereof.

In specific embodiments, Tsg101 or a Tsg101 fragment (e.g., containing the UEV domain), or a homologue thereof is used as target, while HIV GAG or GAGp6, or a fragment thereof, or homologue thereof is used as ligand.

In a preferred embodiment, a protein complex used in the screening assay includes a hybrid protein as described in Section 2, which is formed by fusion of two interacting protein members or fragments or domains thereof. The hybrid protein may also be designed such that it contains a detectable epitope tag fused thereto. Suitable examples of such epitope tags include sequences derived from, e.g., influenza virus hemagglutinin (HA), Simian Virus 5 (V5), polyhistidine (6×His), c-myc, lacZ, GST, and the like.

Test compounds may also be screened in an in vitro assay to select interaction antagonists of the protein complexes identified in accordance with the present invention. Thus, for example, a Tsg101-HIV GAGp6 protein complex can be contacted with a test compound and disruption or destabilization of the protein complex can be detected.

The assay can be conducted in similar manners as the binding assays described above. For example, the presence or absence of a particular protein complex can be detected by an antibody selectively immunoreactive with the protein complex. Thus, after incubation of the protein complex with a test compound, immunoprecipitation assay can be conducted with the antibody. If the test compound disrupts the protein complex, then the amount of immunoprecipitated protein complex in this assay will be significantly less than that in a control assay in which the same protein complex is not contacted with the test compound. Various other detection methods may be suitable in the dissociation assay, as will be apparent to skilled artisan apprised of the present disclosure. In one embodiment, one of the interacting partner with a detectable marker fused thereto is fixed to a solid support. For example, a GST-GAGp6 fusion protein is attached to a solid support. Then the other interacting partner with a detectable marker fused thereto (e.g., a myc-tagged Tsg101 fragment containing the UEV domain) is contacted with the immobilized first interacting partner in the presence of one or more test compounds. If binding between the two interacting partners occurs, the myc-tagged Tsg101 fragment is also immobilized, which can be detected using an anti-myc antibody after the binding reaction mixture is washed to remove unbound myc-tagged Tsg101 fragment.

4.3. In Vivo Screening Assays

Test compounds can also be screened in any in vivo assays to select modulators of the protein complexes or interacting protein members thereof in accordance with the present invention. For example, any in vivo assays known in the art useful in selecting compounds capable of strengthening or interfering with the stability of the protein complexes of the present invention may be used.

4.3.1. Two-Hybrid Assays

In a preferred embodiment, one of the yeast two-hybrid systems or their analogous or derivative forms is used. Examples of suitable two-hybrid systems known in the art include, but are not limited to, those disclosed in U.S. Pat. Nos. 5,283,173; 5,525,490; 5,585,245; 5,637,463; 5,695,941; 5,733,726; 5,776,689; 5,885,779; 5,905,025; 6,037,136; 6,057,101; 6,114,111; and Bartel and Fields, eds., *The Yeast Two-Hybrid System*, Oxford University Press, New York, N.Y., 1997, all of which are incorporated herein by reference.

Typically, in a classic transcription-based two-hybrid assay, two chimeric genes are prepared encoding two fusion proteins: one contains a transcription activation domain fused to an interacting protein member of a protein complex of the present invention or an interacting domain of the interacting protein member, while the other fusion protein includes a DNA binding domain fused to another interacting protein member of the protein complex or an interacting domain thereof. For the purpose of convenience, the two interacting protein members or interacting domains thereof are referred to as "bait fusion protein" and "prey fusion protein," respectively. The chimeric genes encoding the fusion proteins are termed "bait chimeric gene" and "prey chimeric gene," respectively. Typically, a "bait vector" and a "prey vector" are provided for the expression of a bait chimeric gene and a prey chimeric gene, respectively.

4.3.1.1. Vectors

Many types of vectors can be used in a transcription-based two-hybrid assay. Methods for the construction of bait vectors and prey vectors should be apparent to skilled artisans in the art apprised of the present disclosure. See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516-544 (1987); *The Molecular Biology of the Yeast Saccharomyces*, Eds. Strathern et al., Cold Spring Harbor Press, Vols. I and II, 1982; and Rothstein in *DNA Cloning: A Practical Approach*, Vol. 11, Ed. DM Glover, IRL Press, Wash., D.C., 1986.

Generally, the bait and prey vectors include an expression cassette having a promoter operably linked to a chimeric gene for the transcription of the chimeric gene. The vectors may also include an origin of DNA replication for the replication of the vectors in host cells and a replication origin for the amplification of the vectors in, e.g., *E. coli*, and selection marker(s) for selecting and maintaining only those host cells harboring the vectors. Additionally, the expression cassette preferably also contains inducible elements, which function to control the expression of a chimeric gene. Making the expression of the chimeric genes inducible and controllable is especially important in the event that the fusion proteins or components thereof are toxic to the host cells. Other regulatory sequences such as transcriptional enhancer sequences and translation regulation sequences (e.g., Shine-Dalgarno sequence) can also be included in the expression cassette. Termination sequences such as the bovine growth hormone, SV40, lacZ and AcMNPV polyhedral polyadenylation signals may also be operably linked to a chimeric gene in the expression cassette. An epitope tag coding sequence for detection and/or purification of the fusion proteins can also be operably linked to the chimeric gene in the expression cassette. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vectors can be introduced into the host cells by any techniques known in the art, e.g., by direct DNA transformation, microinjection, electroporation, viral infection, lipofection, gene gun, and the like. The bait and prey vectors can be maintained in host cells in an extrachromosomal state, i.e., as self-replicating plasmids or viruses. Alternatively, one or both vectors can be integrated into chromosomes of the host cells by conventional techniques such as selection of stable cell lines or site-specific recombination.

The in vivo assays of the present invention can be conducted in many different host cells, including but not limited to bacteria, yeast cells, plant cells, insect cells, and mammalian cells. A skilled artisan will recognize that the designs of the vectors can vary with the host cells used. In one embodiment, the assay is conducted in prokaryotic cells such as *Escherichia coli, Salmonella, Klebsiella*, Pseudomonas, Caulobacter, and *Rhizobium*. Suitable origins of replication for the expression vectors useful in this embodiment of the present invention include, e.g., the ColE1, pSC101, and M13 origins of replication. Examples of suitable promoters include, for example, the T7 promoter, the lacZ promoter, and the like. In addition, inducible promoters are also useful in modulating the expression of the chimeric genes. For example, the lac operon from bacteriophage lambda plac5 is well known in the art and is inducible by the addition of IPTG to the growth medium. Other known inducible promoters useful in a bacteria expression system include pL of bacteriophage λ, the trp promoter, and hybrid promoters such as the tac promoter, and the like.

In addition, selection marker sequences for selecting and maintaining only those cells expressing the desirable fusion proteins should also be incorporated into the expression vectors. Numerous selection markers including auxotrophic markers and antibiotic resistance markers are known in the art and can all be useful for purposes of this invention. For example, the bla gene, which confers ampicillin resistance, is the most commonly used selection marker in prokaryotic expression vectors. Other suitable markers include genes that confer neomycin, kanamycin, or hygromycin resistance to the host cells. In fact, many vectors are commercially available from vendors such as Invitrogen Corp. of San Diego, Calif., Clontech Corp. of Palo Alto, Calif., BRL of Bethesda, Md., and Promega Corp. of Madison, Wis. These commercially available vectors, e.g., pBR322, pSPORT, pBluescriptIISK, pcDNAI, and pcDNAII all have a multiple cloning site into which the chimeric genes of the present invention can be conveniently inserted using conventional recombinant techniques. The constructed expression vectors can be introduced into host cells by various transformation or transfection techniques generally known in the art.

In another embodiment, mammalian cells are used as host cells for the expression of the fusion proteins and detection of protein-protein interactions. For this purpose, virtually any mammalian cells can be used including normal tissue cells, stable cell lines, and transformed tumor cells. Conveniently, mammalian cell lines such as CHO cells, Jurkat T cells, NIH 3T3 cells, HEK-293 cells, CV-1 cells, COS-1 cells, HeLa cells, VERO cells, MDCK cells, WI38 cells, and the like are used. Mammalian expression vectors are well known in the art and many are commercially available. Examples of suitable promoters for the transcription of the chimeric genes in mammalian cells include viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Inducible promoters can also be used. Suitable inducible promoters include, for example, the tetracycline responsive element (TRE) (See Gossen et al., *Proc. Natl. Acad. Sci. USA*, 89:5547-5551 (1992)), metallothionein IIA promoter, ecdysone-responsive promoter, and heat shock promoters. Suitable origins of replication for the replication and maintenance of the expression vectors in mammalian cells include, e.g., the Epstein Barr origin of replication in the presence of the Epstein Barr nuclear antigen (see Sugden et al., *Mole. Cell. Biol.*, 5:410-413 (1985)) and the SV40 origin of replication in the presence of the SV40 T antigen (which is present in COS-1 and COS-7 cells) (see Margolskee et al., *Mole. Cell. Biol.*, 8:2837 (1988)). Suitable selection markers include, but are not limited to, genes conferring resistance to neomycin, hygromycin, zeocin, and the like. Many commercially available mammalian expression vectors may be useful for the present invention, including, e.g., pCEP4, pcDNAI, pIND, pSecTag2, pVAX1, pcDNA3.1, and pBI-EGFP, and pDisplay. The vectors can be introduced into mammalian cells using any known techniques such as calcium phosphate precipitation, lipofection, electroporation, and the like. The bait vector and prey vector can be co-transformed into the same cell or, alternatively, introduced into two different cells which are subsequently fused together by cell fusion or other suitable techniques.

Viral expression vectors, which permit introduction of recombinant genes into cells by viral infection, can also be used for the expression of the fusion proteins. Viral expression vectors generally known in the art include viral vectors based on adenovirus, bovine papilloma virus, murine stem cell virus (MSCV), MFG virus, and retrovirus. See Sarver, et al., *Mol. Cell. Biol.*, 1: 486 (1981); Logan & Shenk, *Proc. Natl. Acad. Sci. USA*, 81:3655-3659 (1984); Mackett, et al., *Proc. Natl. Acad. Sci. USA*, 79:7415-7419 (1982); Mackett, et al., *J. Virol.*, 49:857-864 (1984); Panicali, et al., *Proc. Natl. Acad. Sci. USA*, 79:4927-4931 (1982); Cone & Mulligan, *Proc. Natl. Acad. Sci. USA*, 81:6349-6353 (1984); Mann et al., *Cell*, 33:153-159 (1993); Pear et al., *Proc. Natl. Acad. Sci. USA*, 90:8392-8396 (1993); Kitamura et al., *Proc. Natl. Acad. Sci. USA*, 92:9146-9150 (1995); Kinsella et al., *Human Gene Therapy*, 7:1405-1413 (1996); Hofmann et al., *Proc. Natl. Acad. Sci. USA*, 93:5185-5190 (1996); Choate et al., *Human Gene Therapy*, 7:2247 (1996); WO 94/19478; Hawley et al., *Gene Therapy*, 1:136 (1994) and Rivere et al., *Genetics*, 92:6733 (1995), all of which are incorporated by reference.

Generally, to construct a viral vector, a chimeric gene according to the present invention can be operably linked to a suitable promoter. The promoter-chimeric gene construct is then inserted into a non-essential region of the viral vector, typically a modified viral genome. This results in a viable recombinant virus capable of expressing the fusion protein encoded by the chimeric gene in infected host cells. Once in the host cell, the recombinant virus typically is integrated into the genome of the host cell. However, recombinant bovine papilloma viruses typically replicate and remain as extrachromosomal elements.

In another embodiment, the detection assays of the present invention are conducted in plant cell systems. Methods for expressing exogenous proteins in plant cells are well known in the art. See generally, Weissbach & Weissbach, *Methods for Plant Molecular Biology*, Academic Press, NY, 1988; Grierson & Corey, *Plant Molecular Biology*, 2d Ed., Blackie, London, 1988. Recombinant virus expression vectors based on, e.g., cauliflower mosaic virus (CaMV) or tobacco mosaic virus (TMV) can all be used. Alternatively, recombinant plasmid expression vectors such as Ti plasmid vectors and Ri plasmid vectors are also useful. The chimeric genes encoding the fusion proteins of the present invention can be conveniently cloned into the expression vectors and placed under control of a viral promoter such as the 35S RNA and 19S RNA promoters of CaMV or the coat protein promoter of TMV, or of a plant promoter, e.g., the promoter of the small subunit of RUBISCO and heat shock promoters (e.g., soybean hsp17.5-E or hsp17.3-B promoters).

In addition, the in vivo assay of the present invention can also be conducted in insect cells, e.g., *Spodoptera frugiperda* cells, using a baculovirus expression system. Expression vectors and host cells useful in this system are well known in the art and are generally available from various commercial vendors. For example, the chimeric genes of the present invention can be conveniently cloned into a non-essential region (e.g., the polyhedrin gene) of an *Autographa californica* nuclear polyhedrosis virus (AcNPV) vector and placed under control of an AcNPV promoter (e.g., the polyhedrin promoter). The non-occluded recombinant viruses thus generated can be used to infect host cells such as *Spodoptera frugiperda* cells in which the chimeric genes are expressed. See U.S. Pat. No. 4,215,051.

In a preferred embodiment of the present invention, the fusion proteins are expressed in a yeast expression system using yeasts such as *Saccharomyces cerevisiae, Hansenula polymorpha, Pichia pastoris*, and *Schizosaccharomyces pombe* as host cells. The expression of recombinant proteins in yeasts is a well-developed field, and the techniques useful in this respect are disclosed in detail in *The Molecular Biology of the Yeast Saccharomyces*, Eds. Strathern et al., Vols. I and II, Cold Spring Harbor Press, 1982; Ausubel et al., *Current Protocols in Molecular Biology*, New York, Wiley, 1994; and Guthrie and Fink, *Guide to Yeast Genetics and Molecular Biology*, in *Methods in Enzymology*, Vol. 194, 1991, all of which are incorporated herein by reference. Sudbery, *Curr. Opin. Biotech.*, 7:517-524 (1996) reviews the success in the art in expressing recombinant proteins in various yeast species; the entire content and references cited therein are incorporated herein by reference. In addition, Bartel and Fields, eds., *The Yeast Two-Hybrid System*, Oxford University Press, New York, N.Y., 1997 contains extensive discussions of recombinant expression of fusion proteins in yeasts in the context of various yeast two-hybrid systems, and cites numerous relevant references. These and other methods known in the art can all be used for purposes of the present invention. The application of such methods to the present invention should be apparent to a skilled artisan apprised of the present disclosure.

Generally, each of the two chimeric genes is included in a separate expression vector (bait vector and prey vector). Both vectors can be co-transformed into a single yeast host cell. As will be apparent to a skilled artisan, it is also possible to express both chimeric genes from a single vector. In a preferred embodiment, the bait vector and prey vector are introduced into two haploid yeast cells of opposite mating types, e.g., a-type and α-type, respectively. The two haploid cells can be mated at a desired time to form a diploid cell expressing both chimeric genes.

Generally, the bait and prey vectors for recombinant expression in yeast include a yeast replication origin such as the 2μ origin or the ARSH4 sequence for the replication and maintenance of the vectors in yeast cells. Preferably, the vectors also have a bacteria origin of replication (e.g., ColE1) and a bacteria selection marker (e.g., amp$^R$ marker, i.e., bla gene). Optionally, the CEN6 centromeric sequence is included to control the replication of the vectors in yeast cells. Any constitutive or inducible promoters capable of driving gene transcription in yeast cells may be employed to control the expression of the chimeric genes. Such promoters are operably linked to the chimeric genes. Examples of suitable constitutive promoters include but are not limited to the yeast ADH1, PGK1, TEF2, GPD1, HIS3, and CYC1 promoters. Example of suitable inducible promoters include but are not limited to the yeast GAL1 (inducible by galactose), CUP1 (inducible by Cu$^{++}$), and FUS1 (inducible by pheromone) promoters; the AOX/MOX promoter from *H. polymorpha* and *P. Pastoris* (repressed by glucose or ethanol and induced by methanol); chimeric promoters such as those that contain LexA operators (inducible by LexA-containing transcription factors); and the like. Inducible promoters are preferred when the fusion proteins encoded by the chimeric genes are toxic to the host cells. If it is desirable, certain transcription repressing sequences such as the upstream repressing sequence (URS) from SPO13 promoter can be operably linked to the promoter sequence, e.g., to the 5' end of the promoter region. Such upstream repressing sequences function to fine-tune the expression level of the chimeric genes.

Preferably, a transcriptional termination signal is operably linked to the chimeric genes in the vectors. Generally, transcriptional termination signal sequences derived from, e.g., the CYC1 and ADH1 genes can be used.

Additionally, it is preferred that the bait vector and prey vector contain one or more selectable markers for the selection and maintenance of only those yeast cells that harbor a chimeric gene. Any selectable markers known in the art can be used for purposes of this invention so long as yeast cells expressing the chimeric gene(s) can be positively identified or negatively selected. Examples of markers that can be positively identified are those based on color assays, including the lacZ gene which encodes β-galactosidase, the firefly luciferase gene, secreted alkaline phosphatase, horseradish peroxidase, the blue fluorescent protein (BFP), and the green fluorescent protein (GFP) gene (see Cubitt et al., *Trends Biochem. Sci.*, 20:448-455 (1995)). Other markers emitting fluorescence, chemiluminescence, UV absorption, infrared radiation, and the like can also be used. Among the markers that can be selected are auxotrophic markers including, but not limited to, URA3, HIS3, TRP1, LEU2, LYS2, ADE2, and the like. Typically, for purposes of auxotrophic selection, the yeast host cells transformed with bait vector and/or prey vector are cultured in a medium lacking a particular nutrient. Other selectable markers are not based on auxotrophies, but rather on resistance or sensitivity to an antibiotic or other xenobiotic. Examples of such markers include but are not limited to chloramphenicol acetyl transferase (CAT) gene, which confers resistance to chloramphenicol; CAN1 gene, which encodes an arginine permease and thereby renders cells sensitive to canavanine (see Sikorski et al., *Meth. Enzymol.*, 194:302-318 (1991)); the bacterial kanamycin resistance gene (kan$^R$), which renders eucaryotic cells resistant to the aminoglycoside G418 (see Wach et al., *Yeast*, 10:1793-1808 (1994)); and CYH2 gene, which confers sensitivity to cycloheximide (see Sikorski et al., *Meth. Enzymol.*, 194:302-318 (1991)). In addition, the CUP1 gene, which encodes metallothionein and thereby confers resistance to copper, is also a suitable selection marker. Each of the above selection markers may be used alone or in combination. One or more selection markers can be included in a particular bait or prey vector. The bait vector and prey vector may have the same or different selection markers. In addition, the selection pressure can be placed on the transformed host cells either before or after mating the haploid yeast cells.

As will be apparent, the selection markers used should complement the host strains in which the bait and/or prey vectors are expressed. In other words, when a gene is used as a selection marker gene, a yeast strain lacking the selection marker gene (or having mutation in the corresponding gene) should be used as host cells. Numerous yeast strains or derivative strains corresponding to various selection markers are known in the art. Many of them have been developed specifically for certain yeast two-hybrid systems. The application and optional modification of such strains with respect to the present invention should be apparent to a skilled artisan apprised of the present disclosure. Methods for genetically manipulating yeast strains using genetic crossing or recombinant mutagenesis are well known in the art. See e.g., Rothstein, *Meth. Enzymol.*, 101:202-211

(1983). By way of example, the following yeast strains are well known in the art, and can be used in the present invention upon necessary modifications and adjustment:

L40 strain which has the genotype MATα his3Δ200 trp1-901 leu2-3,112 ade2 LYS2::(lexAop)4-HIS3 URA3:: (lexAop)8-lacZ;

EGY48 strain which has the genotype MATα trp1 his3 ura3 6ops-LEU2; and

MaV103 strain which has the genotype MATα ura3-52 leu2-3,112 trp1-901 his3Δ200 ade2-101 gal4Δ gal80Δ SPAL10::URA3 GAL1::HIS3::lys2 (see Kumar et al., *J. Biol. Chem.* 272:13548-13554 (1997); Vidal et al., *Proc. Natl. Acad. Sci. USA,* 93:10315-10320 (1996)). Such strains are generally available in the research community, and can also be obtained by simple yeast genetic manipulation. See, e.g., *The Yeast Two-Hybrid System*, Bartel and Fields, eds., pages 173-182, Oxford University Press, New York, N.Y., 1997.

In addition, the following yeast strains are commercially available:

Y190 strain which is available from Clontech, Palo Alto, Calif. and has the genotype MATa gal4 gal80 his3Δ200 trp1-901 ade2-101 ura3-52 leu2-3, 112 URA3::GAL1-lacZ LYS2::GAL1-HIS3 cyh$^r$; and YRG-2 Strain which is available from Stratagene, La Jolla, Calif. and has the genotype MATα ura3-52 his3-200 ade2-101 lys2-801 trp1-901 leu2-3, 112 gal4-542 gal80-538 L YS2::GAL1-HIS3 URA3:: GAL1/CYC1-lacZ.

In fact, different versions of vectors and host strains specially designed for yeast two-hybrid system analysis are available in kits from commercial vendors such as Clontech, Palo Alto, Calif. and Stratagene, La Jolla, Calif., all of which can be modified for use in the present invention.

4.3.1.2. Reporters

Generally, in a transcription-based two-hybrid assay, the interaction between a bait fusion protein and a prey fusion protein brings the DNA-binding domain and the transcription-activation domain into proximity forming a functional transcriptional factor, which acts on a specific promoter to drive the expression of a reporter protein. The transcription activation domain and the DNA-binding domain may be selected from various known transcriptional activators, e.g., GAL4, GCN4, ARD1, the human estrogen receptor, *E. coli* LexA protein, herpes simplex virus VP16 (Triezenberg et al., *Genes Dev.* 2:718-729 (1988)), the *E. coli* B42 protein (acid blob, see Gyuris et al., *Cell,* 75:791-803 (1993)), NF-kB p65, and the like. The reporter gene and the promoter driving its transcription typically are incorporated into a separate reporter vector. Alternatively, the host cells are engineered to contain such a promoter-reporter gene sequence in their chromosomes. Thus, the interaction or lack of interaction between two interacting protein members of a protein complex can be determined by detecting or measuring changes in the reporter in the assay system. Although the reporters and selection markers can be of similar types and used in a similar manner in the present invention, the reporters and selection markers should be carefully selected in a particular detection assay such that they are distinguishable from each other and do not interfere with each other's function.

Many different types reporters are useful in the screening assays. For example, a reporter protein may be a fusion protein having an epitope tag fused to a protein. Commonly used and commercially available epitope tags include sequences derived from, e.g., influenza virus hemagglutinin (HA), Simian Virus 5 (V5), polyhistidine (6×His), c-myc, lacZ, GST, and the like. Antibodies specific to these epitope tags are generally commercially available. Thus, the expressed reporter can be detected using an epitope-specific antibody in an immunoassay.

In another embodiment, the reporter is selected such that it can be detected by a color-based assay. Examples of such reporters include, e.g., the lacZ protein (β-galactosidase), the green fluorescent protein (GFP), which can be detected by fluorescence assay and sorted by flow-activated cell sorting (FACS) (See Cubitt et al., *Trends Biochem. Sci.,* 20:448-455 (1995)), secreted alkaline phosphatase, horseradish peroxidase, the blue fluorescent protein (BFP), and luciferase photoproteins such as aequorin, obelin, mnemiopsin, and berovin (See U.S. Pat. No. 6,087,476, which is incorporated herein by reference).

Alternatively, an auxotrophic factor is used as a reporter in a host strain deficient in the auxotrophic factor. Thus, suitable auxotrophic reporter genes include, but are not limited to, URA3, HIS3, TRP1, LEU2, LYS2, ADE2, and the like. For example, yeast cells containing a mutant URA3 gene can be used as host cells (Ura$^-$ phenotype). Such cells lack URA3-encoded functional orotidine-5'-phosphate decarboxylase, an enzyme required by yeast cells for the biosynthesis of uracil. As a result, the cells are unable to grow on a medium lacking uracil. However, wild-type orotidine-5'-phosphate decarboxylase catalyzes the conversion of a non-toxic compound 5-fluoroorotic acid (5-FOA) to a toxic product, 5-fluorouracil. Thus, yeast cells containing a wild-type URA3 gene are sensitive to 5-FOA and cannot grow on a medium containing 5-FOA. Therefore, when the interaction between the interacting protein members in the fusion proteins results in the expression of active orotidine-5'-phosphate decarboxylase, the Ura$^-$ (Foa$^R$) yeast cells will be able to grow on a uracil deficient medium (SC-Ura plates). However, such cells will not survive on a medium containing 5-FOA. Thus, protein-protein interactions can be detected based on cell growth.

Additionally, antibiotic resistance reporters can also be employed in a similar manner. In this respect, host cells sensitive to a particular antibiotics is used. Antibiotics resistance reporters include, for example, chloramphenicol acetyl transferase (CAT) gene and the kan$^R$ gene, which confers resistance to G418 in eukaryotes and to kanamycin in prokaryotes.

4.3.1.3. Screening Assays for Interaction Antagonists

The screening assay of the present invention is useful in selecting compounds capable of interfering with or disrupting or dissociating protein-protein interaction in the protein complexes of the present invention, i.e., interactions between Tsg101 or a homologue or derivative thereof and HIV GAG, HIV GAGp6, other retroviral GAG containing a P(T/S)AP (SEQ ID NO:1 or SEQ ID NO:3) late domain motif, or a homologue or derivative thereof. For example, Tsg101 and HIV GAG play a role in HIV propagation, and thus are involved in HIV infection and AIDS. It may be possible to ameliorate or alleviate the diseases or disorders in a patient by interfering with or dissociating normal interactions between Tsg101 and HIV GAG. Alternatively, if the disease or disorder is associated with increased expression of Tsg101 and/or HIV GAG in accordance with the present invention, then the disease may be treated or prevented by weakening or dissociating the interaction between Tsg101 and HIV GAG in a patient. In addition, if a disease or disorder is associated with mutant forms of Tsg101 and/or HIV GAG that lead to strengthened protein-protein interaction therebetween, then the disease or disorder may be treated with a compound that weakens or interferes with the interaction between the mutant forms of Tsg101 and HIV GAG.

In a screening assay for interaction antagonists, Tsg101 and HIV GAG or GAGp6, for example, are used as test proteins expressed in the form of fusion proteins as described above for purposes of a two-hybrid assay. The fusion proteins are expressed in a host cell and allowed to interact with each other in the presence of one or more test compounds.

In a preferred embodiment, a counterselectable marker is used as a reporter such that a detectable signal (e.g., appearance of color or fluorescence, or cell survival) is present only when the test compound is capable of interfering with the interaction between the two test proteins. In this respect, the reporters used in various "reverse two-hybrid systems" known in the art may be employed. Reverse two-hybrid systems are disclosed in, e.g., U.S. Pat. Nos. 5,525,490; 5,733,726; 5,885,779; Vidal et al., *Proc. Natl. Acad. Sci. USA*, 93:10315-10320 (1996); and Vidal et al., *Proc. Natl. Acad. Sci. USA*, 93:10321-10326 (1996), all of which are incorporated herein by reference.

Examples of suitable counterselectable reporters useful in a yeast system include the URA3 gene (encoding orotidine-5'-decarboxylase, which converts 5-fluoroorotic acid (5-FOA) to the toxic metabolite 5-fluorouracil), the CAN1 gene (encoding arginine permease, which transports toxic arginine analog canavanine into yeast cells), the GAL1 gene (encoding galactokinase, which catalyzes the conversion of 2-deoxygalactose to toxic 2-deoxygalactose-1-phosphate), the LYS2 gene (encoding α-aminoadipate reductase, which renders yeast cells unable to grow on a medium containing α-aminoadipate as the sole nitrogen source), the MET15 gene (encoding O-acetylhomoserine sulfhydrylase, which confers on yeast cells sensitivity to methyl mercury), and the CYH2 gene (encoding L29 ribosomal protein, which confers sensitivity to cycloheximide). In addition, any known cytotoxic agents including cytotoxic proteins such as the diphtheria toxin (DTA) catalytic domain can also be used as counterselectable reporters. See U.S. Pat. No. 5,733,726. DTA causes the ADP-ribosylation of elongation factor-2 and thus inhibits protein synthesis and causes cell death. Other examples of cytotoxic agents include recin, Shiga toxin, and exotoxin A of *Pseudomonas aeruginosa*.

For example, when the URA3 gene is used as a counterselectable reporter gene, yeast cells containing a mutant URA3 gene can be used as host cells (Ura⁻ Foa$^R$ phenotype) for the in vivo assay. Such cells lack URA3-encoded functional orotidine-5'-phosphate decarboxylase, an enzyme required for the biosynthesis of uracil. As a result, the cells are unable to grow on media lacking uracil. However, because of the absence of a wild-type orotidine-5'-phsphate decarboxylase, the yeast cells cannot convert non-toxic 5-fluoroorotic acid (5-FOA) to a toxic product, 5-fluorouracil. Thus, such yeast cells are resistant to 5-FOA and can grow on a medium containing 5-FOA. Therefore, for example, to screen for a compound capable of disrupting interaction between Tsg101 and HIV GAGp6, Tsg101 can be expressed as a fusion protein with a DNA-binding domain of a suitable transcription activator while HIV GAGp6 is expressed as a fusion protein with a transcription activation domain of a suitable transcription activator. In the host strain, the reporter URA3 gene may be operably linked to a promoter specifically responsive to the association of the transcription activation domain and the DNA-binding domain. After the fusion proteins are expressed in the Ura⁻ Foa$^R$ yeast cells, an in vivo screening assay can be conducted in the presence of a test compound with the yeast cells being cultured on a medium containing uracil and 5-FOA. If the test compound does not disrupt the interaction between Tsg101 and HIV GAG or GAGp6, active URA3 gene product, i.e., orotidine-5'-decarboxylase, which converts 5-FOA to toxic 5-fluorouracil, is expressed. As a result, the yeast cells cannot grow. On the other hand, when the test compound disrupts the interaction between Tsg101 and HIV GAG or GAGp6, no active orotidine-5'-decarboxylase is produced in the host yeast cells. Consequently, the yeast cells will survive and grow on the 5-FOA-containing medium. Therefore, compounds capable of interfering with or dissociating the interaction between Tsg101 and HIV GAG or GAGp6 can thus be identified based on colony formation.

As will be apparent, the screening assay of the present invention can be applied in a format appropriate for large-scale screening. For example, combinatorial technologies can be employed to construct combinatorial libraries of small organic molecules or small peptides. See generally, e.g., Kenan et al., *Trends Biochem. Sc.*, 19:57-64 (1994); Gallop et al., *J. Med. Chem.*, 37:1233-1251 (1994); Gordon et al., *J. Med. Chem.*, 37:1385-1401 (1994); Ecker et al., *Biotechnology*, 13:351-360 (1995). Such combinatorial libraries of compounds can be applied to the screening assay of the present invention to isolate specific modulators of particular protein-protein interactions. In the case of random peptide libraries, the random peptides can be co-expressed with the fusion proteins of the present invention in host cells and assayed in vivo. See e.g., Yang et al., *Nucl. Acids Res.*, 23:1152-1156 (1995). Alternatively, they can be added to the culture medium for uptake by the host cells.

Conveniently, yeast mating is used in an in vivo screening assay. For example, haploid cells of a-mating type expressing one fusion protein as described above are mated with haploid cells of α-mating type expressing the other fusion protein. Upon mating, the diploid cells are spread on a suitable medium to form a lawn. Drops of test compounds can be deposited onto different areas of the lawn. After culturing the lawn for an appropriate period of time, drops containing a compound capable of modulating the interaction between the particular test proteins in the fusion proteins can be identified by stimulation or inhibition of growth in the vicinity of the drops.

The screening assays of the present invention for selecting compounds capable of modulating protein-protein interactions can also be fine-tuned by various techniques to adjust the thresholds or sensitivity of the positive and negative selections. Mutations can be introduced into the reporter proteins to adjust their activities. The uptake of test compounds by the host cells can also be adjusted. For example, yeast high uptake mutants such as the erg6 mutant strains can facilitate yeast uptake of the test compounds. See Gaber et al., *Mol. Cell. Biol.*, 9:3447-3456 (1989). Likewise, the uptake of the selection compounds such as 5-FOA, 2-deoxygalactose, cycloheximide, α-aminoadipate, and the like can also be fine-tuned.

4.4. Virtual Screen and Compound Optimization

Once the test compounds are selected capable of modulating the protein-protein interaction between the interacting partners of a protein complex of the present invention, a data set including data defining the identity or characteristics of the test compounds can be generated. The data set may include information relating to the properties of a selected test compound, e.g., chemical structure, chirality, molecular weight, melting point, etc. Alternatively, the data set may simply include assigned identification numbers understood by the researchers conducting the screening assay and/or researchers receiving the data set as representing specific test compounds. The data or information can be cast in a transmittable form that can be communicated or transmitted to other researchers, particularly researchers in a different country. Such a transmittable form can vary and can be tangible physical manufactures, or intangible electronic signal. For example, the data set defining one or more selected test compounds can be embodied in texts, tables, diagrams, molecular structures, photographs, charts, images or any other visual forms. The data or information can be recorded on a tangible media such as paper or embodied in computer-readable forms (e.g., electronic, electromagnetic, optical or other signals). The data in a computer-readable form can be stored in a computer usable storage medium (e.g., floppy disks, magnetic tapes, optical disks, and the like), and can be retrievable through the execution of a computer program for viewing or displaying the data or information. Alternatively, the data or information in physical manufacture form or electronic signals can be transmitted directly through a communication infrastructure. In particular, the data embodied in electronic signals can be transmitted in the form of email or posted on a website on the Internet or Intranet. In addition, the information or data on a selected test compound can also be recorded in an audio form and transmitted through any suitable media, e.g., analog or digital cable lines, fiber optic cables, etc., via telephone, facsimile, wireless mobile phone, Internet phone and the like.

Thus, the information and data on a test compound selected in a screening assay described above or by virtual screening as discussed below can be produced anywhere in the world and transmitted to a different location. For example, when a screening assay is conducted offshore, the information and data on a selected test compound can be generated and cast in a transmittable form as described above. The data and information in a transmittable form thus can be imported into the U.S. or transmitted to any other countries, where the data and information may be used in further testing the selected test compound and/or in modifying and optimizing the selected test compound to develop lead compounds for testing in clinical trials.

Compounds can also be selected based on structural models of the target protein or protein complex and/or test compounds, e.g., by virtual screen. In addition, once an effective compound is identified, structural analogs or mimetics thereof can be produced based on rational drug design with the aim of improving drug efficacy and stability, and reducing side effects. Methods known in the art for virtual screen and rational drug design can be used in the present invention. See, e.g., Hodgson et al., *Bio/Technology*, 9:19-21 (1991); U.S. Pat. Nos. 5,800,998 and 5,891,628, all of which are incorporated herein by reference. An example of rational drug design is the development of HIV protease inhibitors. See Erickson et al., *Science*, 249:527-533 (1990).

In this respect, structural information on the target protein or protein complex is obtained. Preferably, atomic coordinates defining a three-dimensional structure of the target protein or protein complex are obtained. For example, each of the interacting pair can be expressed and purified. The purified interacting protein pairs are then allowed to interact with each other in vitro under appropriate conditions. Optionally, the interacting protein complex can be stabilized by crosslinking or other techniques. The interacting complex can be studied using various biophysical techniques including, e.g., X-ray crystallography, NMR, computer modeling, mass spectrometry, and the like. Methods for obtaining such atomic coordinates by X-ray crystallography, NMR, and the like are known in the art and the application thereof to the target protein or protein complex of the present invention should be apparent to skilled persons in the art of structural biology. See Smyth and Martin, *Mol. Pathol.*, 53:8-14 (2000); Oakley and Wilce, *Clin. Exp. Pharmacol. Physiol.*, 27(3):145-151 (2000); Ferentz and Wagner, *Q. Rev. Biophys.*, 33:29-65 (2000); and Roberts, *Curr. Opin. Biotechnol.*, 10:42-47 (1999).

In addition, understanding of the interaction between the proteins of interest in the presence or absence of a modulator compound can also be derived from mutagenesis analysis using yeast two-hybrid system or other methods for detecting protein-protein interaction. In this respect, various mutations can be introduced into the interacting proteins and the effect of the mutations on protein-protein interaction is examined by a suitable method such as the yeast two-hybrid system.

Various mutations including amino acid substitutions, deletions and insertions can be introduced into a protein sequence using conventional recombinant DNA technologies. Generally, it is particularly desirable to decipher the binding sites. Thus, it is important that the mutations introduced only affect protein-protein interaction or protein-compound interaction and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein-protein interactions. Alternatively, the "alanine scanning mutagenesis" technique is used. See Wells, et al., *Methods Enzymol.*, 202:301-306 (1991); Bass et al., *Proc. Natl. Acad. Sci. USA*, 88:4498-4502 (1991); Bennet et al., *J. Biol. Chem.*, 266:5191-5201 (1991); Diamond et al., *J. Virol.*, 68:863-876 (1994). Using this technique, charged or hydrophobic amino acid residues of the interacting proteins are replaced by alanine, and the effect on the interaction between the proteins is analyzed using e.g., the yeast two-hybrid system. For example, the entire protein sequence can be scanned in a window of five amino acids. When two or more charged or hydrophobic amino acids appear in a window, the charged or hydrophobic amino acids are changed to alanine using standard recombinant DNA techniques. The thus mutated proteins are used as "test proteins" in the above-described two-hybrid assay to examine the effect of the mutations on protein-protein interaction. Preferably, the mutagenesis analysis is conducted both in the presence and in the absence of an identified modulator compound. In this manner, the domains or residues of the proteins important to protein-protein interaction and/or the interaction between the modulator compound and the proteins can be identified. Likewise, interactions between a selected compound and a target protein (e.g., Tsg101) can also be studied by mutagenesis of the target protein.

Based on the structural information obtained, structural relationships between the interacting proteins, between a selected compound and the interacting proteins, or between a selected compound and a target protein are elucidated. The moieties and the three-dimensional structure of the selected compound critical to its modulating effect on the interaction of the proteins of interest or on a target protein are revealed.

Medicinal chemists can then design analog compounds having similar moieties and structures.

In addition, an identified peptide compound capable of modulating a particular protein-protein interaction or a particular target protein can also be analyzed by the alanine scanning technique and/or a screening assay to determine the domains or residues of the peptide important to its modulating effect on a particular protein-protein interaction or a particular target protein. The peptide compound can be used as a lead molecule for rational design of small organic molecules or peptide mimetics. See Huber et al., *Curr. Med. Chem.*, 1:13-34 (1994).

The residues or domains critical to the modulating effect of the identified compound constitute the active region of the compound known as its "pharmacophore."

Once the pharmacophore has been elucidated, a structural model can be established by a modeling process that may incorporate data from NMR analysis, X-ray diffraction data, alanine scanning, spectroscopic techniques and the like. Various techniques including computational analysis, similarity mapping and the like can all be used in this modeling process. See e.g., Perry et al., in *OSAR: Quantitative Structure-Activity Relationships in Drug Design*, pp. 189-193, Alan R. Liss, Inc., 1989; Rotivinen et al., *Acta Pharmaceutical Fennica*, 97:159-166 (1988); Lewis et al., *Proc. R. Soc. Lond.*, 236:125-140 (1989); McKinaly et al., *Annu. Rev. Pharmacol. Toxiciol.*, 29:111-122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed. The compounds identified in accordance with the present invention can be incorporated into a pharmaceutical formulation suitable for administration to an individual.

In addition, the structural models or atomic coordinates defining a three-dimensional structure of the target protein or protein complex can also be used in virtual screen to select compounds capable of modulating the target protein or protein complex. Various methods of computer-based virtual screen using atomic coordinates are generally known in the art. For example, U.S. Pat. No. 5,798,247 (which is incorporated herein by reference) discloses a method of identifying a compound (specifically, an interleukin converting enzyme inhibitor) by determining binding interactions between an organic compound and binding sites of a binding cavity within the target protein. The binding sites are defined by atomic coordinates.

Thus, as will be apparent to a skilled artisan, atomic coordinates defining a three-dimensional structure of a target protein or protein complex of the present invention can be provided by any methods known in the art. Compounds can then be designed or selected based on the atomic coordinates.

5. Therapeutic Applications

In accordance with another aspect of the present invention, methods are provided for modulating a protein complex comprising Tsg101 and HIV GAG or GAGp6 in human cells. The human cells can be in in vitro cell or tissue cultures. The methods are also applicable to human cells in a patient.

In one embodiment, the concentration of a protein complex having Tsg101 interacting with HIV GAG or GAGp6 is reduced in the cells. Various methods can be employed to reduce the concentration of the protein complex. The protein complex concentration can be reduced by interfering with the interactions between Tsg101 and HIV GAG or GAGp6. For example, compounds capable of interfering with interactions between Tsg101 and HIV GAG or GAGp6 can be administered to the cells in vitro or in vivo in a patient. Such compounds can be compounds capable of binding Tsg101 protein, particularly the UEV domain of Tsg101 protein, or HIV GAG or GAGp6. They can also be antibodies immunoreactive with the Tsg101 protein or HIV GAG or GAGp6. Preferably, antibodies that bind to the UEV domain of the Tsg101 protein are used. Also, the compounds can be small peptides derived from the HIV GAG or GAGp6 protein or mimetics thereof capable of binding Tsg101, or small peptides derived from Tsg101 protein or mimetics thereof capable of binding HIV GAG or GAGp6.

In another embodiment, the method of modulating the protein complex includes inhibiting the expression of Tsg101 protein and/or HIV GAG or GAGp6 protein. The inhibition can be at the transcriptional, translational, or post-translational level. For example, antisense compounds and ribozyme compounds can be administered to human cells in cultures or in human bodies.

In the various embodiments described above, preferably the concentrations or activities of both Tsg101 protein and HIV GAG or GAGp6 are reduced or inhibited.

In yet another embodiment, an antibody selectively immunoreactive with a protein complex having Tsg101 interacting with HIV GAG or GAGp6 is administered to cells in vitro or in human bodies to inhibit the protein complex activities and/or reduce the concentration of the protein complex in the cells or patient.

The methods for modulating the protein complex comprising Tsg101 and HIV GAG or GAGp6 as provided according to the present invention can be used to inhibit HIV viral budding from infected host cells. When multiple cells are present, e.g., in cell culture or in a patient's body, the inhibition of viral budding prevents the viruses from being released from the infected host cells thereby suppressing further viral propagation. Accordingly, the present invention also encompasses methods of treating HIV infection and preventing AIDS in patients by reducing the concentration or inhibiting the activities of protein complexes having Tsg101 and HIV GAG or GAGp6, or by reducing the concentration or inhibiting the activities of Tsg101 or of HIV GAG or GAGp6.

In addition, the methods for modulating the protein complex comprising Tsg101 and HIV GAG or GAGp6 can also be useful in inhibiting the budding of many other viruses, particularly those viruses whose budding from infected host cells is dependent on the late domain motif P(T/S)AP (SEQ ID NO:1 or SEQ ID NO:3). As described above, the P(T/

S)AP (SEQ ID NO:1 or SEQ ID NO:3) motif, which is responsible for HIV GAGp6's interaction with Tsg101, is conserved among the GAGp6 domains of all known primate lentiviruses. In non-primate lentiviruses, which lack a GAGp6 domain, the P(T/S)AP (SEQ ID NO:1 or SEQ ID NO:3) motif is at the immediate C terminus of the GAG polyprotein. In addition, many other retroviruses also contain the P(T/S)AP (SEQ ID NO:1 or SEQ ID NO:3) late domain motif in their GAG polypeptides, which are believed to also interact with Tsg101 in the same manner as the HIV GAGp6 protein.

Accordingly, the present invention also provides methods for modulating a protein complex containing Tsg101 protein and a human retrovirus (other than HIV) GAG polypeptide or a fragment thereof containing a P(T/S)AP (SEQ ID NO:1 or SEQ ID NO:3) late domain motif. Such modulating methods can be used in inhibiting the budding of such a virus from its infected host cells and in treating infections by such a virus in patients.

In addition, the present invention also encompasses methods for modulating a protein complex containing a Tsg101 protein ortholog and a non-human retrovirus GAG polypeptide or a fragment thereof containing a P(T/S)AP (SEQ ID NO:1 or SEQ ID NO:3) late domain motif. Such modulating methods can be used in inhibiting the budding of such non-human retroviruses from their infected animal host cells and in treating infections by such viruses in animals.

Examples of such non-human retroviruses include, but are not limited to, primate lentiviruses other than HIV and non-primate lentiviruses (except for EIAV). As is known in the art, lentiviruses are a group of retroviruses capable of long-term latent infection of vertebrate cells. They replicate in host cells only when activated. Lentiviruses typically have enveloped virions. Non-primate lentiviruses include bovine lentiviruses (e.g. bovine immunodeficiency virus (BIV), Jembrana disease virus), feline lentiviruses (e.g. feline immunodeficiency virus (FIV) which causes immunodeficiency, wasting, and encephalitis in cats), ovine/caprine lentivirus (e.g. caprine arthritis-encephalitis virus (CAEV) which causes anemia and wasting in goats, ovine lentivirus, Visna virus which causes pneumonia, wasting, encephalitis and arthritis), and Equine lentiviruses (e.g. Equine infectious anemia virus (EIAV), which infects horses causing arthritis and encephalitis). Examples of non-human primate lentiviruses include various simian immunodeficiency viruses that infect hosts such as chimpanzee, mangabey, African Green monkey, mandrill, L'Hoest, Sykes' monkey, or Guereza Colobus monkey.

The methods for modulating a protein complex containing Tsg101 protein and a human retrovirus GAG polypeptide or a fragment thereof containing a P(T/S)AP (SEQ ID NO:1 or SEQ ID NO:3) late domain motif and the methods for modulating a protein complex containing a Tsg101 protein ortholog and a non-human retrovirus GAG polypeptide or a fragment thereof containing a P(T/S)AP (SEQ ID NO:1 or SEQ ID NO:3) late domain motif should be performed in a manner similar to those described above in the context of modulating a protein complex of Tsg101 and HIV GAG or GAGp6. Likewise, the methods for treating infection by such other human or non-human viruses should be similar to the methods for treating HIV infection, as will be apparent to skilled artisans apprised of the present disclosure.

Specifically, the concentration of the protein complexes can be reduced in the cells by various methods. For example, the protein complex concentration can be reduced by interfering with the interactions between Tsg101 protein and a human retrovirus GAG polypeptide or a fragment thereof containing a P(T/S)AP (SEQ ID NO:1 or SEQ ID NO:3) late domain motif, or the interactions between a Tsg101 protein ortholog and non-human retroviruses GAG polypeptide or a fragment thereof containing a P(T/S)AP (SEQ ID NO:1 or SEQ ID NO:3) late domain motif. Compounds capable of interfering with the interactions can be administered to cells in vitro or in vivo in a subject to be treated. Such compounds can be compounds capable of binding Tsg101 protein or the Tsg101 protein ortholog, particularly the UEV domain of Tsg101 protein or the Tsg101 protein ortholog. They can also be antibodies immunoreactive with Tsg101 protein or the Tsg101 protein ortholog. Preferably, antibodies that bind to the UEV domain of the Tsg101 protein or the Tsg101 protein ortholog are used. Also, the compounds can be small peptides derived from a retrovirus GAG polypeptide, preferably including the amino acid residues spanning the P(T/S)AP (SEQ ID NO:1 or SEQ ID NO:3) late domain motif. In addition, antibodies selectively immunoreactive with the protein complexes can be administered. In other embodiments, the expression of Tsg101 protein or a Tsg101 ortholog is inhibited. The inhibition can be at the transcriptional, translational, or post-translational level. For example, antisense compounds and ribozyme compounds can be administered to cells in culture or in the subject to be treated.

The details of the various methods for modulating the protein complexes or protein-protein interactions and methods for treating virus infection are described below. Although such details are described in the context of interactions between Tsg101 protein and HIV GAG or GAGp6 and HIV infection in human cells, the analogous methods with respect to infections by other viruses should be apparent to skilled artisans apprised of the present disclosure.

5.1. Antibody Therapy

In one embodiment, an antibody may be administered to cells or tissue in vitro or in a patient. The antibody administered may be immunoreactive with Tsg101 or HIV GAG or GAGp6. Suitable antibodies may be monoclonal or polyclonal that fall within any antibody classes, e.g., IgG, IgM, IgA, etc. The antibody suitable for this invention may also take a form of various antibody fragments including, but not limited to, Fab and F(ab')$_2$, single-chain fragments (scFv) ("single-chain antibodies"), and the like. In one embodiment, an antibody selectively immunoreactive with the protein complex formed from Tsg101 and HIV GAG or GAGp6 in accordance with the present invention is administered to cells or tissue in vitro or in a patient. In another embodiment, an antibody specific to Tsg101 is administered to cells or tissue in vitro or in a patient. Preferably, an antibody specific to the UEV domain of Tsg101 is administered to cells or tissue in vitro or in a patient. Methods for making the antibodies of the present invention should be apparent to a person of skill in the art, especially in view of the discussions in Section 3 above. The antibodies can be administered in any suitable form and route as described in Section 6 below. Preferably, the antibodies are administered in a pharmaceutical composition together with a pharmaceutically acceptable carrier.

Alternatively, the antibodies may be delivered by a gene-therapy approach. That is, nucleic acids encoding the antibodies, particularly single-chain fragments (scFv), may be introduced into cells or tissue in vitro or in a patient such that desirable antibodies may be produced by recombinant expression in vivo from the nucleic acids. For this purpose, the nucleic acids with appropriate transcriptional and translation regulatory sequences can be directly administered into the patient. Alternatively, the nucleic acids can be incorporated into a suitable vector as described in Sections 4 and 5.5 and delivered into cells or tissue in vitro or in a patient along with the vector. The expression vector containing the nucleic acids can be administered directly to a patient. It can also be introduced into cells, preferably cells derived from a patient to be treated, and subsequently delivered into the patient by cell transplantation. See Section 5.5 below.

5.2. Inducing Degradation of Tsg101 Transcript

Nucleic acids that induce degradation of RNA transcripts encoding Tsg101 can also be administered to cells to reduce Tsg101 protein level or the level of protein complexes containing Tsg101, including protein complexes formed by Tsg101 and HIV GAG. As used herein, the term "nucleic acids that induce degradation of RNA transcripts encoding Tsg101" means any nucleic acid molecule, modified nucleic acid molecule, or nucleic acid molecule analog, that results in the reduction of concentrations of mRNA or pre-mRNA encoding the Tsg101 protein inside a cell. Such nucleic acid molecules can be RNAs that act by inducing RNA interference (RNAi)—the double-stranded RNA-directed degradation of endogenous transcripts of corresponding sequence. Alternatively, such nucleic acid molecules can be enzymatic nucleic acids, RNA molecules, DNA molecules, or derivatives or analogs thereof, that directly cleave RNA transcripts encoding Tsg101. Additionally, such nucleic acid molecules can also be antisense oligonucleotides that specifically hybridize with mRNA or pre-mRNA encoding the Tsg101 and promote the cleavage and degradation of these transcripts by cellular endonucleases, such as ribonuclease-H (RNase-H).

As used herein "RNA transcripts encoding Tsg101" means RNA transcribed from the Tsg101 gene, including unspliced, or partially spliced, pre-mRNAs and spliced, or mature, mRNAs. Such transcripts encode the Tsg101 protein, and therefore contain Tsg101 coding sequence, as well as other sequences such as 5' and 3' untranslated regions, and exons, in the case of pre-mRNAs. It should be understood that, "RNA transcripts encoding Tsg101" also includes any naturally occurring polymorphic variants of RNA transcripts encoding Tsg101.

As used herein "nucleic acid molecules that induce the degradation of RNA transcripts encoding Tsg101" are understood to include RNA molecules, DNA molecules, and analogs and modified forms thereof. The "nucleic acid molecules that induce the degradation of RNA transcripts encoding Tsg101" of the present invention are provided such that, when introduced into cells, they result in the reduction of RNA transcripts encoding Tsg101 by at least 20%, as measured by quantitative RT-PCR, and/or result in the reduction of cellular Tsg101 protein levels at least a 20%, as measured by quantitative Western Blot.

Confirmation that a nucleic acid molecule is a "nucleic molecules that induces degradation of RNA transcripts encoding Tsg101" can be obtained by demonstrating a quantitative reduction in transcripts encoding Tsg101, or a reduction in Tsg101 protein itself, using any method known in the art. However, a preferred method for demonstrating a quantitative reduction in transcripts encoding Tsg101 is "Real-Time Quantitative RT-PCR," as described in a publication by Winer et al. (*Anal. Biochem* 270:41-49 (1999)), which is incorporated by reference in is entirety. Similarly, a preferred method for demonstrating a quantitative reduction in Tsg101 protein is quantitative Western Blot analysis, as described in a publication by Gingrich et al., (*BioTechniques* 29:636-642 (2000)). Primary antibody specifically immunoreactive to Tsg101, which can be used for quantitative Western Blot analysis of Tsg101 is commercially available (e.g., BD Biosciences/Pharmingen (San Diego, Calif., USA)). This same antibody can also be used for enzyme-linked immunosorbent assays (ELISAs) designed to quantitate Tsg101 protein.

Importantly, in order to determine the amount of reduction of RNA transcripts encoding Tsg101, and/or the amount of cellular Tsg101 protein levels, one must first conduct a control experiment to determine transcript and/or protein levels prior to, or in the absence of, treatment by the nucleic acid molecules of the present invention. Such a control experiment allows for the establishment of "baseline" levels, against which the nucleic acid induced reduction of transcript and/or protein levels can be measured.

Furthermore, methods to quantitate mRNA or protein expression levels generally require that the results obtained be normalized for differences in the amount of total RNA or total protein in the sample to be quantitated. Generally, normalization is achieved by quantitating an internal standard such as the products of a ubiquitously expressed housekeeping gene. For example, normalization of quantitative RT-PCR assays can be achieved by simultaneously quantitating mRNA encoding glyceraldehyde-3-phosphate dehydrogenase (GAPDH), which is expressed at generally invariant levels in different cell types under different treatment conditions (Winer et al., *Anal. Biochem.* 270:41-49 (1999)). Differences in the levels of GAPDH mRNA determined are representative of different amounts of input mRNA templates between reactions, and can be used as an internal standard by which to adjust levels of the quantitated transcript, to adjust for such differences in input mRNA templates. Similarly, the levels of GAPDH protein can be used to normalize for differences in the amounts of input total protein during protein quantitation assays.

5.2.1. Antisense Therapy

In one embodiment, antisense compounds specific to nucleic acids encoding one or more interacting protein members of a protein complex identified in the present invention is administered to cells or tissue in vitro or in a patient to be therapeutically or prophylactically treated. The antisense compounds should specifically inhibit the expression of the one or more interacting protein members. In preferred embodiments, antisense compounds specifically hybridizing to a Tsg101 nucleic acid is administered. As is known in the art, antisense drugs generally act by hybridizing to a particular target nucleic acid thus blocking gene expression. Methods for designing antisense compounds and using such compounds in treating diseases are well known and well developed in the art. For example, the antisense drug Vitravene® (fomivirsen), a 21-base long oligonucleotide, has been successfully developed and marketed by Isis Pharmaceuticals, Inc. for treating cytomegalovirus (CMV)-induced retinitis.

Any methods for designing and making antisense compounds may be used for purpose of the present invention. See generally, Sanghvi et al., eds., *Antisense Research and Applications*, CRC Press, Boca Raton, 1993. Typically, antisense compounds are oligonucleotides designed based on the nucleotide sequence of the mRNA or gene of one or more of the interacting protein members of a particular protein complex of the present invention. In particular, antisense compounds can be designed to specifically hybridize to a particular region of the gene sequence or mRNA of one or more of the interacting protein members to modulate (increase or decrease), replication, transcription, or translation. As used herein, the term "specifically hybridize" or paraphrases thereof means a sufficient degree of complementarity or pairing between an antisense oligo and a target DNA or mRNA such that stable and specific binding occurs therebetween. In particular, 100% complementary or pairing is not required. Specific hybridization takes place when sufficient hybridization occurs between the antisense compound and its intended target nucleic acids in substantially absence of non-specific binding of the antisense compound to non-target sequences under predetermined conditions, e.g., for purposes of in vivo treatment, preferably under physiological conditions. Preferably, specific hybridization results in the interference with normal expression of the target DNA or mRNA.

For example, an antisense oligo can be designed to specifically hybridize to the replication or transcription regulatory regions of a target gene, or the translation regulatory regions such as translation initiation region and exon/intron junctions, or the coding regions of a target mRNA. Preferably, Tsg101 gene or Tsg101 mRNA is used as the target.

As is generally known in the art, commonly used oligonucleotides are oligomers or polymers of ribonucleic acid or deoxyribonucleic acid having a combination of naturally-occurring nucleoside bases, sugars and covalent linkages between nucleoside bases and sugars including a phosphate group. However, it is noted that the term "oligonucleotides" also encompasses various non-naturally occurring mimetics and derivatives, i.e., modified forms, of naturally-occurring oligonucleotides as described below. Typically an antisense compound of the present invention is an oligonucleotide having from about 6 to about 200, preferably from about 8 to about 30 nucleoside bases.

The antisense compounds preferably contain modified backbones or non-natural internucleoside linkages, including but not limited to, modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is herein incorporated by reference.

Another useful modified oligonucleotide is peptide nucleic acid (PNA), in which the sugar-backbone of an oligonucleotide is replaced with an amide containing backbone, e.g., an aminoethylglycine backbone. See U.S. Pat. Nos. 5,539,082 and 5,714,331; and Nielsen et al., Science, 254, 1497-1500 (1991), all of which are incorporated herein by reference. PNA antisense compounds are resistant to RNAse H digest and thus exhibit longer half-life. In addition, various modifications may be made in PNA backbones to impart desirable drug profiles such as better stability, increased drug uptake, higher affinity to target nucleic acid, etc.

Alternatively, the antisense compounds are oligonucleotides containing modified nucleosides, i.e., modified purine or pyrimidine bases, e.g., 5-substituted pyrimidines, 6-azapyrimidines, and N-2, N-6 and O-substituted purines, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, each of which is incorporated herein by reference in its entirety.

In addition, oligonucleotides with substituted or modified sugar moieties may also be used. For example, an antisense compound may have one or more 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,053 5,639,873; 5,646,265; 5,658,873; 5,670,633; and 5,700,920, each of which is herein incorporated by reference.

Other types of oligonucleotide modifications are also useful including linking an oligonucleotide to a lipid, phospholipid or cholesterol moiety, cholic acid, thioether, aliphatic chain, polyamine, polyethylene glycol (PEG), or a protein or peptide. The modified oligonucleotides may exhibit increased uptake into cells, improved stability, i.e., resistance to nuclease digestion and other biodegradations. See e.g., U.S. Pat. No. 4,522,811; Burnham, *Am. J. Hosp. Pharm.*, 15:210-218 (1994).

Antisense compounds can be synthesized using any suitable methods known in the art. In fact, antisense compounds may be custom made by commercial suppliers. Alternatively, antisense compounds may be prepared using DNA synthesizers commercially from various vendors, e.g., Applied Biosystems Group of Norwalk, Conn.

The antisense compounds can be formulated into a pharmaceutical composition with suitable carriers and administered into cells or tissue in vitro or in a patient using any suitable route of administration. Alternatively, the antisense compounds may also be used in a "gene-therapy" approach. That is, the oligonucleotide is subcloned into a suitable vector and transformed into human cells. The antisense oligonucleotide is then produced in vivo through transcription. Methods for gene therapy are disclosed in Section 6.3.2 below.

For purposes of the present invention, antisense compounds can be designed and made according the Tsg101 mRNA sequence surrounding the initiation codon or the stop codon. For example, the nucleotide sequence surrounding the initiation codon and the nucleotide sequences of several exemplary antisense compounds are shown in Table 2 below.

TABLE 2

| Tsg101 Selected Antisense Sequence | | |
|---|---|---|
| Target Sequence | 5'-GCAGGGGGCCGTCATGGGGGTGTCGGAGAG-3' | (SEQ ID NO:33) |
| Antisense #1 | 5'-ACCGCCATGACGGCCGCC-3' | (SEQ ID NO:33) |
| Antisense #2 | 5'-CAGCGGCATGACGGCCGC-3' | (SEQ ID NO:34) |
| Antisense #3 | 5'-ACACCGCCATGAGGGGCG-3' | (SEQ ID NO:35) |
| Antisense #4 | 5'-CAGGGGCATGACGGCCGCCT-3' | (SEQ ID NO:36) |
| Antisense #5 | 5'-ACACCGCCATGACGGCCGGC-3' | (SEQ ID NO:37) |
| Antisense #6 | 5'-GACACGGCCATGACGGCCGG-3' | (SEQ ID NO:38) |
| Antisense #7 | 5'-AGAGCGCCATGACGGGCGCCTG3' | (SEQ ID NO:39) |
| Antisense #8 | 5'-GACACCGCCATGAGGGCCGCCT-3' | (SEQ ID NO:40) |
| Antisense #9 | 5'-CGACACCGCCATGACGGCGGCG-3' | (SEQ ID NO:41) |

5.2.2. Ribozyme Therapy

In another embodiment, an enzymatic RNA or ribozyme is designed to target the nucleic acids encoding one or more of the interacting protein members of the protein complex of the present invention. In preferred embodiments, Tsg101 nucleic acids are targeted. Ribozymes are RNA molecules, which have an enzymatic activity and are capable of repeatedly cleaving other separate RNA molecules in a nucleotide base sequence specific manner. See Kim et al., *Proc. Natl. Acad. of Sci. USA*, 84:8788 (1987); Haseloff and Gerlach, *Nature*, 334:585 (1988); and Jefferies et al., *Nucleic Acid Res.*, 17:1371 (1989). A ribozyme typically has two portions: a catalytic portion and a binding sequence that guides the binding of ribozymes to a target RNA through complementary base-pairing. Once the ribozyme is bound to a target RNA, it enzymatically cleaves the target RNA, typically destroying its ability to direct translation of an encoded protein. After a ribozyme has cleaved its RNA target, it is released from that target RNA and thereafter can bind and cleave another target. That is, a single ribozyme molecule can repeatedly bind and cleave new targets. Therefore, one advantage of ribozyme treatment is that a lower amount of exogenous RNA is required as compared to conventional antisense therapies. In addition, ribozymes exhibit less affinity to mRNA targets than DNA-based antisense oligos, and therefore are less prone to bind to wrong targets.

In accordance with the present invention, a ribozyme may target any portions of the mRNA of one or more interacting protein members including Tsg101 and HIV GAG. Methods for selecting a ribozyme target sequence and designing and making ribozymes are generally known in the art. See e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable ribozymes may be designed in various configurations such as hammerhead motifs, hairpin motifs, hepatitis delta virus motifs, group I intron motifs, or RNase P RNA motifs. See e.g., U.S. Pat. Nos. 4,987,071; 5,496,698; 5,525, 468; 5,631,359; 5,646,020; 5,672,511; and 6,140,491; Rossi et al., *AIDS Res. Human Retroviruses* 8:183 (1992); Hampel and Tritz, *Biochemistry* 28:4929 (1989); Hampel et al., *Nucleic Acids Res.*, 18:299 (1990); Perrotta and Been, *Biochemistry* 31:16 (1992); and Guerrier-Takada et al., *Cell*, 35:849 (1983).

Ribozymes can be synthesized by the same methods used for normal RNA synthesis. For example, such methods are disclosed in Usman et al., *J. Am. Chem. Soc.*, 109:7845-7854 (1987) and Scaringe et al., *Nucleic Acids Res.*, 18:5433-5441 (1990). Modified ribozymes may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature*, 344:565 (1990); Pieken et al., *Science*, 253:314 (1991); and Usman and Cedergren, *Trends in Biochem. Sci.*, 17:334 (1992).

Ribozymes of the present invention may be administered to cells by any known methods, e.g., disclosed in International Publication No. WO 94/02595. For example, they can be administered directly to cells or tissue in vitro or in a patient through any suitable route, e.g., intravenous injection. Alternatively, they may be delivered in encapsulation in liposomes, by iontophoresis, or by incorporation into other vehicles such as hydrogels, cyclodextrins, biodegradable nanocapsules, and bioadhesive microspheres. In addition, they may also be delivered by gene therapy approach, using a DNA vector from which the ribozyme RNA can be transcribed directly. Gene therapy methods are disclosed in detail below in Section 6.3.2.

5.2.3. siRNA Inhibition

In another embodiment, siRNA molecules specific to nucleic acids encoding one or more interacting protein members of a protein complex identified in the present invention is administered to cells or tissue in vitro or in a patient to be therapeutically or prophylactically treated. In particular, siRNA targeting Tsg101 or HIV GAG mRNA can be administered to cells to reduce Tsg101 expression level and inhibit viral budding. The process of siRNA-directed degradation of an RNA transcript of corresponding sequence is referred to as RNA interference, RNAi, or, more generally, "knocking down the expression" or "silencing" of gene expression. Practically, siRNA-directed or induced RNAi leads to the degradation of the targeted transcript, and a corresponding decrease in cellular levels of the gene product that it encodes.

siRNAs are short intermolecular duplexes, generally composed of two distinct (sense and antisense) strands of RNA, each of approximately 21 nucleotides, that form approximately 19 base-pairs, with single stranded 3' overhangs of 1-3, preferably 2 nucleotides. The base-paired region of siRNAs generally substantially corresponds, preferably exactly, to a "target sequence" and its complement, in the RNA transcript to be targeted for degradation.

The specific features of siRNAs required for inducing the efficient degradation or silencing of corresponding RNA transcripts have been systematically investigated, as have the features of the target sequence within the targeted transcript. The results of such experiments have been published and general "rules" have been established for the design of effective siRNA molecules (see: Tuschl et al., *Genes & Dev.* 13:3191-3197 (1999) and Elbashir et al., *EMBO J.* 20:6877-6888 (2001), and discussions in "The siRNA User Guide" at http://www.mpibpc.gwdg.de/abteilungen/100/105/sirna.html).

Generally, the most effective silencing is obtained with siRNA duplexes composed of 21 nucleotide sense and antisense strands that are paired in a manner to produce 2 nucleotide 3' overhangs. The sequence of the overhangs makes only a small contribution to the overall specificity of target recognition, but the identity of the nucleotide adjacent to the paired region can have an effect. In addition, the 3' overhangs can be composed either ribonucleotides or 2'-deoxyribonucleotides, with no apparent differences in efficacy, however siRNAs with 2'-deoxyribonucleotide overhangs may be more resistant to cellular nucleases.

Target sequences in targeted RNA transcripts preferably have the sequence AA(19N)UU, where N=any nucleotide, but can be any contiguous 19 nucleotides. Importantly, target sequences must be chosen from the sequences present in mature mRNAs, but can reside in either coding or non-coding regions. Preferably the target sequence chosen is readily "accessible," to the siRNA, that is, not involved in a stable base-paired structure within the mature transcript, and not specifically bound by an RNA-binding protein. RNA folding algorithms, such as the "Sfold" algorithm developed by Ding and Lawrence (described in *Nucleic Acids Res.* 29:1034-1046 (2001)), which is incorporated by reference in its entirety) can be useful for picking target sequences that have a greater likelihood of being accessibly, and therefore efficiently targeted by a corresponding siRNA, resulting in degradation of the targeted transcript and reduction in the cellular concentration of its encoded gene product.

The individual single-stranded RNAs comprising siRNAs can either be synthesized outside of cells (exogenously), or within cells (endogenously). The two complementary single strands must then anneal to form an RNA duplex—the siRNA. The annealing step can also occur exogenously or endogenously. Exogenously synthesized single-stranded RNAs can be synthesized either chemically, for example using phosphoramidite chemistry, or can be synthesized enzymatically, using an RNA polymerase and a DNA template containing an appropriate promoter sequence just upstream of the template sequence. Exogenously synthesized single-stranded RNAs must generally be purified to some degree, before they can be annealed to form siRNA duplexes. Endogenously synthesized single-stranded RNAs are synthesized by cellular RNA polymerases using a DNA template that contains an appropriate promoter sequence just 5' (upstream) of the template sequence.

Small hairpin RNAs, or shRNAs, are single-stranded RNAs with regions of self-complementarity that can pair with one another, allowing the single strand to fold into an intramolecular duplex with a stem-loop type structure. Although the unpaired loop region can theoretically be any size, it is advantageous for the loop to be small enough to readily allow the self-complementary sequences within the same single-stranded RNA to find each other and basepair. Preferred loop sizes are from 3 to 9 nucleotides, and larger, with loops of 6-9 nucleotides being most preferred. Generally the sequence of the loop is not important, however, it should not consist of palindromic sequence, nor should it be related to sequences adjacent to the target sequence, which is represented by one of the paired complementary regions, and which the shRNA ultimately targets. Within the cell the loop of an shRNAs is cleaved and an intermolecular duplex, not unlike an siRNA, is formed. The stem region of the shRNA should generally contain approximately 19 base pairs, and generally 3' end of the shRNA extending beyond the paired region is composed of multiple thymidylate residues. The base-paired regions of shRNAs generally correspond substantially, preferably exactly, to a "target sequence" and its complement in the RNA transcript to be targeted for degradation, just as the base-paired region in siRNAs does.

Like the single strands of siRNAs, shRNAs can be can be synthesized either endogenously, or exogenously. Endogenously synthesized shRNAs are generally synthesized by cellular RNA polymerases using a DNA template that contains an appropriate promoter sequence just 5' (upstream) of the template sequence. Exogenously synthesized shRNAs can be synthesized either chemically, for example using phosphoramidite chemistry, or can be synthesized enzymatically, using an RNA polymerase and a DNA template containing an appropriate promoter sequence just upstream of the template sequence. Exogenously synthesized shRNAs must generally be purified to some degree, before they can be used to induce RNAi and the degradation of an RNA transcript of corresponding sequence.

The DNA template containing a promoter and the template sequence used to direct the enzymatic synthesis of siRNAs or shRNAs, and optionally a transcription termination sequence, is commonly referred to as an expression cassette. Such expression cassettes can be incorporated into vector DNAs, such as circular plasmids, or viral vectors of various types that can be packaged into modified viral particles to facilitate viral transduction of the cassette into cells. Alternatively, expression cassettes can be readily designed and produced by incorporating them into the linear products of a polymerase chain reaction (PCR), which can be transfected into cells to direct the expression of siRNAs or shRNAs in vivo (e.g., Castanotto et al., *RNA* 8:1454-1460 (2002)). Such PCR products containing expression cassettes can be readily produced in large numbers during PCR, and different template sequences can be incorporated into the cassettes.

Several U.S. and P.C.T. Patent Application Publications teach preferred methods for designing, synthesizing, purifying, and delivering siRNAs and shRNAs into cells. In particular, U.S. Patent Application Publication US 2003/0148519, which is incorporated by reference herein in its entirety, provides compositions and methods for intracellular expression and delivery of siRNAs and shRNAs in mammalian cells; and U.S. Patent Application Publication US 2002/0132788, which is incorporated by reference herein in its entirety, provides a process for delivering siRNAs into cells in vivo for the purpose of inhibiting gene expression in those cells.

Indeed, in vivo inhibition of specific gene expression by RNAi has been achieved in variety of organisms including mammals. For example, Song et al., *Nature Medicine,* 9:347-351 (2003) discloses that intravenous injection of Fas siRNA compounds into laboratory mice with autoimmune hepatitis specifically reduced Fas mRNA levels and expression of Fas protein in mouse liver cells. The gene silencing effect observed persisted without diminution for 10 days after the intravenous injection. The injected siRNA was effective in protecting the mice from liver failure and fibrosis (Song et al., Nature Medicine, 9:347-351 (2003)). Several other approaches for delivery of siRNA into animals have also proved to be successful. See e.g., McCaffery et al., Nature, 418:38-39 (2002); Lewis et al., Nature Genetics, 32:107-108 (2002); and Xia et al., Nature Biotech., 20:1006-1010 (2002).

The siRNA compounds provided according to the present invention can be synthesized using conventional RNA synthesis methods. For example, they can be chemically synthesized using appropriately protected ribonucleoside phosphoramidites and conventional DNA/RNA synthesizer. Various applicable methods for RNA synthesis are disclosed in, e.g., Usman et al., J. Am. Chem. Soc., 109:7845-7854 (1987) and Scaringe et al., Nucleic Acids Res., 18:5433-5441 (1990). Custom and large-scale siRNA synthesis services are available from commercial vendors such as Ambion (Austin, Tex., USA), Dharmacon Research (Lafayette, Colo., USA), Pierce Chemical (Rockford, Ill., USA), ChemGenes (Ashland, Mass., USA), Proligo (Hamburg, Germany), and Cruachem (Glasgow, UK).

As used herein, "modified equivalent" means a modified form of a particular siRNA compound having the same target-specificity (i.e., recognizing the same mRNA molecules that complement the unmodified particular siRNA compound). Thus, a modified equivalent of an unmodified siRNA compound can have modified ribonucleotides, that is, ribonucleotides that contain a modification in the chemical structure of an unmodified nucleotide base, sugar and/or phosphate (or phosphodiester linkage). As is known in the art, an "unmodified ribonucleotides" has one of the bases adenine, cytosine, guanine, and uracil joined to the 1' carbon of beta-D-ribo-furanose.

Preferably, modified siRNA compounds contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is herein incorporated by reference.

Modified forms of siRNA compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxymethyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyluridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N-6-isopentenyladenosine, beta-D-mannosylqueosine, uridine-5-oxyacetic acid, 2-thiocytidine, threonine derivatives, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, PCT Publication No. WO 92/07065; PCT Publication No. WO 93/15187; and Limbach et al., Nucleic Acids Res., 22:2183 (1994), each of which is incorporated herein by reference in its entirety.

In addition, modified siRNA compounds can also have substituted or modified sugar moieties, e.g., 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,053 5,639,873; 5,646,265; 5,658,873; 5,670,633; and 5,700,920, each of which is herein incorporated by reference.

Modified siRNA compounds may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., Nature, 344:565 (1990); Pieken et al., Science, 253:314 (1991); and Usman and Cedergren, Trends in Biochem. Sci., 17:334 (1992).

Preferably, the 3' overhangs of the siRNAs of the present invention are modified to provide resistance to cellular nucleases. In one embodiment the 3' overhangs comprise 2'-deoxyribonucleotides. In a preferred embodiment (depicted in FIG. 1) these 3' overhangs comprise a dinucleotide made of two 2'-deoxythymidine residues (i.e., dTdT) linked by a 5'-3' phosphodiester linkage.

siRNA compounds may be administered to mammals by various methods through different routes. For example, they can be administered by intravenous injection. See Song et al., Nature Medicine, 9:347-351 (2003). They can also be delivered directly to a particular organ or tissue by any suitable localized administration methods. Several other approaches for delivery of siRNA into animals have also proved to be successful. See e.g., McCaffery et al., Nature, 418:38-39 (2002); Lewis et al., Nature Genetics, 32:107-108 (2002); and Xia et al., Nature Biotech., 20:1006-1010 (2002). Alternatively, they may be delivered encapsulated in liposomes, by iontophoresis, or by incorporation into other vehicles such as hydrogels, cyclodextrins, biodegradable nanocapsules, and bioadhesive microspheres.

A particularly preferred method of in vivo delivery of siRNA, shRNAs or enzymatic nucleic acids is the process of lipofection. In lipofection, cationic lipids are used to promote encapsulation of negatively charged nucleic acids into liposomes, and the cationic lipids on the surface of the liposomes facilitate fusion of the liposomes with negatively charged bi-layer cell membranes (Yanagihara et al., *Mol. Cell. Biol. Hum. Dis. Ser.* 5:64-82 (1995); and Felgner and Ringold, *Science* 337:387-388 (1989)). Improvements in the lipids used to prepare liposomes have been made and synthetic cationic lipids specifically designed to limit the difficulties and complications encountered with liposome-mediated transfection in vivo can be used to prepare liposomes for in-vivo delivery (Templeton, *Biosci. Rep.* 22:283-295 (2002); Katsel and Greenstein, Biotechnol. *Annu. Rev.* 5:197-220 (2000)). Such compositions and methods have been described in the following publications, which are all incorporated by reference in their entirety: Felgner et al., *Proc. Natl. Acad. Sci.* USA 84:7413-7417 (1987); Mackey et al., *Proc. Natl. Acad. Sci.* USA 85:8027-8031 (1988); Ulmer et al., *Science* 259:1745-1748 (1992); Yamazaki et al., *Gene Ther.* 7:1148-1155 (2000); Oku et al., *Adv. Drug Deliv. Rev.* 52:209-218 (2001) and Matsuura et al., *Biochem. Biophys. Acta* 1612:136-143 (2003). Compounds and compositions that are particularly useful in the preparation of liposomes, and in the liposome-mediated transfection of cells are described in Matsuura et al., *Biochem. Biophys. Acta* 1612: 136-143 (2003), international patent publications WO 95/18863 and WO 96/17823, as well as U.S. Pat. Nos. 5,169,636, 5,459,127, 5,651,981, 5,661,018, 5,686,620, 5,688,958, 5,695,780, 5,780,053, 5,855,910, 5,891,714, 6,187,760 and 6,316,260, which are herein incorporated by reference in their entirety. Particularly preferred compositions and methods for use in delivering siRNAs to mammalian cells are provided by U.S. Patent Application Publication Nos. 2002/0165183, 2003/0073640, 2003/0125281, and 2003/0143204 which are also herein incorporated by reference in their entirety.

In addition, siRNAs may also be delivered by a gene therapy approach, using a DNA vector from which siRNA precursors, e.g., small hairpin form (shRNA), can be transcribed directly. Recent studies have demonstrated that while siRNAs, which are double-stranded, are very effective at mediating RNAi, short, single-stranded, hairpin-shaped RNAs (shRNAs) can also mediate RNAi, presumably because they fold into intramolecular duplexes that are processed into double-stranded siRNAs by cellular enzymes. See Sui et al., *Proc. Natl. Acad. Sci. U.S.A.*, 99:5515-5520 (2002); Yu et al., *Proc. Natl. Acad. Sci. U.S.A.*, 99:6047-6052 (2002); and Paul et al., *Nature Biotech.*, 20:505-508 (2002)). This discovery has significant and far-reaching implications, since the production of such shRNAs can be readily achieved in vivo by transfecting cells with DNA vectors bearing short inverted repeats separated by a small number of (e.g., 3 to 9) nucleotides that direct the transcription of such shRNAs. Additionally, if mechanisms are included to direct the integration of the transcription cassette into the host cell genome, or to ensure the stability of the transcription vector, the RNAi caused by the encoded shRNAs, can be made stable and/or heritable. Not only have such techniques been used to "knock down" the expression of specific genes in mammalian cells, but also they have now been successfully employed to knock down the expression of exogenously expressed transgenes, as well as endogenous genes in the brain and liver of living mice. See generally Hannon, *Nature.* 418:244-251 (2002) and Shi, *Trends Genet.*, 19:9-12 (2003); see also Xia et al., *Nature Biotech.*, 20:1006-1010 (2002).

Detailed methods for the intracellular expression and delivery of siRNAs and shRNAs in mammalian cells are provided in U.S. Patent Application Publication 2003/0148519 by Engelke et al., and in publications by Paul et al. (*Nat. Biotechnol.* 20:505-508 (2002) and *Mol. Ther.* 7:237-247 (2003)), all of which are incorporated by reference herein in their entirety.

Examples of siRNA duplexes and shRNAs specific against Tsg101 mRNA are provided in FIG. 5 and FIG. 6, respectively.

Thus, the present invention provides methods of inhibiting viral budding comprising administering to cells infected with viruses, particularly viruses utilizing Tsg101 in viral budding (e.g., HIV and lentiviruses), an siRNA or shRNA capable inducing the degradation of Tsg101 transcripts, preferably by at least 20%, 50%, or 60%.

The shRNAs can be delivered by any gene therapy method discussed below using an expression vector. Thus, the present invention also encompasses expression vectors having a promoter operably linked to a nucleic acid encoding an shRNA capable of inducing the degradation of Tsg101 transcripts when transcribed inside cells. Additionally, the present invention also encompasses isolated host cells having an expression vector which comprises a promoter operably linked to a nucleic acid encoding an shRNA capable of inducing the degradation of Tsg101 transcripts when transcribed inside cells.

Further, the present invention also provides a pharmaceutical composition having an siRNA or an expression vector as described above, in admixture with a pharmaceutically acceptable carrier as described below. In one embodiment, the composition comprises an siRNA or expression vector in admixture with liposome or other suitable carrier capable of facilitating the delivery of the siRNA or expression vector into cells.

In addition, an expression vector is also provided comprising a promoter operably linked to a nucleic acid encoding an shRNA capable of hybridizing to a region of an HIV transcript encoding the GAG polypeptide. Preferably, said region encodes HIV GAGp6.

5.3. Competitive Inhibition

The patient concentration and activity of a particular protein complex and the interacting protein members thereof identified in accordance with the present invention may also be inhibited by various other methods. For example, compounds identified in accordance with the methods described in Section 4 that are capable of interfering with or dissociating protein-protein interactions between the interacting protein members of a protein complex may be administered to cells or tissue in vitro or in a patient. Compounds identified in in vitro binding assays described in Section 4 that bind to the Tsg101-containing protein complex or the interacting members thereof may also be used in the treatment.

In addition, useful agents also include incomplete proteins, i.e., fragments of the interacting protein members that are capable of binding to their respective binding partners in a protein complex but are defective with respect to their cellular functions. For example, binding domains of the interacting member proteins of a protein complex may be used as competitive inhibitors of the activities of the protein complex. As will be apparent to skilled artisans, derivatives or homologues of the binding domains may also be used. Binding domains can be easily identified using molecular biology techniques, e.g., mutagenesis in combination with yeast two-hybrid assays. Preferably, the protein fragment used is a fragment of an interacting protein member having a length of less than 90%, 80%, more preferably less than 75%, 65%, 50%, or less than 40% of the full length of the protein member. In one embodiment, a HIV GAG protein fragment capable of binding Tsg101 is administered. For example, suitable protein fragments can include a polypeptide having a contiguous span of 4, 5, 6, 7, 8, 9, 10, 11, 12, 13, 14, 15, 18, 20 or 25, preferably from 4 to 30, 40 or 50 amino acids or more of the sequence of HIV GAG and is capable of interacting with Tsg101 through the UEV domain. For example, it has been discovered that a contiguous span of 8 amino acids in the late domain region of HIV GAGp6 (PEPTAPPEE, SEQ ID NO:22) is effective in inhibiting HIV viral budding. In one embodiment, a peptide having a contiguous span of from about 6, 7, 8, 9 or 10 to about 14, 15, 16, 18, 20 or 25 amino acid residues of HIV GAG which encompasses the late domain motif of HIV GAG, is administered to a host cell to inhibit viral budding. Also, suitable protein fragments can also include a peptide capable of binding Tsg101 and having an amino acid sequence of from 4 to 30 amino acids that is at least 75%, 80%, 82%, 85%, 87%, 90%, 95% or more identical to a contiguous span of amino acids of HIV GAG or GAGp6 of the same length. Alternatively, a polypeptide capable of interacting with HIV GAGp6 and having a contiguous span of 4, 5, 6, 7, 8, 9, 10, 11, 12, 13, 14, 15, 18, 20 or 25, preferably from 4 to 30, 40 or 50 or more amino acids of the amino acid sequence of Tsg101 may be administered. Also, other examples of suitable compounds include a peptide capable of binding HIV GAGp6 and having an amino acid sequence of from 4 to 30, 40, 50 or more amino acids that is at least 75%, 80%, 82%, 85%, 87%, 90%, 95% or more identical to a contiguous span of amino acids of Tsg101 amino acid sequence of the same length. In addition, the administered compounds can also be an antibody or antibody fragment, preferably single-chain antibody immunoreactive with Tsg101 or HIV GAGp6 or protein complexes of the present invention.

The protein fragments suitable as competitive inhibitors can be delivered into cells by direct cell internalization, receptor mediated endocytosis, or via a "transporter." It is noted that when the target proteins or protein complexes to be modulated reside inside cells, the compound administered to cells in vitro or in vivo in the method of the present invention preferably is delivered into the cells in order to achieve optimal results. Thus, preferably, the compound to be delivered is associated with a transporter capable of increasing the uptake of the compound by cells having the target protein or protein complex. As used herein, the term "transporter" refers to an entity (e.g., a compound or a composition or a physical structure formed from multiple copies of a compound or multiple different compounds) that is capable of facilitating the uptake of a compound of the present invention by animal cells, particularly human cells. Typically, the cell uptake of a compound of the present invention in the presence of a "transporter" is at least 20% higher, preferably at least 40%, 50%, 75%, and more preferably at least 100% higher than the cell uptake of the compound in the absence of the "transporter."

Many molecules and structures known in the art can be used as "transporters." In one embodiment, a penetratin is used as a transporter. For example, the homeodomain of Antennapedia, a *Drosophila* transcription factor, can be used as a transporter to deliver a compound of the present invention. Indeed, any suitable member of the penetratin class of peptides can be used to carry a compound of the present invention into cells. Penetratins are disclosed in, e.g., Derossi et al., *Trends Cell Biol.*, 8:84-87 (1998), which is incorporated herein by reference. Penetratins transport molecules attached thereto across cytoplasm membranes or nucleus membranes efficiently in a receptor-independent, energy-independent, and cell type-independent manner. Methods for using a penetratin as a carrier to deliver oligonucleotides and polypeptides are also disclosed in U.S. Pat. No. 6,080,724; Pooga et al., *Nat. Biotech.*, 16:857 (1998); and Schutze et al., *J. Immunol.*, 157:650 (1996), all of which are incorporated herein by reference. U.S. Pat. No. 6,080,724 defines the minimal requirements for a penetratin peptide as a peptide of 16 amino acids with 6 to 10 of which being hydrophobic. The amino acid at position 6 counting from either the N- or C-terminal is tryptophan, while the amino acids at positions 3 and 5 counting from either the N- or C-terminal are not both valine. Preferably, the helix 3 of the homeodomain of *Drosophila* Antennapedia is used as a transporter. More preferably, a peptide having a sequence of the amino acids 43-58 of the homeodomain Antp is employed as a transporter. In addition, other naturally occurring homologs of the helix 3 of the homeodomain of *Drosophila* Antennapedia can also be used. For example, homeodomains of Fushi-tarazu and Engrailed have been shown to be capable of transporting peptides into cells. See Han et al., *Mol. Cells*, 10:728-32 (2000). As used herein, the term "penetratin" also encompasses peptoid analogs of the penetratin peptides. Typically, the penetratin peptides and peptoid analogs thereof are covalently linked to a compound to be delivered into cells thus increasing the cellular uptake of the compound.

In another embodiment, the HIV-1 tat protein or a derivative thereof is used as a "transporter" covalently linked to a compound according to the present invention. The use of HIV-1 tat protein and derivatives thereof to deliver macromolecules into cells has been known in the art. See Green and Loewenstein, *Cell*, 55:1179 (1988); Frankel and Pabo, *Cell*, 55:1189 (1988); Vives et al., *J. Biol. Chem.*, 272: 16010-16017 (1997); Schwarze et al., *Science*, 285:1569-1572 (1999). It is known that the sequence responsible for cellular uptake consists of the highly basic region, amino acid residues 49-57. See e.g., Vives et al., *J. Biol. Chem.*, 272:16010-16017 (1997); Wender et al., *Proc. Nat'l Acad. Sci. USA*, 97:13003-13008 (2000). The basic domain is believed to target the lipid bilayer component of cell membranes. It causes a covalently linked protein or nucleic acid to cross cell membrane rapidly in a cell type-independent manner. Proteins ranging in size from 15 to 120 kD have been delivered with this technology into a variety of cell types both in vitro and in vivo. See Schwarze et al., *Science*, 285:1569-1572 (1999). Any HIV tat-derived peptides or peptoid analogs thereof capable of transporting macromolecules such as peptides can be used for purposes of the present invention. For example, any native tat peptides having the highly basic region, amino acid residues 49-57 can be used as a transporter by covalently linking it to the compound to be delivered. In addition, various analogs of the tat peptide of amino acid residues 49-57 can also be useful transporters for purposes of this invention. Examples of various such analogs are disclosed in Wender et al., *Proc. Nat'l Acad. Sci. USA*, 97:13003-13008 (2000) (which is incorporated herein by reference) including, e.g., d-Tat$_{49-57}$, retro-inverso isomers of l- or d-Tat$_{49-57}$ (i.e., l-Tat$_{57-49}$ and d-Tat$_{57-49}$), L-arginine oligomers, D-arginine oligomers, L-lysine oligomers, D-lysine oligomers, L-histine oligomers, D-histine oligomers, L-ornithine oligomers, D-ornithine oligomers, and various homologues, derivatives (e.g., modified forms with conjugates linked to the small peptides) and peptoid analogs thereof.

Other useful transporters known in the art include, but are not limited to, short peptide sequences derived from fibroblast growth factor (See Lin et al., *J. Biol. Chem.*, 270: 14255-14258 (1998)), Galparan (See Pooga et al., *FASEB J.* 12:67-77 (1998)), and HSV-1 structural protein VP22 (See Elliott and O'Hare, *Cell*, 88:223-233 (1997)).

As the above-described various transporters are generally peptides, fusion proteins can be conveniently made by recombinant expression to contain a transporter peptide covalently linked by a peptide bond to a competitive protein fragment. Alternatively, conventional methods can be used to chemically synthesize a transporter peptide or a peptide of the present invention or both.

The hybrid peptide can be administered to cells in vitro or to a patient in a suitable pharmaceutical composition as provided in Section 5.

In addition to peptide-based transporters, various other types of transporters can also be used, including but not limited to cationic liposomes (see Rui et al., *J. Am. Chem. Soc.*, 120:11213-11218 (1998)), dendrimers (Kono et al., *Bioconjugate Chem.*, 10:1115-1121 (1999)), siderophores (Ghosh et al., *Chem. Biol.*, 3:1011-1019 (1996)), etc. In a specific embodiment, the compound according to the present invention is encapsulated into liposomes for delivery into cells.

Additionally, when a compound according to the present invention is a peptide, it can be administered to cells by a gene therapy method. That is, a nucleic acid encoding the peptide can be administered to in vitro cells or to cells in vivo in a human or animal body. Any suitable gene therapy methods may be used for purposes of the present invention. Various gene therapy methods are well known in the art and are described in Section 6.3.2. below. Successes in gene therapy have been reported recently. See e.g., Kay et al., *Nature Genet.*, 24:257-61 (2000); Cavazzana-Calvo et al., *Science*, 288:669 (2000); and Blaese et al., *Science*, 270: 475 (1995); Kantoff, et al., *J. Exp. Med.*, 166:219 (1987).

5.4. Gene Therapy

In yet another embodiment, the gene therapy approach is taken to "knock out" the gene encoding Tsg101, or to reduce the gene expression level. For example, the gene may be replaced with a different gene sequence or a non-functional sequence or simply deleted by homologous recombination. In another gene therapy embodiment, the method disclosed in U.S. Pat. No. 5,641,670, which is incorporated herein by reference, may be used to reduce the expression of the Tsg101 gene. Essentially, an exogenous DNA having at least a regulatory sequence, an exon and a splice donor site can be introduced into an endogenous gene encoding Tsg101 by homologous recombination such that the regulatory sequence, the exon and the splice donor site present in the DNA construct become operatively linked to the endogenous gene. As a result, the expression of the endogenous gene is controlled by the newly introduced exogenous regulatory sequence. Therefore, when the exogenous regulatory sequence is a strong gene expression repressor, the expression of the endogenous gene encoding the interacting protein member is reduced or blocked. See U.S. Pat. No. 5,641,670.

Various gene therapy methods are well known in the art. Successes in gene therapy have been reported recently. See e.g., Kay et al., *Nature Genet.*, 24:257-61 (2000); Cavazzana-Calvo et al., *Science*, 288:669 (2000); and Blaese et al., *Science*, 270: 475 (1995); Kantoff, et al., *J. Exp. Med.* 166:219 (1987).

Any suitable gene therapy methods may be used for purposes of the present invention. Generally, a gene therapy vector is used to carry the nucleic acids (exogenous nucleic acids) useful in modifying the endogenous Tsg101 gene. The vector typically includes nucleic acid sequences that can direct site-specific homologous recombination. For example, an exogenous nucleic acid encoding a defective Tsg101 protein, e.g., incapable of binding HIV GAGp6, is preferably carried within the gene therapy vector. Alternatively, the vector may contain sequences corresponding to the two ends of the endogenous Tsg101 gene, which can cause homologous recombination thereby "knocking out" the endogenous Tsg101 gene.

In one embodiment, the exogenous nucleic acid (gene) is incorporated into a plasmid DNA vector. Many commercially available expression vectors may be useful for the present invention, including, e.g., pCEP4, pcDNAI, pIND, pSecTag2, pVAX1, pcDNA3.1, and pBI-EGFP, and pDisplay.

Various viral vectors may also be used. Typically, in a viral vector, the viral genome is engineered to eliminate the disease-causing capability, e.g., the ability to replicate in the host cells. The exogenous nucleic acid to be introduced into a patient may be incorporated into the engineered viral genome, e.g., by inserting it into a viral gene that is non-essential to the viral infectivity. Viral vectors are convenient to use as they can be easily introduced into tissue cells by way of infection. Once in the host cell, the recombinant virus typically is integrated into the genome of the host cell. In rare instances, the recombinant virus may also replicate and remain as extrachromosomal elements.

A large number of retroviral vectors have been developed for gene therapy. These include vectors derived from oncoretroviruses (e.g., MLV), lentiviruses (e.g., HIV and SIV) and other retroviruses. For example, gene therapy vectors have been developed based on murine leukemia virus (See, Cepko, et al., *Cell*, 37:1053-1062 (1984), Cone and Mulligan, *Proc. Natl. Acad. Sci. U.S.A.*, 81:6349-6353 (1984)), mouse mammary tumor virus (See, Salmons et al., *Biochem. Biophys. Res. Commun.*, 159:1191-1198 (1984)), gibbon ape leukemia virus (See, Miller et al., *J. Virology*, 65:2220-2224 (1991)), HIV, (See Shimada et al., *J. Clin. Invest.*, 88:1043-1047 (1991)), and avian retroviruses (See Cosset et al., *J. Virology*, 64:1070-1078 (1990)). In addition, various retroviral vectors are also described in U.S. Pat. Nos. 6,168,916; 6,140,111; 6,096,534; 5,985,655; 5,911,983; 4,980,286; and 4,868,116, all of which are incorporated herein by reference.

Adeno-associated virus (AAV) vectors have been successfully tested in clinical trials. See e.g., Kay et al., *Nature Genet.* 24:257-61 (2000). AAV is a naturally occurring defective virus that requires other viruses such as adenoviruses or herpes viruses as helper viruses. See Muzyczka, *Curr. Top. Microbiol. Immun.*, 158:97 (1992). A recombinant AAV virus useful as a gene therapy vector is disclosed in U.S. Pat. No. 6,153,436, which is incorporated herein by reference.

Adenoviral vectors can also be useful for purposes of gene therapy in accordance with the present invention. For example, U.S. Pat. No. 6,001,816 discloses an adenoviral vector, which is used to deliver a leptin gene intravenously to a mammal to treat obesity. Other recombinant adenoviral vectors may also be used, which include those disclosed in U.S. Pat. Nos. 6,171,855; 6,140,087; 6,063,622; 6,033,908; and 5,932,210, and Rosenfeld et al., *Science,* 252:431-434 (1991); and Rosenfeld et al., *Cell,* 68:143-155 (1992).

Other useful viral vectors include recombinant hepatitis viral vectors (See, e.g., U.S. Pat. No. 5,981,274), and recombinant entomopox vectors (See, e.g., U.S. Pat. Nos. 5,721,352 and 5,753,258). Non-traditional vectors may also be used for purposes of this invention. For example, International Publication No. WO 94/18834 discloses a method of delivering DNA into mammalian cells by conjugating the DNA to be delivered with a polyelectrolyte to form a complex. The complex may be microinjected into or uptaken by cells.

The exogenous nucleic acids may also be introduced into cells by way of receptor-mediated endocytosis. See e.g., U.S. Pat. No. 6,090,619; Wu and Wu, *J. Biol. Chem.,* 263:14621 (1988); Curiel et al., *Proc. Natl. Acad. Sci. USA,* 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues), which is itself coupled to an integrin receptor-binding moiety (e.g., a cyclic peptide having the sequence RGD).

Alternatively, the exogenous nucleic acids or vectors containing it can also be delivered into cells via amphiphiles. See e.g., U.S. Pat. No. 6,071,890. Typically, the exogenous nucleic acid or a vector containing the nucleic acid forms a complex with the cationic amphiphile. Mammalian cells contacted with the complex can readily take the complex up.

The exogenous nucleic acids can be introduced into a patient for purposes of gene therapy by various methods known in the art. For example, the exogenous gene sequences alone or in a conjugated or complex form described above, or incorporated into viral or DNA vectors, may be administered directly by injection into an appropriate tissue or organ of a patient. Alternatively, catheters or like devices may be used for delivery into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

In addition, the exogenous nucleic acids or vectors containing the nucleic acids can be introduced into isolated cells using any known techniques such as calcium phosphate precipitation, microinjection, lipofection, electroporation, gene gun, receptor-mediated endocytosis, and the like. Cells expressing the exogenous nucleic acids may be selected and redelivered back to the patient by, e.g., injection or cell transplantation. The appropriate amount of cells delivered to a patient will vary with patient conditions, and desired effect, which can be determined by a skilled artisan. See e.g., U.S. Pat. Nos. 6,054,288; 6,048,524; and 6,048,729. Preferably, the cells used are autologous, i.e., cells obtained from the patient being treated.

6. Pharmaceutical Compositions and Formulations

In another aspect of the present invention, pharmaceutical compositions are also provided containing one or more of the therapeutic agents provided in the present invention as described in Section 6. For example, such therapeutic agents include, but are not limited to, (1) small organic compounds selected based on the screening methods of the present invention capable of interfering with the interaction between Tsg101 and HIV GAG or GAGp6 or another retroviral GAG containing a P(T/S)AP (SEQ ID NO:1 or SEQ ID NO:3) late domain motif, (2) antisense compounds specifically hybridizable to Tsg101 nucleic acids (gene or mRNA), (3) ribozyme compounds specific to Tsg101 nucleic acids (gene or mRNA), (4) antibodies immunoreactive with Tsg101 or HIV GAG or GAGp6 or another retroviral GAG containing a P(T/S)AP (SEQ ID NO:1 or SEQ ID NO:3) late domain motif, (5) antibodies selectively immunoreactive with a protein complex of the present invention, (6) small organic compounds capable of binding a protein complex of the present invention, (7) small peptide compounds as described above (optionally linked to a transporter) capable of interacting with Tsg101 or a retroviral GAG polypeptide, (8) nucleic acids encoding the antibodies or peptides, etc. The compositions are prepared as a pharmaceutical formulation suitable for administration into a patient. Accordingly, the present invention also extends to pharmaceutical compositions, medicaments, drugs or other compositions containing one or more of the therapeutic agent in accordance with the present invention.

In the pharmaceutical composition, an active compound identified in accordance with the present invention can be in any pharmaceutically acceptable salt form. As used herein, the term "pharmaceutically acceptable salts" refers to the relatively non-toxic, organic or inorganic salts of the compounds of the present invention, including inorganic or organic acid addition salts of the compound. Examples of such salts include, but are not limited to, hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naphthylate salts, mesylate salts, tosylate salts, citrate salts, lactate salts, maleate salts, succinate salts, tartrate salts, fumarate salts, and the like. See, e.g., Berge, et al., *J. Pharm. Sci.,* 66:1-19 (1977).

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine,* 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45:242-247 (1984). Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels is biodegradable or biosorbable. For purposes of this invention, hydrogels made of polyethylene glycols, collagen, or poly(glycolic-co-L-lactic acid) may be useful. See, e.g., Phillips et al., *J. Pharmaceut. Sci.* 73:1718-1720 (1984).

The active compounds can also be conjugated, to a water-soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, *Am. J. Hosp. Pharm.,* 15:210-218 (1994). PEGylated proteins are currently being used in protein replacement therapies and for other therapeutic uses. For example, PEGylated interferon (PEG-IN-TRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology,* Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Generally, the toxicity profile and therapeutic efficacy of the therapeutic agents can be determined by standard pharmaceutical procedures in cell models or animal models, e.g., those provided in Section 7. As is known in the art, the $LD_{50}$ represents the dose lethal to about 50% of a tested population. The $ED_{50}$ is a parameter indicating the dose therapeutically effective in about 50% of a tested population. Both $LD_{50}$ and $ED_{50}$ can be determined in cell models and animal models. In addition, the $IC_{50}$ may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the $ED_{50}$ and/or $IC_{50}$, but significantly below the $LD_{50}$ obtained from cell or animal models.

It will be apparent to skilled artisans that therapeutically effective amount for each active compound to be included in a pharmaceutical composition of the present invention can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like. The amount of administration can also be adjusted as the various factors change over time.

EXAMPLES

1. Yeast Two-Hybrid System

The principles and methods of the yeast two-hybrid system have been described in detail in *The Yeast Two-Hybrid System,* Bartel and Fields, eds., pages 183-196, Oxford University Press, New York, N.Y., 1997. The following is thus a description of the particular procedure that we used.

The cDNA encoding the bait protein HIV GAGp6 was derived from HIV-1 NY5/BRU isolate. The cDNA product was then introduced by recombination into the yeast expression vector pGBT.Q, which is a close derivative of pGBT.C (See Bartel et al., *Nat Genet.*, 12:72-77 (1996)) in which the polylinker site has been modified to include M13 sequencing sites. The new construct was selected directly in the yeast strain PNY200 for its ability to drive tryptophane synthesis (genotype of this strain: MATα trp1-901 leu2-3,112 ura3-52 his3-200 ade2 gal4Δ gal80). In these yeast cells, the bait was produced as a C-terminal fusion protein with the DNA binding domain of the transcription factor Gal4 (amino acids 1 to 147).

Prey libraries (e.g., a human spleen cDNA library) were transformed into the yeast strain BK100 (genotype of this strain: MATa trp1-901 leu2-3,112 ura3-52 his3-200 gal4Δ gal80 LYS2::GAL-HIS3 GAL2-ADE2 met2::GAL7-lacZ), and selected for the ability to drive leucine synthesis. In these yeast cells, each cDNA was expressed as a fusion protein with the transcription activation domain of the transcription factor Gal4 (amino acids 768 to 881) and a 9 amino acid hemagglutinin epitope tag. PNY200 cells (MATα mating type), expressing the bait, were then mated with BK100 cells (MATa mating type), expressing prey proteins from the prey library. The resulting diploid yeast cells expressing proteins interacting with the bait protein were selected for the ability to synthesize tryptophan, leucine, histidine, and adenine. DNA was prepared from each clone, transformed by electroporation into *E. coli* strain KC8 (Clontech KC8 electrocompetent cells, Catalog No. C2023-1), and the cells were selected on ampicillin-containing plates in the absence of either tryptophan (selection for the bait plasmid) or leucine (selection for the library plasmid). DNA for both plasmids was prepared and sequenced by the dideoxynucleotide chain termination method. The identity of the bait cDNA insert was confirmed and the cDNA insert from the prey library plasmid was identified using the BLAST program to search against public nucleotide and protein databases. Plasmids from the prey library were then individually transformed into yeast cells together with a plasmid driving the synthesis of lamin and 5 other test proteins, respectively, fused to the Gal4 DNA binding domain. Clones that gave a positive signal in the β-galactosidase assay were considered false-positives and discarded. Plasmids for the remaining clones were transformed into yeast cells together with the original bait plasmid. Clones that gave a positive signal in the β-galactosidase assay were considered true positives.

HIV GAGp6 sequence indicated in Table 1 was used in the yeast two-hybrid system described above. The isolated Tsg101 prey sequences are summarized in Table 1. The GenBank Accession Nos. for the bait and prey proteins are also provided in Table 1, upon which the bait and prey sequences are aligned.

2. Production of Antibodies Selectively Immunoreactive with Protein Complex

HIV GAGp6 and the UEV domain of Tsg101 are recombinantly expressed in human host cells and isolated and purified. A protein complex is formed by mixing the two purified interacting proteins (fragments). A protein complex is also formed by mixing recombinantly expressed intact complete Tsg101 and HIV GAGp6. The two protein complexes are used as antigens in immunizing a mouse. mRNA is isolated from the immunized mouse spleen cells, and first-strand cDNA is synthesized based on the mRNA. The $V_H$ and $V_K$ genes are amplified from the thus synthesized cDNAs by PCR using appropriate primers.

The amplified $V_H$ and $V_K$ genes are ligated together and subcloned into a phagemid vector for the construction of a phage display library. *E. coli* cells are transformed with the ligation mixtures, and thus a phage display library is established. Alternatively, the ligated $V_H$ and $V_k$ genes are subcloned into a vector suitable for ribosome display in which the $V_H$-$V_k$ sequence is under the control of a T7 promoter. See Schaffitzel et al., *J. Immun. Meth.*, 231:119-135 (1999).

The libraries are screened with the Tsg101-HIV GAGp6 complex and individual Tsg101 and HIV GAGp6. Several rounds of screening are preferably performed. Clones corresponding to scFv fragments that bind the Tsg101-HIV GAGp6 complex, but not the individual Tsg101 and HIV GAGp6 are selected and purified. A single purified clone is used to prepare an antibody selectively immunoreactive with the Tsg101-HIV GAGp6 complex. The antibody is then verified by an immunochemistry method such as RIA and ELISA.

In addition, the clones corresponding to scFv fragments that bind the Tsg101—HIV GAGp6 complex and also binds Tsg101 and/or HIV GAGp6 may be selected. The scFv genes in the clones are diversified by mutagenesis methods such as oligonucleotide-directed mutagenesis, error-prone PCR (See Lin-Goerke et al., *Biotechniques*, 23:409 (1997)), dNTP analogues (See Zaccolo et al., *J. Mol. Biol.*, 255:589 (1996)), and other methods. The diversified clones are further screened in phage display or ribosome display libraries. In this manner, scFv fragments selectively immunoreactive with the Tsg101-HIV GAGp6 complex may be obtained.

3. Correlations Between Tsg101-HIV GAGp6 Interaction and HIV Budding

Yeast two-hybrid assays were utilized to determine the effect of amino acid substitution mutations in the PTAP (SEQ ID NO:1) motif of HIV GAGp6 on the interaction between Tsg101 and GAGp6. To prepare a yeast two-hybrid activation domain-Tsg101 construct, a DNA fragment encompassing the full-length coding sequence for Tsg101 according to GenBank Accession No. U82130 was obtained by PCR from a human fetal brain cDNA library and cloned into the EcoRI/PstI sites of the activation domain parent plasmid GADpN2 (LEU2, CEN4, ARS1, ADH1p-SV40NLS-GAL4 (768-881)-MCS (multiple cloning site)-PGK1t, AmpR, ColE1_ori).

To prepare the yeast two-hybrid DNA binding domain-HIV1 GAGp6 construct, a DNA fragment corresponding to the HIV1 GAGp6 peptide derived from the HIV1.NL43 strain GAG protein was obtained by PCR from the NL43 containing plasmid R9Δapa and was cloned into the EcoRI/SalI sites of the binding domain parent plasmid pGBT.Q.

The following amino acid substitution mutations were introduced by PCR into the HIV1 GAGp6 sequence in the yeast two-hybrid binding domain-HIV1 GAGp6 construct described above. The mutations were verified by DNA sequence analysis. Such mutations are summarized in Table 3 below.

TABLE 3

Tested Mutations in GAGp6 Protein

| Mutant Construct | GAGp6 Peptide Sequence Surrounding the PTAP (SEQ ID NO:1) Motif | | | | | | | | | | | | | | |
|---|---|---|---|---|---|---|---|---|---|---|---|---|---|---|---|
| P6/wt | S | R | P | E | P | T | A | P | P | E | E | S | F | R | F |
| P6/E6G |   |   |   | G |   |   |   |   |   |   |   |   |   |   |   |
| P6/P7L |   |   |   |   | L |   |   |   |   |   |   |   |   |   |   |
| P6/A9R |   |   |   |   |   |   | R |   |   |   |   |   |   |   |   |
| P6/P10L |   |   |   |   |   |   |   | L |   |   |   |   |   |   |   |

To test the effect of the mutations, yeast cells of the strain Y189 purchased from Clontech (ura3-52 his3*200 ade2-101 trp1-901 leu2-3,112 met gal4 gal80 URA3::GAL1p-lacZ) were co-transformed with the activation domain-Tsg101 construct and one of the binding domain-mutant GAGp6 constructs or the binding domain-wild type GAGp6 construct. Filter lift assays for β-Gal activity were conducted by lifting the transformed yeast colonies with filters, lysing the yeast cells by freezing and thawing, and contacting the lysed cells with X-Gal. Positive β-Gal activity indicates that the GAGp6 wild type or mutant protein interacts with Tsg101. All binding domain constructs were also tested for self-activation of β-Gal activity. The results are shown in Table 4.

TABLE 4

Interactions Between Tsg101 and GAGp6

|         | P6/wt | P6/E6G | P6/P7L | P6/A9R | P6/P10L |
|---------|-------|--------|--------|--------|---------|
| Tsg101  | +     | +      | −      | −      | −       |
| P6/wt   | −     |        |        |        |         |
| P6/E6G  |       | −      |        |        |         |
| P6/P7L  |       |        | −      |        |         |
| P6/A9R  |       |        |        | −      |         |
| P6/P10L |       |        |        |        | −       |

Thus, as is clear from Table 3, the mutations in the PTAP (SEQ ID NO:1) motif of HIV GAGp6 abolished the interaction between Tsg101 and HIV GAGp6, while the p6/E6G mutation outside the PTAP (SEQ ID NO:1) motif did not result in the elimination of the Tsg101-GAGp6 interaction.

The interactions between Tsg101 and wild-type GAGp6 (WT) or the GAGp6 PTAP (SEQ ID NO:1) mutants were further quantitated by performing liquid culture β-galactosidase assays. Cultures were grown overnight in synthetic media (−Leu, −Trp, +glucose) in 96 well plates, normalized for optical density, and lysed by addition of 6×lysis/substrate solution in 6×Z-buffer (60 mM KCl, 6 mM MgSO$_4$, 360 mM Na$_2$HPO$_4$, 240 mM NaH$_2$PO$_4$, 6 mg/ml CPRG, 0.12 U/ml lyticase, 0.075% NP-40). Cultures were incubated for 2 hr at 37° C., clarified by centrifugation, and the optical absorbance of each supernatant was measured (575 nm). Full length Tsg101 bound wild-type p6 in the two-hybrid liquid culture assay, resulting in high levels of β-galactosidase activity (>300-fold over background). Three different p6 point mutants were used to test whether the Tsg101 binding interaction required the PTAP (SEQ ID NO:1) late domain motif within HIV-1 p6, and all three (P6L, A9R and P10L) reduced β-galactosidase activity to background levels. Each of these point mutations also arrests HIV-1 budding at a late stage (Huang et al. 1995). These results are consistent with the hypothesis that the interaction between HIV GAGp6 and the human cellular protein Tsg101 is essential for viral budding to occur.

4. In Vitro Binding Assays

A fusion protein with a GST tag fused to the HIV-1 GAGp6 domain was recombinantly expressed and purified by chromatography. In addition, a GAGp6 peptide containing the first 14 amino acid residues ("p6(1-14)") was synthesized chemically by standard peptide synthesis methods. The peptide was purified by conventional protein purification techniques, e.g., by chromatography.

Nunc/Nalgene Maxisorp plates were incubated overnight at 4° C. or for 1-2 hrs at room temperature in 100 μl of a protein coupling solution containing purified GST-p6 and 50 mM Carbonate, pH=9.6. This allowed the attachment of the GST-p6 fusion protein to the plates. Liquids in the plates were then emptied and wells filled with 400 μl/well of a blocking buffer (SuperBlock; Pierce-Endogen, Rockford, Ill.). After incubating for 1 hour at room temperature, 100 μl of a mixture containing Drosophila S2 cell lysate myc-tagged Tsg101 (residues 1-207) and a specific amount of the p6(1-14) peptide were applied to the wells of the plate. This mixture was allowed to react for 2 hours at room temperature to form p6:Tsg101 protein-protein complexes.

Plates were then washed 4×100 μl with 1×PBST solution (Invitrogen; Carlsbad, Calif.). After washing, 100 μl of 1 μg/ml solution of anti-myc monoclonal antibody (Clone 9E10; Roche Molecular Biochemicals; Indianapolis, Ind.) in 1×PBST was added to the wells of the plate to detect the myc-epitope tag on the Tsg101 protein. Plates were then washed again with 4×100 μl with 1×PBST solution and 100 μl of 1 μg/ml solution of horseradish peroxidase (HRP) conjugated Goat anti-mouse IgG (Jackson Immunoresearch Labs; West Grove, Pa.) in 1×PBST was added to the wells of the plate to detect bound mouse anti-myc antibodies. Plates were then washed again with 4×100 μl with 1×PBST solution and 100 μl of fluorescent substrate (QuantaBlu; Pierce-Endogen, Rockford, Ill.) was added to all wells. After 30 minutes, 100 μl of stop solution was added to each well to inhibit the function of HRP. Plates were then read on a Packard Fusion instrument at an excitation wavelength of 325 nm and an emission wavelength of 420 nm. The presence of fluorescent signals indicates binding of Tsg101 to the fixed GST-p6. In contrast, the absence of fluorescent signals indicates that the PX$_1$X$_2$P-containing short peptide is capable of disrupting the interaction between Tsg101 and HIV p6.

Figure 2:
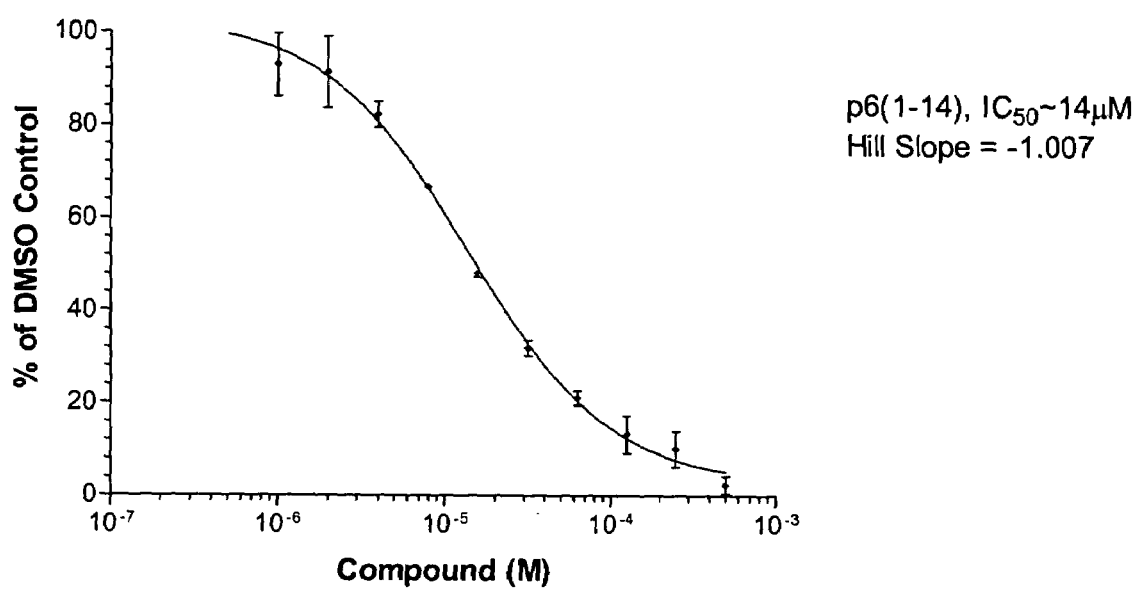
FIG. 2 is a competitive inhibition curve showing that the p6(1-14) peptide having the first 14 amino acid residues of HIV GAGp6 is capable of inhibiting protein-protein interaction between GST-p6 and myc-Tsg101(1-207)
Figure 3:
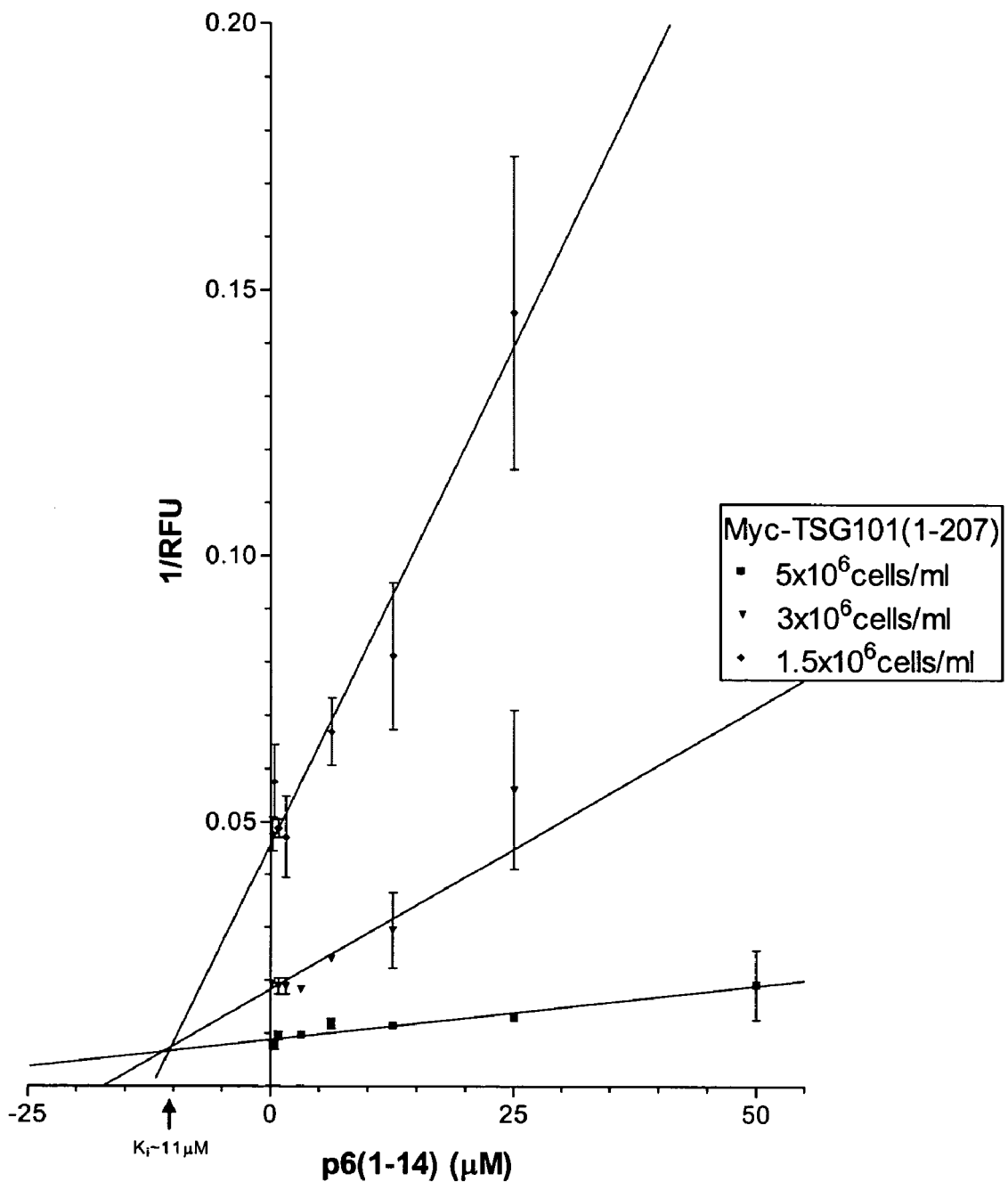
FIG. 3 is a Dixon plot showing p6(1-14) inhibition of the interaction between GST-p6 and myc-Tsg101(1-207)
Figure 4:
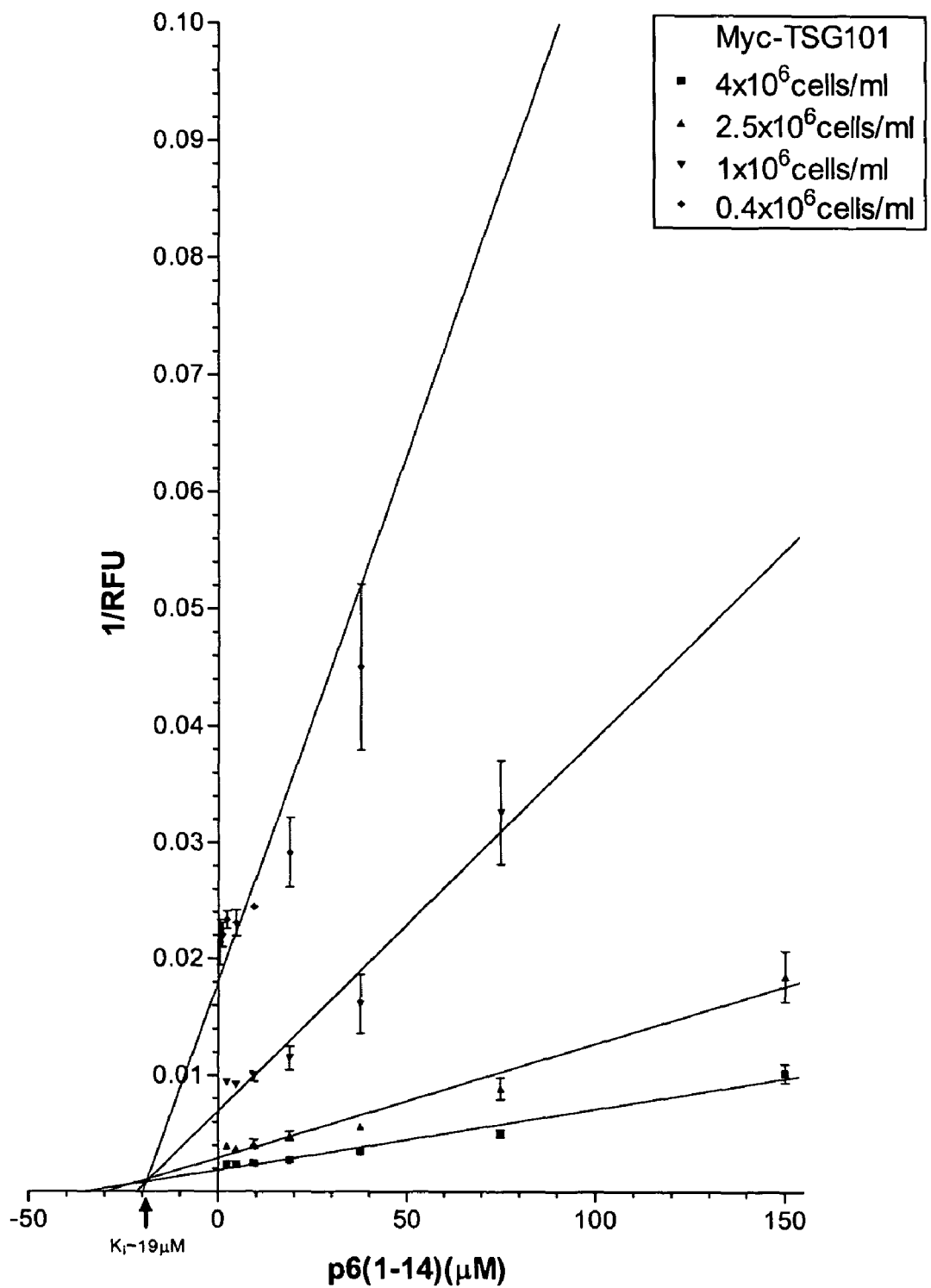
FIG. 4 is another Dixon plot showing p6(1-14) inhibition of the interaction between GST-p6 and myc-Tsg101(1-207)

Different concentrations of the p6(1-14) peptide were tested, and the relative intensities of the fluorescence signals obtained at different concentrations were plotted against the peptide concentrations. The competitive inhibition curve is shown in FIG. 2. Two Dixon plots are shown in FIG. 3 and FIG. 4, respectively.

5. Yeast Screen to Identify Small Molecule Inhibitors of the Interaction Between HIV GAGp6 and Tsg101

Beta-galactosidase is used as a reporter enzyme to signal the interaction between yeast two-hybrid protein pairs expressed from plasmids in *Saccharomyces cerevisiae*. Yeast strain MY209 (ade2 his3 leu2 trp1 cyh2 ura3::GAL1p-lacZ gal4 gal80 lys2::GAL1p-HIS3) bearing the plasmids Mp364 (LEU2 CEN4 ARS1 ADH1p-SV40NLS-GAL4 (768-881)-Tsg101 (1-390)-PGK1t AmpR ColE1_ori) and Mp206 (TRP1 CEN4 ARS ADH1p-GAL4(1-147)-HIV1_gag (448-500)-ADH1t AmpR ColE1_ori) is cultured in synthetic complete media lacking leucine and tryptophan (SC-Leu-Trp) overnight at 30° C. This culture is diluted to 0.01 $OD_{630}$ units/ml using SC-Leu-Trp media. The diluted MY209 culture is dispensed into 96-well microplates. Compounds from a library of small molecules are added to the microplates; the final concentration of test compounds is approximately 60 µM. The assay plates are incubated at 30° C. overnight.

The following day an aliquot of concentrated substrate/lysis buffer is added to each well and the plates incubated at 37° C. for 1-2 hours. At an appropriate time an aliquot of stop solution is added to each well to halt the beta-galactosidase reaction. For all microplates an absorbance reading is obtained to assay the generation of product from the enzyme substrate. The presence of putative inhibitors of the interaction between HIV p6 and Tsg101 results in inhibition of the beta-galactosidase signal generated by MY209. Additional testing eliminates compounds that decreased expression of beta-galactosidase by affecting yeast cell growth and non-specific inhibitors that affected the beta-galactosidase signal generated by the interaction of an unrelated protein pair.

Once a hit, i.e., a compound which inhibits the interaction between the viral and cellular proteins, is obtained, the compound is identified and subjected to further testing wherein the compounds are assayed at several concentrations to determine an $IC_{50}$ value, this being the concentration of the compound at which the signal seen in the two-hybrid assay described in this Example is 50% of the signal seen in the absence of the inhibitor.

6. Antisense Inhibition of Tsg101 Expression

Human 293 cells are cultured to reach about 80% confluency, and treated with antisense compounds. Cells in 96-well plates are first washed with 200 microliters of OPTI-MEM™-1 reduced-serum medium (Gibco BRL). After washing, the cells are treated with 130 µl of OPTI-MEM™-1 containing 3.75 µg/ml of LIPOFECTIN® (Gibco BRL) and a particular antisense compound at a final concentration of 150 nM. About 4 hours later, the medium is replaced with fresh medium. At 16 hours after antisense treatment, cells are harvested and assayed for Tsg101 expression.

Tsg101 expression can be examined by analyzing Tsg101 mRNA or protein in treated and untreated cells. Quantitative mRNA analysis can be performed by any of the methods known in the art, e.g., Northern blot, and preferably real-time quantitative RT-PCR.

Tsg101 protein levels in antisense-treated or -untreated cells can be measured by, e.g., immunoprecipitation, Western blot analysis (immunoblotting), ELISA or fluorescence-activated cell sorting (FACS), as are known in the art.

7. siRNA Inhibition of Tsg101

The day before transfections, $1 \times 10^5$ 293T cells are seeded into each well of a 12-well plate with 1 ml of fresh DMEM supplemented with 10% FBS and 1×NEAA, but without antibiotics. The day of the transfections, 100 pmol of a particular Tsg101 siRNA duplex (2 µl of 50 µM stock solution of each duplex) are diluted with 100 µl of Opti-MIM-1 medium (Gibco BRL). Additionally, 3 µl of LipofectAmine 2000 reagent (LF2000; Invitrogen, Inc., Carlsbad, Calif., USA) is diluted with 100 µl of Opti-MEM-I medium and incubated at RT for 5 minutes. The diluted LF2000 and different diluted siRNA duplexes, are then gently mixed and incubated at RT for 20 minutes. Transfections are initiated by transferring 200 µl of each mixed LF2000/siRNA into a separate well of the plate containing the seeded cells and rocking the plate to mix gently. The plate is then incubated for 48 hours at 37 C before cells are harvested.

Tsg101 expression can be examined by analyzing Tsg101 mRNA or protein in treated and untreated cells. Quantitative mRNA analysis can be performed by any of the methods known in the art, e.g., Northern blot, and preferably real-time quantitative RT-PCR.

For Western blot analysis, 20 µl of cell lysate mixed with SDS loading buffer is loaded per well in 1.5 mm thick/10 well 4-12% Tris-Glycine acrylamide gel. Prestained Molecular Weight Standards are also loaded into a single well according to manufacturer's instructions. The gel is electrophoresed at 135 V for about 2 hours. Proteins are electro-transferred from the gel to a nitrocellulose membrane as follows: the gel, nitrocellulose membrane, filter paper, and sponge pad are pre-wet with 1× transfer buffer; the transfer sandwich is prepared and placed into the transfer module, which is filled with 1× Transfer Buffer, while the outside compartment with filled with water; the transfer apparatus is then subjected to 25 V for 2 hr. Following transfer the nitrocellulose membrane (western blot) is blocked with 5% milk in 1×TBST for 60 minutes at room temperature (or overnight at 4° C.). The blocked membrane is then incubated in primary antibody (anti-Tsg101) diluted in 1×TBST for 1 hour at room temperature. The membrane is washed three times for 5 minutes each with 1×TBST and incubated for 30 minutes at room temperature with horseradish peroxidase (HRP) conjugated secondary antibody. The membrane is then washed three times for 5 minutes each with 1×TBST, and once for 5 minutes with 1×TBS. The membrane is then incubated in ECL reagent for 1 minute at RT, and the signal is detected by either exposing the blot to film or by using the BioChemi system of UVP BioImaging Systems.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of inhibiting the binding of the human tumor susceptibility gene 101 protein (Tsg101) to the human immunodeficiency virus (HIV) GAG polyprotein (HIV GAG) comprising contacting Tsg101 with an antibody immunoreactive with the ubiquitin E2 variant (UEV) domain of Tsg101, in the presence of said HIV GAG, wherein said antibody inhibits said binding.

2. The method of claim 1, wherein said binding of Tsg101 to HIV GAG occurs between the UEV domain of Tsg101 and the late assembly domain of HIV GAG p6.

3. The method of claim 1, wherein said antibody is selectively immunoreactive with the UEV domain of Tsg101.

4. The method of claim 1, wherein said antibody is a polyclonal antibody.

5. The method of claim 1, wherein said antibody is a monoclonal antibody.

6. The method of claim 1, wherein said antibody is an antibody fragment.

7. The method of claim 1, wherein said antibody is a single chain antibody.

8. The method of claim 1, wherein said antibody is a humanized antibody.

* * * * *

SEQUENCE LISTING

<160> NUMBER OF SEQ ID NOS: 42

<210> SEQ ID NO 1
<211> LENGTH: 4
<212> TYPE: PRT
<213> ORGANISM: Human immunodeficiency virus

<400> SEQUENCE: 1

Pro Thr Ala Pro
1

<210> SEQ ID NO 2
<211> LENGTH: 4
<212> TYPE: PRT
<213> ORGANISM: Mutant human immunodeficiency virus

<400> SEQUENCE: 2

Pro Thr Thr Pro
1

<210> SEQ ID NO 3
<211> LENGTH: 4
<212> TYPE: PRT
<213> ORGANISM: Human immunodeficiency virus

<400> SEQUENCE: 3

Pro Ser Ala Pro
1

<210> SEQ ID NO 4
<211> LENGTH: 4
<212> TYPE: PRT
<213> ORGANISM: Mutant human immunodeficiency virus

<400> SEQUENCE: 4

Pro Ser Thr Pro
1

<210> SEQ ID NO 5
<211> LENGTH: 4
<212> TYPE: PRT
<213> ORGANISM: Mutant human immunodeficiency virus

<400> SEQUENCE: 5

Pro Ile Ala Pro
1

<210> SEQ ID NO 6
<211> LENGTH: 4
<212> TYPE: PRT
<213> ORGANISM: Mutant human immunodeficiency virus

<400> SEQUENCE: 6

Pro Ile Thr Pro
1

<210> SEQ ID NO 7
<211> LENGTH: 5
<212> TYPE: PRT
<213> ORGANISM: Human immunodeficiency virus

<400> SEQUENCE: 7

Glu Pro Thr Ala Pro

```
<210> SEQ ID NO 8
<211> LENGTH: 5
<212> TYPE: PRT
<213> ORGANISM: Human immunodeficiency virus

<400> SEQUENCE: 8

Glu Pro Ser Ala Pro
1               5

<210> SEQ ID NO 9
<211> LENGTH: 5
<212> TYPE: PRT
<213> ORGANISM: Human immunodeficiency virus

<400> SEQUENCE: 9

Pro Thr Ala Pro Pro
1               5

<210> SEQ ID NO 10
<211> LENGTH: 5
<212> TYPE: PRT
<213> ORGANISM: Human immunodeficiency virus

<400> SEQUENCE: 10

Pro Ser Ala Pro Pro
1               5

<210> SEQ ID NO 11
<211> LENGTH: 6
<212> TYPE: PRT
<213> ORGANISM: Human immunodeficiency virus

<400> SEQUENCE: 11

Glu Pro Thr Ala Pro Pro
1               5

<210> SEQ ID NO 12
<211> LENGTH: 6
<212> TYPE: PRT
<213> ORGANISM: Human immunodeficiency virus

<400> SEQUENCE: 12

Glu Pro Ser Ala Pro Pro
1               5

<210> SEQ ID NO 13
<211> LENGTH: 6
<212> TYPE: PRT
<213> ORGANISM: Human immunodeficiency virus

<400> SEQUENCE: 13

Pro Glu Pro Thr Ala Pro
1               5

<210> SEQ ID NO 14
<211> LENGTH: 6
<212> TYPE: PRT
<213> ORGANISM: Human immunodeficiency virus

<400> SEQUENCE: 14

Pro Glu Pro Ser Ala Pro
1               5
```

```
<210> SEQ ID NO 15
<211> LENGTH: 7
<212> TYPE: PRT
<213> ORGANISM: Human immunodeficiency virus

<400> SEQUENCE: 15

Arg Pro Glu Pro Thr Ala Pro
1               5

<210> SEQ ID NO 16
<211> LENGTH: 7
<212> TYPE: PRT
<213> ORGANISM: Human immunodeficiency virus

<400> SEQUENCE: 16

Arg Pro Glu Pro Ser Ala Pro
1               5

<210> SEQ ID NO 17
<211> LENGTH: 7
<212> TYPE: PRT
<213> ORGANISM: Human immunodeficiency virus

<400> SEQUENCE: 17

Pro Glu Pro Thr Ala Pro Pro
1               5

<210> SEQ ID NO 18
<211> LENGTH: 7
<212> TYPE: PRT
<213> ORGANISM: Human immunodeficiency virus

<400> SEQUENCE: 18

Pro Glu Pro Ser Ala Pro Pro
1               5

<210> SEQ ID NO 19
<211> LENGTH: 8
<212> TYPE: PRT
<213> ORGANISM: Human immunodeficiency virus

<400> SEQUENCE: 19

Glu Pro Thr Ala Pro Pro Glu Glu
1               5

<210> SEQ ID NO 20
<211> LENGTH: 8
<212> TYPE: PRT
<213> ORGANISM: Human immunodeficiency virus

<400> SEQUENCE: 20

Glu Pro Ser Ala Pro Pro Glu Glu
1               5

<210> SEQ ID NO 21
<211> LENGTH: 8
<212> TYPE: PRT
<213> ORGANISM: Human immunodeficiency virus

<400> SEQUENCE: 21

Glu Pro Thr Ala Pro Pro Ala Glu
1               5

<210> SEQ ID NO 22
```

```
<211> LENGTH: 9
<212> TYPE: PRT
<213> ORGANISM: Human immunodeficiency virus

<400> SEQUENCE: 22

Pro Glu Pro Thr Ala Pro Pro Glu Glu
1               5

<210> SEQ ID NO 23
<211> LENGTH: 9
<212> TYPE: PRT
<213> ORGANISM: Human immunodeficiency virus

<400> SEQUENCE: 23

Pro Glu Pro Thr Ala Pro Pro Ala Glu
1               5

<210> SEQ ID NO 24
<211> LENGTH: 9
<212> TYPE: PRT
<213> ORGANISM: Human immunodeficiency virus

<400> SEQUENCE: 24

Pro Glu Pro Ser Ala Pro Pro Glu Glu
1               5

<210> SEQ ID NO 25
<211> LENGTH: 10
<212> TYPE: PRT
<213> ORGANISM: Human immunodeficiency virus

<400> SEQUENCE: 25

Arg Pro Glu Pro Thr Ala Pro Pro Glu Glu
1               5                   10

<210> SEQ ID NO 26
<211> LENGTH: 10
<212> TYPE: PRT
<213> ORGANISM: Human immunodeficiency virus

<400> SEQUENCE: 26

Arg Pro Glu Pro Ser Ala Pro Pro Glu Glu
1               5                   10

<210> SEQ ID NO 27
<211> LENGTH: 10
<212> TYPE: PRT
<213> ORGANISM: Human immunodeficiency virus

<400> SEQUENCE: 27

Arg Pro Glu Pro Thr Ala Pro Pro Ala Glu
1               5                   10

<210> SEQ ID NO 28
<211> LENGTH: 10
<212> TYPE: PRT
<213> ORGANISM: Human immunodeficiency virus

<400> SEQUENCE: 28

Arg Pro Glu Pro Ser Ala Pro Pro Ala Glu
1               5                   10

<210> SEQ ID NO 29
<211> LENGTH: 13
<212> TYPE: PRT
```

```
<213> ORGANISM: Human immunodeficiency virus

<400> SEQUENCE: 29

Leu Gln Ser Arg Pro Glu Pro Thr Ala Pro Pro Glu Glu
1               5                   10

<210> SEQ ID NO 30
<211> LENGTH: 13
<212> TYPE: PRT
<213> ORGANISM: Human immunodeficiency virus

<400> SEQUENCE: 30

Leu Gln Ser Arg Pro Glu Pro Ser Ala Pro Pro Glu Glu
1               5                   10

<210> SEQ ID NO 31
<211> LENGTH: 14
<212> TYPE: PRT
<213> ORGANISM: Human immunodeficiency virus

<400> SEQUENCE: 31

Leu Gln Ser Arg Pro Glu Pro Thr Ala Pro Pro Glu Glu Ser
1               5                   10

<210> SEQ ID NO 32
<211> LENGTH: 14
<212> TYPE: PRT
<213> ORGANISM: Human immunodeficiency virus

<400> SEQUENCE: 32

Leu Gln Ser Arg Pro Glu Pro Ser Ala Pro Pro Glu Glu Ser
1               5                   10

<210> SEQ ID NO 33
<211> LENGTH: 30
<212> TYPE: DNA
<213> ORGANISM: Human immunodeficiency virus

<400> SEQUENCE: 33
ccaggcggcc gtcatggcgg tgtcggagag                                    30

<210> SEQ ID NO 34
<211> LENGTH: 18
<212> TYPE: DNA
<213> ORGANISM: Human immunodeficiency virus

<400> SEQUENCE: 34
accgccatga cggccgcc                                                 18

<210> SEQ ID NO 35
<211> LENGTH: 18
<212> TYPE: DNA
<213> ORGANISM: Human immunodeficiency virus

<400> SEQUENCE: 35
caccgccatg acggccgc                                                 18

<210> SEQ ID NO 36
<211> LENGTH: 18
<212> TYPE: DNA
<213> ORGANISM: Human immunodeficiency virus

<400> SEQUENCE: 36
acaccgccat gacggccg                                                 18
```

-continued

<210> SEQ ID NO 37
<211> LENGTH: 20
<212> TYPE: DNA
<213> ORGANISM: Human immunodeficiency virus

<400> SEQUENCE: 37
caccgccatg acggccgcct 20

<210> SEQ ID NO 38
<211> LENGTH: 20
<212> TYPE: DNA
<213> ORGANISM: Human immunodeficiency virus

<400> SEQUENCE: 38
acaccgccat gacggccgcc 20

<210> SEQ ID NO 39
<211> LENGTH: 20
<212> TYPE: DNA
<213> ORGANISM: Human immunodeficiency virus

<400> SEQUENCE: 39
gacaccgcca tgacggccgc 20

<210> SEQ ID NO 40
<211> LENGTH: 22
<212> TYPE: DNA
<213> ORGANISM: Human immunodeficiency virus

<400> SEQUENCE: 40
acaccgccat gacggccgcc tg 22

<210> SEQ ID NO 41
<211> LENGTH: 22
<212> TYPE: DNA
<213> ORGANISM: Human immunodeficiency virus

<400> SEQUENCE: 41
gacaccgcca tgacggccgc ct 22

<210> SEQ ID NO 42
<211> LENGTH: 22
<212> TYPE: DNA
<213> ORGANISM: Human immunodeficiency virus

<400> SEQUENCE: 42
cgacaccgcc atgacggccg cc 22